United States Patent
Schentag et al.

(10) Patent No.: US 10,588,857 B2
(45) Date of Patent: Mar. 17, 2020

(54) GASTROINTESTINAL SITE-SPECIFIC ORAL VACCINATION FORMULATIONS ACTIVE ON THE ILEUM AND APPENDIX

(71) Applicant: Therabiome, LLC, Marlboro, NJ (US)

(72) Inventors: Jerome J. Schentag, Amherst, NJ (US); Mohan Kabadi, Marlboro, NJ (US)

(73) Assignee: Therabiome, LLC, Marlboro, NJ (US)

(*) Notice: Subject to any disclaimer, the term of this patent is extended or adjusted under 35 U.S.C. 154(b) by 1016 days.

(21) Appl. No.: 14/387,979

(22) PCT Filed: Mar. 14, 2013

(86) PCT No.: PCT/US2013/031483
§ 371 (c)(1),
(2) Date: Sep. 25, 2014

(87) PCT Pub. No.: WO2013/148258
PCT Pub. Date: Oct. 3, 2013

(65) Prior Publication Data
US 2015/0071994 A1 Mar. 12, 2015

Related U.S. Application Data

(60) Provisional application No. 61/617,367, filed on Mar. 29, 2012.

(51) Int. Cl.
*A61K 9/00* (2006.01)
*A61K 39/00* (2006.01)

(52) U.S. Cl.
CPC ............ *A61K 9/0065* (2013.01); *A61K 39/00* (2013.01)

(58) Field of Classification Search
None
See application file for complete search history.

(56) References Cited

U.S. PATENT DOCUMENTS

| | | |
|---|---|---|
| 4,193,985 A | 3/1980 | Bechgaard et al. |
| 4,230,687 A | 10/1980 | Sair et al. |
| 4,256,108 A | 3/1981 | Theeuwes |
| 4,572,833 A | 2/1986 | Pedersen et al. |
| 4,579,734 A | 4/1986 | Hata et al. |
| 4,789,724 A | 12/1988 | Domb et al. |
| 4,839,281 A | 6/1989 | Gorbach et al. |
| 4,857,311 A | 8/1989 | Domb et al. |
| 4,888,176 A | 12/1989 | Langer et al. |
| 5,032,399 A | 7/1991 | Gorbach et al. |
| 5,079,164 A | 1/1992 | Kirkovits et al. |
| 5,176,911 A | 1/1993 | Tosi et al. |
| 5,401,512 A | 3/1995 | Rhodes et al. |
| 5,413,785 A | 5/1995 | Nanji |
| 5,525,634 A | 6/1996 | Sintov et al. |
| 5,541,170 A | 7/1996 | Rhodes et al. |
| 5,573,779 A | 11/1996 | Sato et al. |
| 5,599,795 A | 2/1997 | McCann et al. |
| 5,603,953 A | 2/1997 | Herbig et al. |
| 5,622,721 A | 4/1997 | Dansereau et al. |
| 5,650,170 A | 7/1997 | Wright et al. |
| 5,681,584 A | 10/1997 | Savastano et al. |
| 5,686,105 A | 11/1997 | Kelm et al. |
| 5,733,568 A | 3/1998 | Ford |
| 5,811,128 A | 9/1998 | Tice et al. |
| 5,843,479 A | 12/1998 | Kelm et al. |
| 5,885,590 A | 3/1999 | Hunter et al. |
| 5,900,252 A | 5/1999 | Calanchi et al. |
| 5,962,024 A | 10/1999 | Marvola et al. |
| 6,103,227 A | 8/2000 | Wolf et al. |
| 6,132,710 A | 10/2000 | Panigrahi et al. |
| 6,221,350 B1 | 4/2001 | Brown et al. |
| 6,306,422 B1 | 10/2001 | Batich et al. |
| 6,479,051 B1 | 11/2002 | Bruce et al. |
| 6,506,407 B2 | 1/2003 | Watanabe et al. |
| 6,638,534 B1 | 10/2003 | Ishibashi et al. |
| 6,641,808 B1 | 11/2003 | Bojrab |
| 6,696,057 B1 | 2/2004 | Bojrab |
| 6,746,671 B2 | 6/2004 | Steidler et al. |
| 6,811,786 B1 | 11/2004 | Farmer et al. |
| 6,849,256 B1 | 2/2005 | Farmer |
| 6,861,053 B1 | 3/2005 | Lin et al. |
| 7,081,239 B2 | 7/2006 | Lin |
| 7,094,425 B2 | 8/2006 | Scott et al. |
| 7,101,565 B2 | 9/2006 | Monte |
| 7,192,581 B2 | 3/2007 | Park et al. |
| 7,344,867 B2 | 3/2008 | Connolly |
| 7,410,651 B2 | 8/2008 | Villa et al. |
| 7,431,943 B1 | 10/2008 | Villa et al. |
| 7,601,799 B2 | 10/2009 | Steidler |
| 7,670,612 B2 | 3/2010 | Miller |
| 7,670,617 B2 | 3/2010 | Pather et al. |
| 7,670,627 B2 | 3/2010 | Shefer et al. |
| 7,718,171 B2 | 5/2010 | Flambard |
| 7,731,976 B2 | 6/2010 | Cobb |

(Continued)

FOREIGN PATENT DOCUMENTS

| | | |
|---|---|---|
| CN | 2601094 Y | 1/2004 |
| CN | 1781477 A | 6/2006 |

(Continued)

OTHER PUBLICATIONS

Akers, S.N. et al. "Regulation of cancer germline antigen gene expression: implications for cancer immunotherapy." Future Oncol. 2010;6(5):717-32.

(Continued)

*Primary Examiner* — Patricia Duffy
*Assistant Examiner* — Garen Gotfredson
(74) *Attorney, Agent, or Firm* — Goodwin Procter LLP

(57) ABSTRACT

The invention provides oral vaccine formulations which deliver an antigen in the vicinity of the distal ileum and the area of the ileal Brake and/or the appendix. These vaccines are useful in the treatment and/or prevention of variety of disorders, including viral and bacterial infections and cancers. Related methods of treatment which use the oral vaccine formulations of the invention are also provided.

18 Claims, 6 Drawing Sheets

(56) References Cited

U.S. PATENT DOCUMENTS

| | | | |
|---|---|---|---|
| 7,749,494 B2 | 7/2010 | Renaud et al. | |
| 7,749,509 B2 | 7/2010 | Cobb et al. | |
| 7,759,105 B2 | 7/2010 | Cobb et al. | |
| 7,780,961 B2 | 8/2010 | Steidler | |
| 7,927,584 B2 | 4/2011 | Allende | |
| 7,998,474 B2 | 8/2011 | Kelly | |
| 8,029,823 B2 | 10/2011 | Villa et al. | |
| 8,066,987 B2 | 11/2011 | Moore et al. | |
| 8,092,793 B2 | 1/2012 | Cui | |
| 8,168,594 B2 | 5/2012 | Paterson | |
| 8,192,733 B2 | 6/2012 | Cobb et al. | |
| 8,197,805 B2 | 6/2012 | Lin et al. | |
| 8,246,989 B2 | 8/2012 | Dansereau et al. | |
| 8,263,146 B2 | 9/2012 | Bengtsson-Riveros et al. | |
| 8,293,273 B2 | 10/2012 | Villa et al. | |
| RE43,799 E | 11/2012 | Villa et al. | |
| 8,323,692 B2 | 12/2012 | Frisbee | |
| 8,338,162 B2 | 12/2012 | Igimi et al. | |
| 8,361,497 B2 | 1/2013 | Miller | |
| 8,367,418 B2 | 2/2013 | Monte et al. | |
| 8,440,178 B2 | 5/2013 | Darimont et al. | |
| 8,454,949 B2 | 6/2013 | Arigoni et al. | |
| 8,460,648 B2 | 6/2013 | Borody | |
| 8,481,299 B2 | 7/2013 | Gueniche | |
| 8,529,887 B2 | 9/2013 | Schiffrin | |
| 8,557,560 B2 | 10/2013 | Martín Jiménez et al. | |
| 8,784,888 B2 | 7/2014 | Villa et al. | |
| 8,906,668 B2 | 12/2014 | Henn et al. | |
| 8,999,721 B2 | 4/2015 | Schentag et al. | |
| 9,011,834 B1 | 4/2015 | McKenzie et al. | |
| 9,028,841 B2 | 5/2015 | Henn et al. | |
| 9,180,147 B2 | 11/2015 | McKenzie et al. | |
| 9,241,911 B2 | 1/2016 | Miller | |
| 9,370,528 B2 | 6/2016 | Schentag et al. | |
| 9,443,060 B2 | 9/2016 | Schentag et al. | |
| 9,539,216 B2 | 1/2017 | Miller | |
| 9,757,346 B2 | 9/2017 | Fayad | |
| 9,907,755 B2 | 3/2018 | Kabadi et al. | |
| 2001/0026807 A1* | 10/2001 | Watts | A61K 9/4891 424/463 |
| 2003/0092145 A1* | 5/2003 | Jira | A61K 39/015 435/173.3 |
| 2003/0194428 A1 | 10/2003 | Miller et al. | |
| 2003/0194429 A1 | 10/2003 | Miller et al. | |
| 2003/0194430 A1 | 10/2003 | Miller et al. | |
| 2003/0194431 A1 | 10/2003 | Miller et al. | |
| 2004/0062757 A1 | 4/2004 | Finegold | |
| 2004/0120931 A1 | 6/2004 | Myatt | |
| 2006/0093592 A1 | 5/2006 | Cheruvanky et al. | |
| 2006/0210631 A1 | 9/2006 | Patel et al. | |
| 2007/0141039 A1 | 6/2007 | Collins et al. | |
| 2007/0280911 A1 | 12/2007 | Cobb et al. | |
| 2008/0020018 A1* | 1/2008 | Moodley | A61K 9/5073 424/433 |
| 2008/0233184 A1* | 9/2008 | Looney | A61K 9/4808 424/451 |
| 2008/0261916 A1 | 10/2008 | Jaszberenyi et al. | |
| 2008/0286252 A1 | 11/2008 | Sinnott | |
| 2008/0311201 A1 | 12/2008 | Der-Yang et al. | |
| 2009/0035370 A1 | 2/2009 | Bortz et al. | |
| 2009/0162322 A1 | 6/2009 | Rudolph et al. | |
| 2010/0209520 A1* | 8/2010 | Kubo | A61K 9/5078 514/1.1 |
| 2010/0221321 A1 | 9/2010 | Miller et al. | |
| 2010/0247489 A1 | 9/2010 | Saur-Brosch | |
| 2010/0316617 A1 | 12/2010 | Renaud et al. | |
| 2011/0268795 A1 | 11/2011 | Fayad | |
| 2012/0093923 A1 | 4/2012 | Miller et al. | |
| 2012/0183513 A1 | 7/2012 | Neu et al. | |
| 2012/0247993 A1 | 10/2012 | Palazzi et al. | |
| 2012/0276149 A1 | 11/2012 | Littman et al. | |
| 2013/0089524 A1 | 4/2013 | Petit et al. | |
| 2013/0136791 A1 | 5/2013 | Miller | |
| 2013/0149339 A1 | 6/2013 | Honda et al. | |
| 2013/0164380 A1 | 6/2013 | Durum et al. | |
| 2013/0266539 A1 | 10/2013 | Borody | |
| 2014/0328803 A1 | 11/2014 | McKenzie et al. | |
| 2015/0190435 A1 | 7/2015 | Henn et al. | |
| 2015/0352189 A1 | 12/2015 | Schentag et al. | |
| 2016/0030494 A1 | 2/2016 | Henn et al. | |
| 2016/0040215 A1 | 2/2016 | Henn et al. | |

FOREIGN PATENT DOCUMENTS

| | | |
|---|---|---|
| EP | 0587220 B1 | 5/1997 |
| GB | 2238243 A | 5/1991 |
| GB | 2365336 A | 2/2002 |
| GB | 2490671 A | 11/2012 |
| RU | 2442572 C1 | 2/2012 |
| WO | WO-89/11269 A1 | 11/1989 |
| WO | WO-1991/016881 A1 | 11/1991 |
| WO | WO199535100 | 12/1995 |
| WO | WO200151008 | 7/2001 |
| WO | WO2007013794 | 2/2007 |
| WO | WO-2008/122967 A2 | 10/2008 |
| WO | WO2008122965 | 10/2008 |
| WO | WO-2010/027498 A2 | 3/2010 |
| WO | WO-2012/077038 A1 | 6/2012 |
| WO | WO-2012/118712 A2 | 9/2012 |
| WO | WO2013037068 | 3/2013 |
| WO | WO2013050792 | 4/2013 |
| WO | WO-2013/063527 A1 | 5/2013 |
| WO | WO2013080561 | 6/2013 |
| WO | WO2014121298 | 8/2014 |
| WO | WO2014121301 | 8/2014 |
| WO | WO2014121302 | 8/2014 |
| WO | WO2014121304 | 8/2014 |
| WO | WO2014145958 | 9/2014 |
| WO | WO2014153194 | 9/2014 |

OTHER PUBLICATIONS

Ano, G. et al. "A new oral vaccine candidate based on the micro-encapsulation by spray-drying of inactivated Vibrio cholerae." Vaccine. 2011;29(34):5758-64.

Beagley, K.W. et al. "Recombinant murine IL-5 induces high rate IgA synthesis in cycling IgA-positive Peyer's patch B cells." J Immunol. 1988;141(6):2035-42.

Carter, K.C. et al. "Translation of an experimental oral vaccine formulation into a commercial product." Methods. 2006;38(2):65-8.

Cassilly, D. et al. "Gastric emptying of a non-digestible solid: assessment with simultaneous SmartPill pH and pressure capsule, antroduodenal manometry, gastric emptying scintigraphy." Neurogastroenterol Motil. 2008;20(4):311-9.

Chen, Y.T. et al. "Cancer/testis antigen CT45: analysis of mRNA and protein expression in human cancer." Int J Cancer. 2009;124(12):2893-8.

Clark, S. et al. "Assessment of different formulations of oral *Mycobacterium bovis* Bacille Calmette-Guerin (BCG) vaccine in rodent models for Immunogenicity and protection against aerosol challenge with *M. bovis*." Vaccine. 2008;26(46):5791-7.

Conry, S.J. et al. "Genetically Associated CD16+56—Natural Killer Cell Interferon (IFN)-alphaR Expression Regulates Signaling and Is Implicated in IFN-alpha-Induced Hepatitis C Virus Decline." J Infect Dis. 2012;205(7):1131-41.

Crooks, E.T. et al. "Enzyme digests eliminate nonfunctional Env from HIV-1 particle surfaces, leaving native Env trimers intact and viral infectivity unaffected." J Virol. 2011;85(12):5825-39.

Delgado, A. et al. "PLG microparticles stabilised using enteric coating polymers as oral vaccine delivery systems." Vaccine. 1999;17(22):2927-38.

Duijvestijn, A. et al. "Mechanisms and regulation of lymphocyte migration." Immunol Today. 1989;10(1):23-8.

Eldridge, J.H. et al. "Biodegradable microspheres: vaccine delivery system for oral immunization." Curr Top Microbiol Immunol. 1989;146:59-66.

(56) References Cited

OTHER PUBLICATIONS

Everson, M.P. et al. "Dendritic cells from Peyer's patch and spleen induce different T helper cell responses." J Interferon Cytokine Res. 1998;18(2):103-15.
Everson, M.P. et al. "Dendritic cells from different tissues induce production of different T cell cytokine profiles." J Leukoc Biol. 1996;59(4):494-8.
Everson, M.P. et al. "Dendritic cells regulate development of alloantigenic and mitogenic TH1 versus TH2 responses." Adv Exp Med Biol. 1995;378:347-9.
Farstad, I.N. et al. "Heterogeneity of M-cell-associated B and T cells in human Peyer's patches." Immunology. 1994;83(3):457-64.
Farstad, I.N. et al. "Do human Peyer's patches contribute to the intestinal intraepithelial gamma/delta T-cell population?" Scand J Immunol. 1993;38(5):451-8.
Fattoni, A. et al. "Safety and immunogenicity of a booster dose of *Staphylococcus aureus* types 5 and 8 capsular polysaccharide conjugate vaccine (StaphVAX) in hemodialysis patients." Vaccine. 2004;23(5):656-63.
Fattom, A.I. et al. "Development of StaphVAX, a polysaccharide conjugate vaccine against *S. aureus* infection: from the lab bench to phase III clinical trials." Vaccine. 2004;22(7):880-7.
Faure, G.C. et al. "Peripheral blood specific antibody-forming cells after oral stimulation with a ribosomal vaccine." Dev Biol Stand. 1992;77:175-81.
Grafmueller, S. et al. "Differential Antigen Specificity of Hepatitis C Virus-Specific Interleukin 17- and Interferon gamma-Producing CD8+ T Cells During Chronic Infection." J Infect Dis. 2012;205(7):1142-6.
Halliday, J. et al. "Vaccination for hepatitis C virus: closing in on an evasive target." Expert Rev Vaccines. 2011;10(5):659-72.
Halstensen, T.S. et al. "Gluten stimulation of coeliac mucosa in vitro induces activation (CD25) of lamina propria CD4+ T cells and macrophages but no crypt-cell hyperplasia." Scand J Immunol. 1993;38(6):581-90.
Hamann, A. et al. "Molecules and regulation in lymphocyte migration." Immunol Rev. 1989;108:19-44.
Hanninen, A. et al. "Macrophages, T cell receptor usage, and endothelial cell activation in the pancreas at the onset of insulin-dependent diabetes mellitus." J Clin Invest. 1992;90(5):1901-10.
Hanson, L.A. et al. "The discovery of secretory IgA and the mucosal immune system." Immunol Today. 1993;14(8):416-7.
Jones, T. Current Opinon in Investigational Drugs, StaphVAX (Nabi). Curr Opin Investig Drugs. 2002;3(1):48-50.
Kantele, J.M. et al. "Mucosally activated circulating human B cells in diarrhea express homing receptors directing them back to the gut." Gastroenterology. 1996;110(4):1061-7.
Kim, Y.H. et al. "Diet-induced obesity dramatically reduces the efficacy of a 2009 pandemic H1N1 vaccine in a mouse model." J Infect Dis. 2012;205(2):244-51.
Kim, Y.C. et al. "Enhanced memory responses to seasonal H1N1 influenza vaccination of the skin with the use of vaccine-coated microneedles." J Infect Dis. 2010;201(2):190-8.
Kiyono, H. et al. "Murine Peyer's patch T cell clones. Characterization of antigen-specific helper T cells for immunoglobulin A responses." J Exp Med. 1982;156(4):1115-30.
Kozbor, D. "Cancer vaccine with mimotopes of tumor-associated carbohydrate antigens." Immunol Res. 2010;46(1-3):23-31.
Larhed, A. et al. "Starch microparticles as oral vaccine adjuvant: antigen-dependent uptake in mouse intestinal mucosa." J Drug Target. 2004;12(5):289-96.
Li, Q. et al. "Antigen-induced Erk1/2 activation regulates Ets-l-mediated sensitization of CD8+ T cells for IL-12 responses." J Leukoc Biol. 2010;87(2):257-63.
Louie, J.K. et al. "A novel risk factor for a novel virus: obesity and 2009 pandemic influenza A (H1N1)." Clin Infect Dis. 2011;52(3):301-12.
Malaspina, A. et al. "Human immunodeficiency virus type 1 bound to B cells: relationship to virus replicating in CD4+ T cells and circulating in plasma." J Virol. 2002;76(17):8855-63.
Mhawech-Fauceglia, P. et al. "Prostate-specific membrane antigen expression is a potential prognostic marker in endometrial adenocarcinoma." Cancer Epidemiol Biomarkers Prev. 2008;17(3):571-7.
Moir, S. et al. "Pathogenic mechanisms of HIV disease." Annu Rev Pathol. 2011;6:223-48.
Moir, S. et al. "B cells in HIV infection and disease." Nat Rev Immunol. 2009;9(4):235-45.
Moir, S. et al. "Evidence for HIV-associated B cell exhaustion in a dysfunctional memory B cell compartment in HIV-infected viremic individuals." J Exp Med. 2008;205(8):1797-805.
Moir, S. et al. "Normalization of B cell counts and subpopulations after antiretroviral therapy in chronic HIV disease." J Infect Dis. 2008;197(4):572-9.
Moir, S. et al. "Perturbations in B cell responsiveness to CD4+ T cell help in HIV-infected individuals." Proc Natl Acad Sci U S A. 2003;100(10):6057-62.
Moir, S. et al. "Prospects for an HIV vaccine: leading B cells down the right path." Nat Struct Mol Biol. 2011;18(12):1317-21.
Muller, F. et al. "Nonspecific oral immunity in individuals with HIV infection." J Acquir Immune Defic Syndr. 1992;5(1):46-51.
Nilssen, D.E. et al. "Duodenal intraepithelial gamma/delta T cells and soluble CD8, neopterin, and beta 2-microglobulin in serum of IgA-deficient subjects with or without IgG subclass deficiency." Clin Exp Immunol. 1993;94(1):91-8.
Nilssen, D.E. et al. "B-cell activation in duodenal mucosa after oral cholera vaccination in IgA deficient subjects with or without IgG subclass deficiency." Scand J Immunol. 1993;38(2):201-8.
Odunsi, K. et al. "NY-ESO-1 and LAGE-1 cancer-testis antigens are potential targets for immunotherapy in epithelial ovarian cancer." Cancer Res. 2003;63(18):6076-83.
Pniewski, T. et al. "Low-dose oral immunization with lyophilized tissue of herbicide-resistant lettuce expressing hepatitis B surface antigen for prototype plant-derived vaccine tablet formulation." J Appl Genet. 2011;52(2):125-36.
Pniewski, T. et al. "Plant expression, lyophilisation and storage of HBV medium and large surface antigens for a prototype oral vaccine formulation." Plant Cell Rep. 2012;31(3):585-95.
Prabakaran, M. et al. "Reverse micelle-encapsulated recombinant baculovirus as an oral vaccine against H5N1 infection in mice." Antiviral Res. 2010;86(2):180-7.
Qian, F. et al. "Tumor associated antigen recognition by autologous serum in patients with breast cancer." Int J Mol Med. 2005;15(1):137-44.
Raghuraman, S. et al. "Spontaneous clearance of chronic hepatitis C virus infection is associated with appearance of neutralizing antibodies and reversal of T-cell exhaustion." J Infect Dis. 2012;205(5):763-71.
Rahman, F. et al. "Effects of antiviral therapy on the cellular immune response in acute hepatitis C." Hepatology. 2004;40(1):87-97.
Rajkannan, R. et al. "Development of hepatitis B oral vaccine using B-cell epitope loaded PLG microparticles." Vaccine. 2006;24(24):5149-57.
Rao, S.S. et al. "Investigation of colonic and whole-gut transit with wireless motility capsule and radiopaque markers in constipation." Clin Gastroenterol Hepatol. 2009;7(5):537-44.
Rescia, V.C. et al. "Dressing liposomal particles with chitosan and poly(vinylic alcohol) for oral vaccine delivery." J Liposome Res. 2011;21(1):38-45.
Rognum, T.O. et al. "Development of intestinal mucosal immunity in fetal life and the first postnatal months." Pediatr Res. 1992;32(2):145-9.
Scott, H. et al. "The immune system of the gastrointestinal tract." Pediatr Allergy Immunol. 1993;4(3 Suppl):7-15.
Segal, B.H. et al. "Heat shock proteins as vaccine adjuvants in infections and cancer." Drug Discov Today. 2006;11(11-12):534-40.
Shamsuzzaman, S. et al. "Robust gut associated vaccine-specific antibody-secreting cell responses are detected at the mucosal surface of Bangladeshi subjects after immunization with an oral killed bivalent V. cholerae Jan. O1/O139 whole cell cholera vaccine: comparison with other mucosal and systemic responses." Vaccine. 2009;27(9):1386-92.

(56) References Cited

OTHER PUBLICATIONS

Sovran, L. World Vaccine Congress Lyon—Terrapinn's 11th Annual Congress. IDrugs. 2009;12(12):738-41.
Spalding, D.M. et al. "Peyer's patch dendritic cells: isolation and functional comparison with murine spleen dendritic cells." Immunobiology. 1984;168(3-5):380-90.
Spalding, D.M. et al. "Preferential induction of polyclonal IgA secretion by murine Peyer's patch dendritic cell-T cell mixtures." J Exp Med. 1984;160(3):941-6.
Spalding, D.M. et al. "Accessory cells in murine Peyer's patch. I. Identification and enrichment of a functional dendritic cell." J Exp Med. 1983;157(5):1646-59.
*Staphylococcus aureus* vaccine conjugate—Nabi: Nabi-StaphVAX, StaphVAX. Drugs R D. 2003;4(6):383-5.
Strickland, G.T. et al. "Hepatitis C vaccine: supply and demand." Lancet Infect Dis. 2008;8(6):379-86.
Tammela, J. et al. "SCP-1 cancer/testis antigen is a prognostic indicator and a candidate target for immunotherapy in epithelial ovarian cancer." Cancer Immun. 2004;4:10.
Theilacker, C. et al. "Protection Against *Staphylococcus aureus* by Antibody to the Polyglycerolphosphate Backbone of Heterologous Lipoteichoic Acid." J Infect Dis. 2012;205(7):1076-85.
Tomaras, G.D. et al. "Polyclonal B cell responses to conserved neutralization epitopes in a subset of HIV-1-infected individuals." J Virol. 2011;85(21):11502-19.
Torii, M. et al. "Lymphoid cell responses to bacterial cell wall components: polyclonal and immune responses of murine B cells to *Streptococcus mutans* carbohydrate antigens." J Immunol. 1981;127(5):2106-12.
Tsuji, T. et al. "Antibody-targeted NY-ESO-1 to mannose receptor or DEC-205 in vitro elicits dual human CD8+ and CD4+ T cell responses with broad antigen specificity." J Immunol. 2011;186(2):1218-27.
Tsuji, T. et al. "Split T cell tolerance against a self/tumor antigen: spontaneous CD4+ but not CD8+ T cell responses against p53 in cancer patients and healthy donors." PLoS One. 2011;6(8):e23651.
Wang, X.Y. et all. "Characterization of heat shock protein 110 and glucose-regulated protein 170 as cancer vaccines and the effect of fever-range hyperthermia on vaccine activity." J Immunol. 2001;166(1):490-7.
Weisman, L.E. "Antibody for the prevention of neonatal noscocomial staphylococcal infection: a review of the literature." Arch Pediatr. 2007;14 Suppl 1:S31-4.
Woloszynska-Read, A. et al. "BORIS/CTCFL expression is insufficient for cancer-germline antigen gene expression and DNA hypomethylation in ovarian cell lines." Cancer Immun. 2010;10:6.
Woloszynska-Read, A. et al. "Coordinated cancer germline antigen promoter and global DNA hypomethylation in ovarian cancer: association with the BORIS/CTCF expression ratio and advanced stage." Clin Cancer Res. 2011;17(8):2170-80.
Barrera, D.A. et al. (1993) "Synthesis and RGD peptide modification of a new biodegradable copolymer: poly(lactic acid-co-lysine)," J. Am. Chem. Soc., 115(23)11010-11011.
Boussif, O. et al. (1995) "A versatile vector for gene and oligo-nucleotide transfer into cells in culture and in vivo: polyethylenimine," Proc. Natl. Acad. Sci. U.S.A., 92(16):7297-301.
Chavarri et al. (2010) "Microencapsulation of a probiotic and prebiotic in alginate-chitosan capsules improves survival in simulated gastro-intestinal conditions," International Journal of Food Microbiology, 142(1):185-189.
Chonn et al.(1995) "Recent advances in liposomal drug-delivery systems," Curr. Opin. Biotechnol., 6(6):698-708.
Gliko-Kabir, I. et al. (1998) "Low swelling, crosslinked guar and its potential use as colon-specific drug carrier," Pharm. Res., 15(7):1019-25.
Haensler, J. et al. (1993) "Polyamidoamine cascade polymers mediate efficient transfection of cells in culture," Bioconjug. Chem., 4(5):372-9.
Hovgaard and Brøndsted (1995) "Dextran hydrogels for colon-specific drug delivery," Journal of Controlled Release (Proceedings of the Third European Symposium on Controlled Drug Delivery), 36: 159-166.
Kabanov A.V., et al. (1995) "DNA complexes with polycations for the delivery of genetic material into cells," Bioconjug. Chem., 6(1):7-20.
Kopecek et al. (1992) "Polymers for colon-specific drug delivery," J. Control Release, 19:121-130.
Kukowska-Latallo, J.F. (1996) "Efficient transfer of genetic material into mammalian cells using Starburst polyamidoamine dendrimers," Proc. Natl. Acad. Sci. U.S.A., 93(10):4897-902.
Kwon et al. (1989) "Pseudopoly(amino acids): a study of the synthesis and characterization of poly(trans-4-hydroxy-N-acyl-L-proline esters)," Macromolecules, 22(8):3250-3255.
Langer, R. et al. (1976) "Polymers for the sustained release of proteins and other macromolecules," Nature, 263(5580):797-800.
Lehmann et al.(1991) "Methacrylate-Galactomannan Coating for Colon-Specified Drug Delivery," Proc. Int. Symp. Contr. Rel. Bioact. Mater., 8:331-32.
Li, F.Q. et al. (2007) "Oral vaccination and vaccine-entrapped microparticle delivery system," Yao Xue Xue Bao., 42(3):245-51.
Lim et al.(1999) "A Self-Destroying Polycationic Polymer: Biodegradable Poly(4-hydroxy-l-proline ester)," J. Am. Chem. Soc., 121(24):5633-5639.
Milojevic et al. (1993) "In Vitro and In Vivo Evaluation of Amylose Coated Pellets for Colon Specific Drug Delivery," Proc. Int. Symp. Contr. Rel. Bioact. Mater., 20:288-89.
Plummer et al. (2004) "Clostridium difficile pilot study: effects of probiotic supplementation on the incidence of C. difficle diarrhoea," International Microbiology, 7(1): 59-62.
Putnam, D. et al. (1999) "Poly(4-hydroxy-L-proline ester): Low-temperature Polycondensation and Plasmid DNA Complexation," Macromolecules, 32:3658-3662.
Ringel et al. (2012) "Using probiotics in Gastrointestinal disorders." Am. J. Gastroenterol. Suppl., 1: 34-40.
Rubinstein, A. et al. (1993) "In vitro evaluation of calcium pectinate: a potential colon-specific drug delivery carrier," Pharm. Res., 10(2):258-63.
Rubinstein, A. et al.(1992) "Colonic drug delivery: enhanced release of indomethacin from cross-linked chondroitin matrix in rat cecal content," Pharm. Res., 9(2):276-8.
Siefke, et al. (1994) "Colon Targeting with β-CD Matrix Films," Eur. J. Pharm. Biopharm., 40(suppl.):33S.
Tang, M.X. et al. (1996) "In vitro gene delivery by degraded polyamidoamine dendrimers," . Bioconjug Chem., 7(6):703-14.
Toorisaka, E. et al. (2005) "An enteric-coated dry emulsion formulation for oral insulin delivery," J. Control. Release, 107(10):91-96.
Zauner, W. et al. (1998) "Polylysine-based transfection systems utilizing receptor-mediated delivery," Adv. Drug Deliv. Rev., 30(1-3):97-113.
Zhou et al. (1990) "Preparation of poly(L-serine ester): a structural analog of conventional poly(L-serine)," Macromolecules, 23(14):3399-3406.
Gupta, V.K. et al. "A novel pH-and time-based multi-unit potential colonic drug delivery system. I. Development." International Journal of Pharmaceutics, Feb. 2001, vol. 213, No. 1-2, pp. 83-91.
Dewhirst, F.E. et al. "Phylogeny of the Defined Murine Mircobiota: Altered Schaedler Flora." Applied and Environmental Microbiology, 1999;65(8): 3287-3292.
Friend, D.R. "New Oral Delivery Systems for Treatment of inflammatory bowel disease." Advanced Drug Delivery Reviews, 2005;57:247-265.
Geuking, M.B. et al. "Intestinal Bacterial Colonization Induces Mutualistic Regulatory T Cell Responses." Immunity, 2011;34:794-806.
Goldin, B.R. et al. "Clinical Indications for Probiotics: An Overview." CID, 2008;46: S96-100.
Huh, K.M. et al. "pH-Sensitive Polymers for Drug Delivery." Macromolecular Research, 2012;20(3):224-233.
Ivanov, I.I. et al. "Segmented filamentous bacteria take the stage." Mucosal Immunol. 2010;3(3):209-212.

(56) References Cited

OTHER PUBLICATIONS

Khan, M.Z. et al. "A pH-dependent colon targeted oral drug delivery system using methacrylic acid copolymers. I. Manipulation of drug release using Eudragit® L100-55 and Eudragit® S100 combinations." Journal of Controlled Release, 1999;58:215-222.

Khan, M.Z. et al. "A pH-dependent colon targeted oral drug delivery system using methacrylic acid copolymers. II. Manipulation of drug release using Eudragit® L100 Eudragit S100 combinations." Drug Development and Industrial Pharmacy, 2000;26(5):549-554.

Krishnamachari, Y. et al. "Development of pH-and time-dependent oral microparticles to optimize budesonide delivery to ileum and colon." International Journal of Pharmaceuticals, 2007;338:238-247.

Li, J. et al. "In Vitro Evaluation of Dissolution Behavior of a Colon-Specific Drug Delivery System (CODES™) in Multi-pH Media USign United States Pharmacopeia Apparatus II and III." AAPS PharmSciTech, 2002;3(4) article 33 (http://www.aapspharmscitech.org).

Na, Kun et al. "pH-Sensitive Polymers for Drug Delivery." 2005:129-194.

Petrof, E.O. et al. "Stool substitute transplant therapy for the eradication of *Clostridium difficile* infection:'RePOOPulating' the gut." Microbiome, 2013:1(3):112.

Ubeda, C. et al. "Intestinal Microbiota Containing *Barnesiella* Species Cures Vancomycin-Resistant *Enterococcus faecium* Colonization." Infection and Immunity, 2013;81(3):965-973.

U.S. Appl. No. 14/771,830, Targeted Gastrointestinal Tract Delivery of Probiotic Organisms and/or Therapeutic Agents, Sep. 1, 2015.

\* cited by examiner

Because enteric coating release at pH 5.5 alone targets the duodenum
and antigen released in duodenum would not survive transit to reach the colon,
Right Colon and Appendix Delivery Requires BOTH an outer and an Inner Pill Pill within a Pill: Ileal Brake target release (pH 7.3-7.5)
of inner pill, containing Vaccine formulation
for Appendix release at pH 5.5-6.2

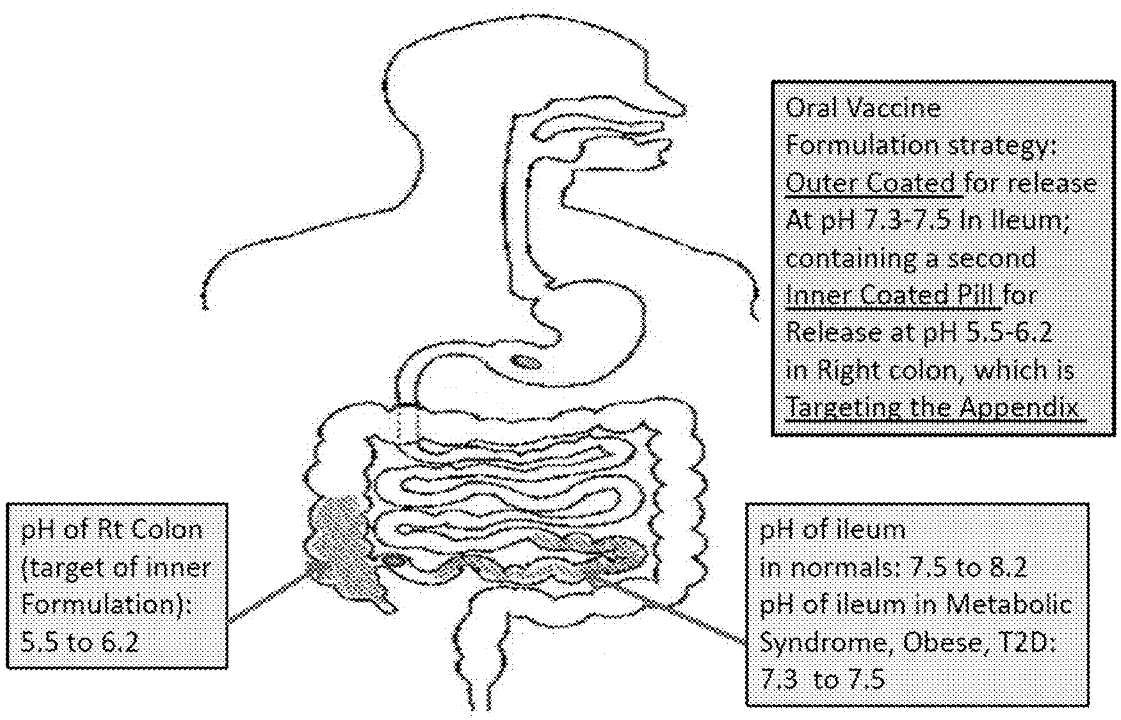

Figure 6

GASTROINTESTINAL SITE-SPECIFIC ORAL VACCINATION FORMULATIONS ACTIVE ON THE ILEUM AND APPENDIX

RELATED APPLICATIONS

This application is filed under the provisions of 35 U.S.C. § 371 and claims the priority of International Patent Application No. PCT/US2013/031483 filed on Mar. 14, 2013 which in turn claims the benefit of priority of provisional application Ser. No. U.S. 61/617,367, filed 29 Mar. 2012, of identical title, which is incorporated by reference in its entirety herein.

FIELD OF THE INVENTION

The invention provides oral vaccine formulations which deliver an antigen in the vicinity of the distal ileum (in certain embodiments, in the colon, in the vicinity of the appendix) and the area of the ileal brake. These vaccines are useful in the treatment and/or prevention of variety of disorders, including viral and bacterial infections and cancers.

Related methods of treatment which use the oral vaccine formulations of the invention are also provided.

BACKGROUND OF THE INVENTION

The gastrointestinal (GI) tract has several regions sharply demarcated by local pH ranging from 5.5 to 8.2. The distal ileum further uniquely contains a region where the usual pH is between 7.3 and 8.2. Notably, this area is relatively devoid of degradation pathways for antigens such as vaccine constructs, yet far more sensitive to their presence.

Many antigens are degraded by the acid and proteolytic conditions of the stomach and anterior GI tract, conditions which make oral vaccination impractical to nearly impossible from a technical point of view. Thus, the distal ileum and the area of the ileal brake, which is optimal for a controlling sensor for nutritional balance, also uniquely contains both the optimum pH conditions for vaccination (stability of antigenic substance) and contains numerous specialized sensing cells (such as Peyer's Patches), that help to define the immune system response to the foreign invader pathogens and in some cases, tumors.

The appendix, by way of example in the art, is a specialized sensor located distal to the ileum in the right colon. It contains lymphoid tissue and has long been thought to be involved in the activation of the B cell response to antigens of all types. Because of relative inaccessibility to formulations, neither the distal ileum nor the appendix has been used as a target site for oral vaccination, and although the use of these areas of lymphoid tissue are logical targets for vaccine delivery, it has been thought impossible to achieve.

Accordingly, the need exists for oral vaccines that enable effective delivery of a wide variety of antigens in the region of the distal ileum and ileal brake, thereby avoiding antigen degradation encountered with known orally-dosed vaccines.

SUMMARY OF THE INVENTION

In one embodiment, the invention provides an oral vaccine formulation which delivers an antigen in the vicinity of the distal ileum, the formulation comprising:
(a) a plurality of cores, each of which comprise:
(1) an antigen;
(2) a first enteric coating which encapsulates the antigen, which is substantially insoluble at a pH of less than a range of between about 7.0 to about 7.6, and which is preferably comprised of one or more compositions selected from the group consisting of poly(dl-lactide-co-glycolide, chitosan (Chi) stabilized with PVA (poly-vinylic alcohol), a lipid, an alginate, carboxymethylethylcellulose (CMEC), cellulose acetate trimellitiate (CAT), hydroxypropylmethyl cellulose phthalate (HPMCP), hydroxypropylmethyl cellulose, ethyl cellulose, color con, food glaze and mixtures of hydroxypropylmethyl cellulose and ethyl cellulose, polyvinyl acetate phthalate (PVAP), cellulose acetate phthalate (CAP), shellac, copolymers of methacrylic acid and ethyl acrylate, and copolymers of methacrylic acid and ethyl acrylate to which a monomer of methylacrylate has been added during polymerization; and optionally
(3) a second enteric coating which is compositionally the same or different as the first coating, which is substantially insoluble at a pH of less than a range of between about 5.5 to about 6.0, which is contained within the encapsulation coating of the first formulation, and which is preferably comprised of one or more compositions selected from the group consisting of polyvinyl acetate phthalate (PVAP), cellulose acetate phthalate (CAP), shellac, copolymers of methacrylic acid and ethyl acrylate, and copolymers of methacrylic acid and ethyl acrylate to which a monomer of methylacrylate has been added during polymerization; and optionally
(b) a pharmaceutically acceptable excipient.

In one embodiment, the antigen is selected from the group consisting of:
(a) an inactivated virus or antigen-suitable fragment thereof (e.g. a peptide fragment having an epitope which elicits an immunogenic response in a patient) selected from the group consisting of Adenoviridae, Flaviviridae, Herpesviridae, Herpadnaviridae, Orthomyxoviridae, Papovaviridae, Paramyxoviridae, Picornaviridae, Poxviridae, Reoviridae, Retroviridae, Rhabdoviridae, Togaviridae, adenovirus, herpes simplex, varicella zoster, cytomegalovirus, Epstein Barr virus, influenza virus of H type 1-7 and N type 1-9, human papilloma viruses, parainfluenza virus, measles virus, respiratory syncytial virus, poliovirus, Coxsackie virus, rhinovirus, vaccinia, variola, rotavirus, human T lymphotropic virus-1, human immunodeficiency virus (HIV), rabies virus, rubella virus, arbovirus, enteroviruses such as polio, cocksackie, Ebstein-Barr virus, cytomegalovirus (CMV), mononucleosis, Rotavirus, Norwalk virus, and Hepatitis A, Hepatitis B, Hepatitis C, viruses; or
(b) inactivated intracellular pathogens or parasite antigen suitable fragments thereof (e.g. a peptide fragment as described above) selected from the group consisting of *Afipia* spp, *Brucella* spp, *Burkholderia pseudomallei, Chlamydia, Coxiella burnetii, Francisella tularensis, Legionella pneumophila, Listeria monocytogenes, Mycobacterium avium, Mycobacterium leprae, Mycobacterium tuberculosis, Neisseria gonorrhoeae, Rickettsiae, Salmonella typhi, Shigella dysenteriae, Yersinia pestis, Plasmodium* spp, *Theileria parva, Toxoplasma gondii, Cryptosporidium parvum, Leishmania, Trypanosoma cruzi* and *Cryptococcus neoformans, Giardia, Cryptosporidia*; or
(c) Inactivated or antigen suitable fragments of a vector transmitted antigen including *Plasmodium* or *borrelia*; or
(d) inactivated bacteria or antigen suitable fragments thereof including cholera, salmonella, *Shigella, Campylobacter, Leptospirosis, Helicobacter pylori* and enterotoxigenic *e-coli* including *E. Coli* O157, and *Listeria* spp, or human pathogenic bacteria or antigen suitable fragments of bacteria including *staphylococcus aureus* and *Streptococcus pneumoniae*; or (e) a cancer-related or cancer cell derived antigen, including, but not limited to, cancer-related antigens selected from the group consisting of the NY-ESO-1 antigen to bladder, brain, breast, esophageal, gastrointestinal, hepatocellular, kidney, lung, melanoma, ovarian, prostate, sarcoma, cervical and uterine tumors, GD2 ganglioside, 47-LDA mimotope of GD2, heat shock proteins, cancer-testis (CT) antigens, epithelial ovarian cancer (EOC) antigen; the therapeutic vaccine of Oncothyreon ONT-10, directed at MUC1, and other targeted therapeutic vaccines of Oncothyreon with or without the accompanying adjuvant PET-Lipid A; and other cancer-related (e.g. ovarian, cervical, pancreatic, hepatocellular, colon, breast, lung, and brain cancer) antigens specifically described or otherwise disclosed in references cited herein.

In a preferred embodiment, the antigen is an attenuated live virus or bacteria.

In a preferred embodiment, the antigen is accompanied in the oral formulation by a specific adjuvant which is purposed to enhance the resulting immune response of the antigen, and released in the ileum of the subject by formulation as illustrated in FIGS. 2-3.

In still another embodiment: (1) the antigen is combined with (e.g. admixed with) a non-specific adjuvant which may serve as an ileal brake hormone releasing substance which is a substance selected from the group consisting of sugars, free fatty acids, polypeptides, amino acids, and compositions that yield sugars, free fatty acids, polypeptides, or amino acids upon digestion; and (2) the combined antigen and ileal brake hormone releasing substance are encapsulated by the first enteric coating.

In still another embodiment, the invention provides an oral vaccine formulation which delivers an antigen in the vicinity of the distal ileum, the formulation comprising:
(a) a first core population comprising a plurality of cores, each of which comprise:
(1) an antigen and optionally, an adjuvant;
(2) a first enteric coating which encapsulates the antigen and optional adjuvant, which is substantially insoluble at a pH of less than a range of between about 7.0 to about 7.6, and which is preferably comprised of one or more compositions selected from the group consisting of poly(dl-lactide-co-glycolide, chitosan (Chi) stabilized with PVA (poly-vinylic alcohol), a lipid, an alginate, carboxymethylethylcellulose (CMEC), cellulose acetate trimellitiate (CAT), hydroxypropylmethyl cellulose phthalate (HPMCP), hydroxypropylmethyl cellulose, ethyl cellulose, color con, food glaze and mixtures of hydroxypropylmethyl cellulose and ethyl cellulose, polyvinyl acetate phthalate (PVAP), cellulose acetate phthalate (CAP), shellac, copolymers of methacrylic acid and ethyl acrylate, and copolymers of methacrylic acid and ethyl acrylate to which a monomer of methylacrylate has been added during polymerization; and optionally (see FIGS. 4-6)
(3) an additional appendix targeted dosage of the antigen and optional adjuvant, wherein a second enteric coating which is compositionally the same or different as the first coating, which is substantially insoluble at a pH of less than a range of about 5.5, and which is preferably comprised of one or more compositions selected from the group consisting of copolymers of methacrylic acid and ethyl acrylate to which a monomer of methylacrylate has been added during polymerization to ensure release of contents at pH 5.5 to 6.0;
(b) a second core population comprising a plurality of cores, each of which comprise:
(1) the antigen and an optional adjuvant; and
(2) an enteric coating which encapsulates the antigen, which is substantially insoluble at a pH of less than a range of between about 5.0 to about 6.5, and which is preferably comprised of one or more compositions selected from the group consisting of shellac, copolymers of methacrylic acid and ethyl acrylate, and copolymers of methacrylic acid and ethyl acrylate to which a monomer of methylacrylate has been added during polymerization; and optionally
(b) a pharmaceutically acceptable excipient.

In still another embodiment, the invention provides an oral vaccine formulation which delivers an antigen in the vicinity of the appendix and/or right colon in a manner illustrated by FIGS. 4-6 for example, the formulation comprising:
(a) a plurality of cores, each of which comprise:
(1) an antigen and optionally an adjuvant;
(2) an inner or first coating layer which (i) is enteric (ii) encapsulates the antigen and optional adjuvant (iii) is substantially insoluble at a pH of less than a range of between about 1.0 to about 5.0, and (iv) which is preferably comprised of one or more compositions selected from the group consisting of shellac, copolymers of methacrylic acid and ethyl acrylate, and copolymers of methacrylic acid and ethyl acrylate to which a monomer of methylacrylate has been added during polymerization;
(3) optionally, a second coating layer which encapsulates the first enteric coating layer and which comprises a nutritional substance selected from the group consisting of sugars, free fatty acids, polypeptides, amino acids, and compositions that yield sugars, free fatty acids, polypeptides, or amino acids upon digestion which may function as adjuvants; and
(4) a second/third coating layer which (i) is enteric (ii) encapsulates the first or second coating layer (iii) is substantially insoluble at a pH of less than a range of between about 7.0 to about 7.6, and (iv) which is preferably comprised of one or more compositions selected from the group consisting of poly(dl-lactide-co-glycolide, chitosan (Chi) stabilized with PVA (poly-vinylic alcohol), a lipid, an alginate, carboxymethylethylcellulose (CMEC), cellulose acetate trimellitiate (CAT), hydroxypropylmethyl cellulose phthalate (HPMCP), hydroxypropylmethyl cellulose, ethyl cellulose, color con, food glaze and mixtures of hydroxypropylmethyl cellulose and ethyl cellulose, polyvinyl acetate phthalate (PVAP), cellulose acetate phthalate (CAP), shellac, copolymers of methacrylic acid and ethyl acrylate, and copolymers of methacrylic acid and ethyl acrylate to which a monomer of methylacrylate has been added during polymerization; and optionally
(b) a pharmaceutically acceptable excipient.

In one embodiment of an oral vaccine formulation as described herein, the cores are prepared in the form of microparticulates having an average diameter of between about 1 nanometer to about 100 micrometers in diameter (as set forth in FIG. 5, for example).

In one embodiment of an oral vaccine formulation comprises a first and a second core population as described herein and as illustrated as in FIG. 5, for example, the cores of the first core population and the second core population are microparticulates, the average diameter of the cores of the first core population is greater than the average diameter of the cores of the second core population, the cores of the second core population have an average diameter of between about 1 nanometer to about 99 micrometers in diameter, and the cores of the first core population have an average diameter of between about 2 nanometer to about 100 micrometers.

The cores described herein can comprise an inert component, e.g. nonpareil beads or a biocompatible polymer as described hereinafter.

In another embodiment, the cores are nanoparticles and the mean diameter of the cores is between 0.5 and 100 nm, more preferably between 1 and 50 nm, and still more preferably between 1 and 20 nm. The mean diameter can be measured using techniques well known in the art such as transmission electron microscopy.

In still another embodiment, the invention provides methods of treating and/or preventing viral, pathogenic, parasitic, bacterial, vector-transmission associated, or cancer-related disorders by administering to a subject in need thereof a pharmaceutically effective amount of an oral vaccine formulation comprised of an appropriate antigen and as otherwise described herein.

For example, in one embodiment, the invention provides a method of eliciting an immune response to a viral, bacterial, parasitic, microbial, or cancer-associated antigen in a subject, the method comprising administering to the subject an oral vaccine formulation comprised of an appropriate antigen and as otherwise described herein.

In another embodiment, the invention provides a method of eliciting an immune response to a cancer-associated antigen in a subject, the method comprising co-administering to the subject an oral vaccine formulation comprised of an appropriate anti-cancer antigen as described herein and one or more heat shock proteins.

These and other aspects of the invention are described further in the Detailed Description of the Invention.

BRIEF DESCRIPTION OF THE FIGURES

FIG. 6 illustrates the two novel gastrointestinal dissolution sites of the vaccine pill within a vaccine pill.

DETAILED DESCRIPTION OF THE INVENTION

Figure 1:
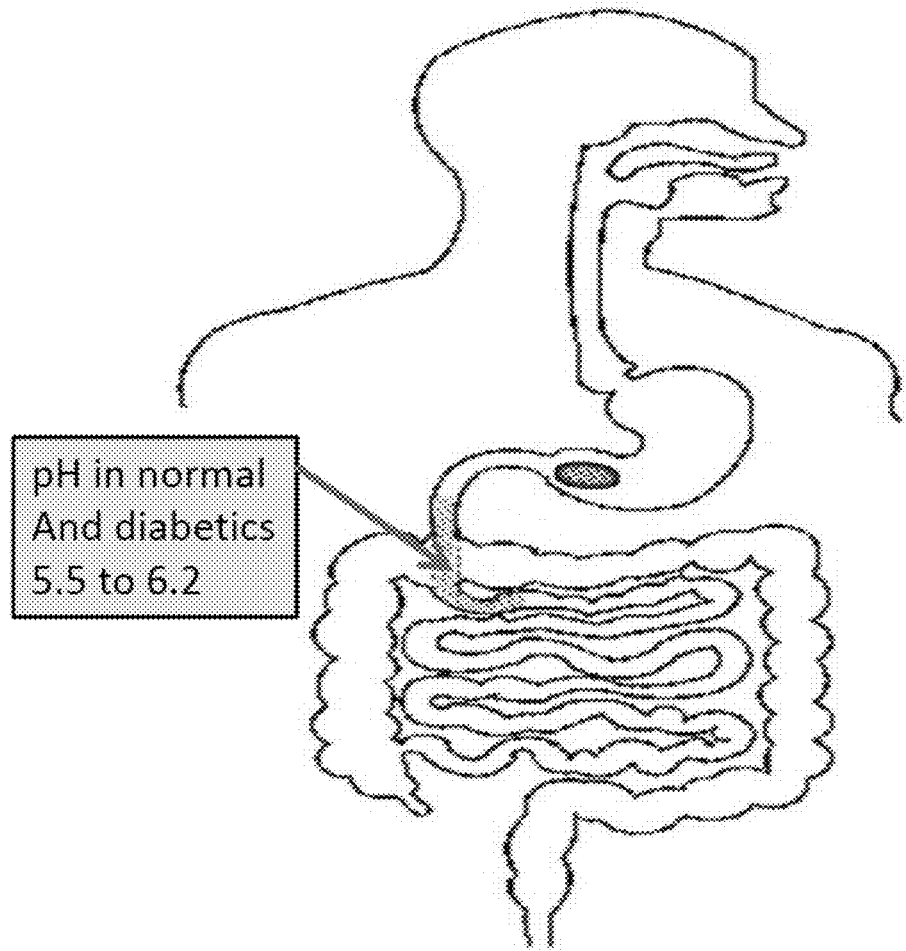
FIG. 1 is a schematic of conventional enteric release—duodenal target, which is proximal to the novel target for oral vaccination according to the present invention.

As used herein and in the appended claims, the singular forms "a," "an," and "the" include plural reference unless the context clearly dictates otherwise. Thus, for example, a reference to "a compound" or other element of the present invention includes a plurality (for example, two or more elements) of such elements, and so forth. Under no circumstances is the patent to be interpreted to be limited to the specific examples or embodiments or methods specifically disclosed herein.

The term "compound", as used herein, unless otherwise indicated, refers to any specific chemical compound, including an antigen disclosed herein and includes tautomers, regioisomers, geometric isomers, and where applicable, optical isomers thereof, as well as pharmaceutically acceptable salts thereof. Within its use in context, the term compound generally refers to a single compound, including an antigen, but also may include other compounds such as stereoisomers, regioisomers and/or optical isomers (including racemic mixtures) as well as specific enantiomers or enantiomerically enriched mixtures of disclosed compounds.

The term "antigen" or "immunogen" as used herein refers to any compound (e.g. peptide, carbohydrate, fragment of a cell, a microbe or a virus (often attenuated or inactive), or DNA or RNA fragment which may be used to elicit an immunogenic response in the appendix or ileum of a patient to whom the present compositions are administered. Note that DNA or RNA fragments are considered antigens in certain vaccine strategies or may be administered to express an antigen, each of which is otherwise defined as a compound herein.

The term "antigenic composition" refers to a composition which contains one or more antigens. Antigenic compositions are used to generate an immunogenic response in a patient or subject upon administration or introduction.

It is noted that the present invention contemplates the administration of antigenic compositions which comprise attenuated microbes (especially including bacteria) or viruses which are designed to elicit an immunogenic response without causing disease. Vaccine strains of attenuated microbes or viruses are inherently invasive species, in many cases highly virulent and can cause severe disease with even a small inocula as low as $10^3$.

Accordingly, vaccine strains of microbes, in particular bacteria, are never given in large amounts, preferably between about $10^2$ to about $5 \times 10^4$, or about $10^2$ to about $5 \times 10^3$ microbes per dose, even to non-sterile surfaces such as the human gastrointestinal tract, because of the likelihood that larger numbers would cause invasive disease and/or tissue damage. In addition, the bacteria strains which are used in the present invention are either inactive or attenuated. The use of attenuated microbes, including attenuated bacteria, to elicit an immunogenic response in a patient or subject stands in contrast to the use of a live bacteria, for example, a probiotic bacterial population which is administered to a subject for a completely different purposes and having substantially different features than the present invention. In the case of the administration of probiotic organisms, the organisms are live and vibrant and are administered in large numbers (up to about $10^{12}$ organisms or more) to repopulate the gastrointestinal tract of a patient or subject with the organisms. Thus, the nature of the organism and the number of organisms to be delivered in a replacement strategy such as used with probiotics stand in complete contrast to the use of microbes, including attenuated microbes, to elicit an immunogenic response pursuant to the present invention.

A preferred antigen may or may not contain an adjuvant substance, but in any case of application by those skilled in the art must demonstrate a sufficient protective response in the patient to which it is given.

The term "patient" or "subject" is used throughout the specification within context to describe an animal, generally a mammal, often including a domesticated animal (including farm animals), but or a laboratory test animal and preferably a human, to whom treatment, including prophylactic treatment, with the compositions and/or methods according to the present invention is provided. For treatment of a particular condition or disease state which is specific for a specific animal such as a human patient, the term patient refers to that specific animal.

The term "effective" is used herein, unless otherwise indicated, to describe an amount of a compound, composition or component and for an appropriate period of exposure time which, in context, is used to produce or effect an intended result, whether that result relates to eliciting an immunogenic response, elucidating a specific immune response to the administered antigen, or whether that result relates to the treatment or prevention/prophylaxis of a disorder or condition associated with the present invention or alternatively, is used to produce another compound, agent or composition. This term subsumes all other effective amount or effective concentration terms which are otherwise described in the present application.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

The term "nutritional substance" is used synonymously with "pharmaceutical composition" and "ileal brake hormone releasing substance" in certain contexts herein and refers to the substance which produces the intended effect in the ileum of a patient or subject pursuant to the present invention.

A "nutritional substance" includes, but is not limited to, proteins and associated amino acids, fats including saturated fats, monosaturated fats, polyunsaturated fats, essential fatty acids, Omega-3 and Omega-6 fatty acids, trans fatty acids, cholesterol, fat substitutes, carbohydrates such as dietary fiber (both soluble and insoluble fiber), starch, sugars (including monosaccharides, fructose, galactose, glucose, dextrose, disaccharides, lactose, maltose, sucrose, and alcohol), polymeric sugars including inulin and polydextrose, natural sugar substitutes (including brazzein, Curculin, erythritol, fructose, glycyrrhizin, glycyrrhizin, glycerol, hydrogenated starch hydrosylates, maltose, isomaltose, lactitol, mabinlin, maltitol, mannitol, miraculin, monellin, pentadin, sorbitol, stevia, tagatose, thaumatin, and xylitol), sahlep, and halwa root extract. D-glucose (dextrose) is a preferred nutritional substance. Nutritional substances include all compositions that yield the aforementioned nutrients upon digestion or that contain such nutrients, including polymeric forms of these nutrients.

Additional nutritional components which may be included in compositions according to the present invention include, barley grass, known to be a rich source of highly metabolizable vitamins and minerals such as vitamins A, B1, B2, B6, and C, potassium, magnesium, and zinc. In addition, barley grass also has a high concentration of the enzyme superoxide dismutase (SOD), which has been shown to have high levels of antioxidant activity. Barley Grass and derivatives are categorized as Generally Regarded as Safe (GRAS) by the FDA. Barley grass is believed to be an important nutrient in the regulation of the digestive process because the micronutrients, enzymes (e.g., SOD), and fiber contained in barley grass are believed to improve intestinal immune and repair functions.

Alfalfa fresh or dried leaf tea is also usable in the invention, to promote appetite, and as a good source of chlorophyll and fiber. Alfalfa contains biotin, calcium, choline, inositol, iron, magnesium, PABA, phosphorus, potassium, protein, sodium, sulfur, tryptophan (amino acid), and vitamins A, B complex, C, D, E, K, P, and U. Alfalfa supplements are recommended for treating poor digestion, and were shown to lower cholesterol levels in animal studies. Alfalfa is categorized as Generally Regarded as Safe (GRAS) by the FDA. Dosages can range from 25-1500 mg, preferably 500-1000 mg dried leaf per day.

*Chlorella* is yet another substance usable in the invention in combination with the nutritional substance (preferably D-glucose or dextrose), being a genus of unicellular green algae, grown and harvested in tanks, purified, processed and dried to form a powder. *Chlorella* is rich in chlorophyll, carotenes, and contains the full vitamin B complex, vitamins E and C, and has a wide range of minerals, including magnesium, potassium, iron and calcium. *Chlorella* also provides dietary fiber, nucleic acids, amino acids, enzymes, CGF (*Chlorella* Growth Factor) and other substances. Dosages can range from 300-1500 mg/day.

Chlorophyllin is yet another nutritional substance, being a known food additive and has been used as an alternative medicine. Chlorophyllin is a water-soluble, semi-synthetic sodium/copper derivative of chlorophyll, and the active ingredient in a number of internally-taken preparations intended to reduce odors associated with incontinence, colostomies and similar procedures, as well as body odor in general. It is also available as a topical preparation, purportedly useful for treatment and odor control of wounds, injuries, and other skin conditions, such as for radiation burns.

Sodium alginate may also be used as a nutritional substance, preferably in combination with D-glucose or dextrose.

The term "ileum" is used to describe the third (of three) portion of the small intestine just before the small intestine becomes the large intestine in the gastrointestinal tract. The ileum is the final section of the small intestine in most higher vertebrates, including mammals. The ileum follows the duodenum and jejunum in the small intestine, and is separated from the "Cecum" by the ileocecal valve (ICV). In humans, the ileum is about 2-4 meters long, and the pH usually ranges between 7 and 8 (neutral or slightly alkaline). The function of the ileum is mainly to absorb vitamin B12 bile salts and whatever products of digestion were not absorbed by the jejunum. The wall itself is made up of folds, each of which has many tiny finger-like projections known as "villi" on its surface. In turn, the epithelial cells which line these villi possess even larger numbers of microvilli. The areas within these villi contain the important components of the immune system called Peyer's Patches. The DNES (diffuse neuroendocrine system) cells that line the ileum contain lower amounts of the protease and carbohydrase enzymes (gastrin, secretin, cholecystokinin) responsible for the final stages of protein and carbohydrate digestion. These enzymes are present in the cytoplasm of the epithelial cells.

Delaying the release in vivo of the majority of the nutritional substance and/or antigen until the dosage form reaches the subject's ileum or appendix and right colon means: (1) that not less than around 50% by weight, not less than around 70% by weight, more preferably not less than around 80% by weight, and more preferably not less than around 90%, of the nutritional substance and/or antigen remains unreleased in vivo prior to the dosage form's arrival at a subject's ileum or appendix and right colon; and (2) that not less than around 50%, not less than around 70% by weight, more preferably not less than around 80% by weight, and more preferably not less than around 90%, of the nutritional substance is remains unreleased in vivo by the time when the dosage form enters the subject's ileum or appendix and right colon.

In preferred aspects of the invention this amount of nutritional substance is at least about 1 gram, at least about 2.5 grams, at least about 3 grams, at least about 5 grams, at least about 7.5 grams, preferably about 10 grams to about 12-12.5 grams or more (about 12.5 to about 20 grams, especially of polymeric materials such as polydextrose or those compounds of higher molecular weight) of the nutritional substance and in particular, glucose, is released within the small intestine in the ileum in order to stimulate ileum hormones and related hormones and effect an ancillary result associated with inducing satiety and/or influencing one or more of insulin resistance (decrease resistance), blood sugar (decrease in/stabilize glucose levels), leptin (increase), glucagon secretion (decrease), insulin release (decrease and/or stabilize release and/or levels), ileum hormone release (increase) or other hormone release, in particular, one or more of GLP-1, glicentin, C-terminally glycine-extended GLP-1 (7 37), (PG (78 108)); C-peptide, intervening peptide-2 (PG (111 122) amide); GLP-2 (PG (126 158), GRPP (PG (1 30)), oxyntomodulin (PG (33 69), and other peptide fractions to be isolated, PYY (1-36), PYY (3-36), cholecystokinin (CCK), gastrin, enteroglucagon, secretin, as well as leptin, IGF-1 and IGF-2, and preferably, one or more, two or more, three or more, four or more, five or more, six or more, seven or more, or all of GLP1, GLP2, C-peptide, PYY (1-36 and/or 3-36), glucagon, leptin, IGF-1 and IGF-2.

In the present invention all antigens, adjuvants and co-administered active ingredients are used in effective amounts to provide activity relevant to the use of the compound. For example, in combination therapy, a cancer antigen, an optional adjuvant and optional ileal brake hormone releasing agent are all used in effective amounts. The amount of such compositions used in the present invention may vary according to the nature of the composition, the age and weight of the patient and numerous other factors which may influence the bioavailability and pharmacokinetics of the composition, the amount of composition which is administered to a patient generally ranges from about 0.001 mg/kg to about 50 mg/kg or more, about 0.5 mg/kg to about 25 mg/kg, about 0.1 to about 15 mg/kg, about 1 mg to about 10 mg/kg per day and otherwise described herein. The person of ordinary skill may easily recognize variations in dosage schedules or amounts to be made during the course of therapy.

The term "ileum hormones" includes all hormones that are associated with intraluminal food substances stimulating the release of said hormones, could be associated with satiety feedback from the ileum or ileum-related stimulation of insulin secretion or inhibition of glucagon secretion. "Ileum hormones" therefore include, but are not limited to, GLP-1, glicentin, C-terminally glycine-extended GLP-1 (7 37), (PG (78 108)); intervening peptide-2 (PG (111 122) amide); GLP-2 (PG (126 158), GRPP (PG (1 30)), oxyntomodulin (PG (33 69), and other peptide fractions to be isolated, PYY (PYY 1-36) and (PYY 3-36), cholecystokinin (CCK), gastrin, enteroglucagon and secretin.

The term "ileum hormone-stimulating amount of a nutritional substance" or "ileal brake hormone releasing substance" means any amount of a nutritional substance that is effective to induce measurable hormone release in the ileum, particularly in certain aspects of the present invention the output of interferon (IFN) and reduction of endotoxin release. Many of the ileal brake hormones induce satiety in the patient by feedback from the ileum or ileum-related stimulation of insulin secretion or inhibition of glucagon secretion, or other effects such as shutting down or decreasing insulin resistance and increasing glucose tolerance. Consequently, an "ileum hormone-stimulating amount of a nutritional substance" can vary widely in dosage depending upon factors such as the specific nutrient at issue, the desired effect of administration, the desired goal of minimizing caloric intake, and the characteristics of the subject to whom the nutritional substance is administered. For example, at least about 500 mg of D-glucose is used, and a particularly preferred ileum hormonal-stimulating amount of D-glucose includes between about 7.5-8 g to about 12-12.5 g (preferably around 10 g).

Dosage forms used in methods of the invention can be in a form suitable for oral use, for example, as tablets, troches, lozenges, suspensions, micro-suspensions, dispersible powders or granules, emulsions, micro-emulsions, hard or soft capsules. Useful dosage forms include osmotic delivery systems as described in U.S. Pat. Nos. 4,256,108; 5,650,170 and 5,681,584, multi-particulate systems as disclosed in U.S. Pat. No. 4,193,985; systems in which the nutritional substance is coated with a mixed film of a hydrophobic organic compound-enteric polymer as disclosed in U.S. Pat. No. 6,638,534; systems such as those described in U.S. Pat. Nos. 7,081,239; 5,900,252; 5,603,953; and 5,573,779; enteric-coated dry emulsion formulations (e.g., *Journal of Controlled Release*, vol. 107, issue 1 20 Sep. 2005, Pages 91-96), and emulsions such as the emulsion system of Olibra® and those disclosed in U.S. Pat. No. 5,885,590. Those of ordinary skill in the prior art know how to formulate these various dosage forms and modify these forms such that they release the majority of their nutritional substance in a subject's ileum or duodenum as otherwise described herein by adjusting the solubility and pH release characteristics of the dosage forms once the present invention becomes known to them.

Exemplary dosage forms that will release the majority of the nutritional substance in vivo upon reaching the ileum include oral dosage forms such as tablets, troches, lozenges, dispersible powders or granules, or a hard or soft capsules which are formed by coating the nutritional substance with an enteric coating (e.g., an enteric cellulose derivative, an enteric acrylic copolymer, an enteric maleic copolymer, an enteric polyvinyl derivative, or shellac). Preferred enteric coatings have a pH dissolution profile that delays the release in vivo of the majority of the nutritional substance until the dosage form reaches the ileum. Enteric coatings can consist of a single composition, or can comprise two or more compositions, e.g., two or more polymers or hydrophobic organic compound-enteric polymer compositions as described in U.S. Pat. No. 6,638,534).

A material having a pH dissolution profile that delays release in vivo of the majority of the nutritional substance and/or antigen until the dosage form reaches the ileum, distal ileum or colon in the vicinity of the appendix includes but is not limited to cellulose acetate trimellitiate (CAT), hydroxypropylmethyl cellulose phthalate (HPMCP), polyvinyl acetate phthalate (PVAP), cellulose acetate phthalate (CAP), shellac, copolymers of methacrylic acid and ethyl acrylate, copolymers of methacrylic acid and ethyl acrylate to which a monomer of methylacrylate has been added during polymerization, a mixture of amylose-butan-1-ol complex (glassy amylose) with Ethocel® aqueous dispersion (Milojevic et al., Proc. Int. Symp. Contr. Rel. Bioact. Mater. 20, 288, 1993), a coating formulation comprising an inner coating of glassy amylose and an outer coating of cellulose or acrylic polymer material (Allwood et al. GB 9025373.3), calcium pectinate (Rubenstein et al., Pharm. Res., 10, 258, 1993) pectin, chondroitin sulphate (Rubenstein et al. Pharm. Res. 9, 276, 1992), resistant starches (PCT WO 89/11269), dextran hydrogels (Hovgaard, et al., 3rd Eur. Symp. Control. Drug Del., Abstract Book, 1994, 87) modified guar gum such as borax modified guar gum, (Rubenstein and Gliko-Kabir, S. T. P. Pharma Sciences 5, 41-46, 1995), beta.-cyclodextrin (Sidke et al., Eu. J. Pharm. Biopharm. 40 (suppl), 335, 1994), saccharide containing polymers, e.g., a polymeric construct comprising a synthetic oligosaccharide-containing biopolymer including methacrylic polymers covalently coupled to oligosaccharides such as cellobiose, lactulose, raffinose and stachyose, or saccharide-containing, natural polymers including modified mucopolysaccharides such as cross-linked pectate (Sintov and Rubenstein PCT/US 91/03014); methacrylate-galactomannan (Lehmann and Dreher, Proc. Int. Symp. Control. Rel. Bioact. Mater. 18, 331, 1991) and pH-sensitive hydrogels (Kopecek et al., J. Control. Rel. 19, 121, 1992), and resistant starches, e.g., glassy amylose.

Methylmethacrylates or copolymers of methacrylic acid and methylmethacrylate are preferred materials having a pH dissolution profile that delays release in vivo of the majority of the antigen until the dosage form reaches the appendix and/or right colon. Such materials are available as Eudragit® polymers (Rohm Pharma, Darmstadt, Germany). For example, Eudragit® L100 and Eudragit® S100 can be used, either alone or in combination. Eudragit® L100 dissolves at pH 6 and upwards and comprises 48.3% methacrylic acid units per g dry substance; Eudragit® S100 dissolves at pH 7 and upwards and comprises 29.2% methacrylic acid units per g dry substance. Generally, the encapsulating polymer has a polymeric backbone and acid or other solubilizing functional groups. Polymers which have been found suitable for purposes of the present invention include polyacrylates, cyclic acrylate polymer, polyacrylic acids and polyacrylamides. Another preferred group of encapsulating polymers are the polyacrylic acids Eudragit® L and Eudragit® S which optionally may be combined with Eudragit® RL or RS. These modified acrylic acids are useful since they can be made soluble at a pH of 6 or 7.5, depending on the particular Eudragit chosen, and on the proportion of Eudragit® S to Eudragit® L, RS, and RL used in the formulation. By combining one or both of Eudragit® L and Eudragit® S with Eudragit® RL and RS (5-25%), it is possible to obtain a stronger capsule wall and still retain the capsule's pH-dependent solubility. In additional preferred aspects of the invention, a coating of shellac (which also includes one or more emulsifiers such as hypromellose and/or triacetin) which is chosen to have a suitable pH-dependent dissolution profile for release the contents of a dosage form such as a tablet within the ileum of a patient or subject may be used. This type of coating provides a nutrateric approach to delayed and/or controlled release using naturally occurring, non-synthetic components.

In some embodiments, the coating profile that delays release in vivo of the majority of the antigen until the dosage form reaches the appendix and/or right colon comprises Eudragit® L100 and shellac or food/pharmaceutical glaze, Eudragit® S100 in the range of 100 parts L100:0 parts S100 to 20 parts L100:80 parts S100, more preferably 70 parts L100:30 parts S100 to 80 parts L100:20 parts S100. As the pH at which the coating begins to dissolve increases, the thickness necessary to achieve ileum-specific delivery decreases. For formulations where the ratio of Eudragit® L100:S100 is high, a coat thickness of the order 150-200 µm can be used. For coatings where the ratio of Eudragit® L100:S100 is low, a coat thickness of the order 80-120 µm can be used. Dosage forms used in methods of the invention can include one or more pharmaceutically acceptable carriers, additives, or excipients.

The term "pharmaceutically acceptable" refers to a carrier, additive or excipient which is not unacceptably toxic to the subject to which it is administered. Pharmaceutically acceptable excipients are described at length by E. W. Martin, in "Remington's Pharmaceutical Sciences", among others well-known in the art. pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Emulsions and micro-emulsions may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the nutritional substance, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Techniques for formulating the aforementioned useful dosage forms are either disclosed in the references cited above or are well-known to those of ordinary skill in the art. The vaccine pill in a vaccine pill dosage form as exemplified in FIGS. 5-6 or as modified is a particularly preferred dosage form that is useful in the methods of treatment of the invention.

"Biocompatible polymer" as used herein is intended to describe polymers that are not toxic to cells. Compounds are "biocompatible" if their addition to cells in vitro results in less than or equal to 20% cell death and if they do not induce significant inflammation or other such significant adverse effects in vivo.

Biocompatible polymers can be categorized as biodegradable and non-biodegradable. Biodegradable polymers degrade in vivo as a function of chemical composition, method of manufacture, and implant structure. Synthetic and natural polymers can be used although synthetic polymers are preferred due to more uniform and reproducible degradation and other physical properties. Examples of synthetic polymers include polyanhydrides, polyhydroxyacids such as polylactic acid, polyglycolic acids and copolymers thereof, polyesters, polyamides, polyorthoesters, and some polyphosphazenes. Examples of naturally occurring polymers include proteins and polysaccharides such as collagen, hyaluronic acid, albumin and gelatin. Antigen and/or drug can be encapsulated within, throughout, and/or on the surface of the implant. Antigen and/or drug is released by diffusion, degradation of the polymer, or a combination thereof. There are two general classes of biodegradable polymers: those degrading by bulk erosion and those degrading by surface erosion. U.S. patents that describe the use of polyanhydrides for controlled delivery of substances include U.S. Pat. No. 4,857,311 to Domb and Langer, U.S. Pat. No. 4,888,176 to Langer, et al., and U.S. Pat. No. 4,789,724 to Domb and Langer.

Other polymers such as polylactic acid, polyglycolic acid, and copolymers thereof have been commercially available as suture materials for a number of years and can be readily formed into devices for drug delivery.

Non-biodegradable polymers remain intact in vivo for extended periods of time (e.g., at least about one or more years). Antigen and/or drug loaded into the non-biodegradable polymer matrix is released by diffusion through the polymer's micropore lattice in a sustained and predictable fashion, which can be tailored to provide a rapid or a slower release rate by altering the percent drug loading, porosity of the matrix, and implant structure. Ethylene-vinyl acetate copolymer (EVAc) is an example of a nonbiodegradable polymer that has been used as a local delivery system for proteins and other micromolecules, as reported by Langer, R., and J. Folkman, Nature (London) 263:797-799 (1976). Others include polyurethanes, polyacrylonitriles, and some polyphosphazenes.

Cationic polymers have been widely used as transfection vectors due to the facility with which they condense and protect negatively charged strands of DNA. Amine-containing polymers such as poly(lysine) (Zauner et al., Adv. Drug Del. Rev., 30:97-113, 1998; Kabanov et al., Bioconjugate Chem., 6:7-20, 1995, the entire teachings of each of the foregoing references are incorporated herein by reference), poly(ethylene imine) (PEI) (Boussif et al., Proc. Natl. Acad. Sci. USA, 92:7297-7301, 1995, the entire teachings of which are incorporated herein by reference), and poly(amidoamine) dendrimers (Kukowska-Latallo et al., Proc. Natl. Acad. Sci. USA, 93:4897-4902, 1996; Tang et al., Bioconjugate Chem. 7:703-714, 1996; Haensler et al., Bioconjugate Chem., 4:372-379, 1993; the entire teachings of each of the foregoing references are incorporated herein by reference) are positively-charged at physiological pH, form ion pairs with nucleic acids, and mediate transfection in a variety of cell lines.

Degradable polyesters bearing cationic side chains have also been developed (Putnam et al., Macromolecules, 32:3658-3662, 1999; Barrera et al., J. Am. Chem. Soc., 115:11010-11011, 1993; Kwon et al., Macromolecules, 22:3250-3255, 1989; Lim et al., J. Am. Chem. Soc., 121: 5633-5639, 1999; Zhou et al., Macromolecules, 23:3399-3406, 1990, the entire teachings of each of the foregoing references are incorporated herein by reference). Examples of these polyesters include poly(L-lactide-co-L-lysine) (Barrera et al., J. Am. Chem. Soc., 115:11010-11011, 1993; the entire teachings of which are incorporated herein by reference), poly(serine ester) (Zhou et al., Macromolecules, 23:3399-3406, 1990, the entire teaching of each of the foregoing references are incorporated herein by reference), poly(4-hydroxy-L-proline ester) (Putnam et al., Macromolecules, 32:3658-3662, 1999; Lim et al., J. Am. Chem. Soc., 121:5633-5639, 1999, the entire teachings of each of the foregoing references are incorporated herein by reference). Poly(4-hydroxy-L-proline ester) was recently demonstrated to condense plasmid DNA through electrostatic interactions, and to mediate gene transfer (Putnam et al., Macromolecules, 32:3658-3662, 1999; Lim et al., J. Am. Chem. Soc., 121:5633-5639, 1999, the entire teachings of each of the foregoing references are incorporated herein by reference). Importantly, these new polymers are significantly less toxic than poly(lysine) and PEI, and they degrade into non-toxic metabolites.

Enteric coatings can be applied by conventional coating techniques, such as pan coating or fluid bed coating, using solutions of polymers in water or suitable organic solvents or by using aqueous polymer dispersions. As an alternative embodiment, the release controlling enteric coating can separate additional antigen and/or drug layers on the core; for instance, after coating with the release controlling substance, another antigen and/or drug layer can be applied, which is followed by another release controlling layer, etc. For example, suitable materials for the release controlling layer include EUDRAGIT® (copolymers of acrylic and methacrylic acid esters), EUDRAGIT®RS (copolymers of acrylic and methacrylic acid esters), cellulose derivatives such as ethylcellulose aqueous dispersions (AQUACOAT®, SURELEASE®), hydroxyethyl cellulose, hydroxypropyl cellulose, hydroxypropyl methylcellulose, polyvinylpyrrolidone, polyvinylpyrrolidone/vinyl acetate copolymer, OPADRY®, and the like.

The thickness of the coating affects the release profile in the jejunum and ileum, and so this parameter can be used to customize the profile. The suggested coating levels are from about 1% to about 5%, preferably about 5% to about 10% (w/w), and about 6% or about 8% as most preferred embodiments. An 8% w/w coating should release about 80% of the antigen and/or drug in 3-3.5 hours post ingestion, and a 6% w/w coating should result in the release of about 80% of the antigen and/or drug in 2.8-3.2 hours post-ingestion. Often, in many aspects of the invention, the target coating thickness between 6-10% by weight, and target time of absorption is as long as 3.5 hrs The methods described herein may also comprise the administration of one or more other therapeutic agents or drugs, including without limitation anti-viral, anti-bacterial agents, anti-fungal agents, anti-cancer and anti-microbial agents. For purposes of the present invention, the terms therapeutic agents or drugs are not intended to embrace live organisms such as probiotic bacteria and such an interpretation is specifically excluded herein.

Examples of anti-viral agents include, without limitation, reverse transcriptase inhibitors such as, for example, zidovudine, didanosine, zalcitabine, stavudine, lamivudine, abacavir, nevirapine, delavirdine, and efavirenz; protease inhibitors such as, for example, saquinavir, ritonavir, nelfinavir, indinavir, amprenavir, and lopinavir; agents for treating herpes viruses such as, for example, acyclovir, valacyclovir, valacyclovir, famciclovir, ganciclovir, foscarnet, and cidolovir; and, agents for treating influenza such as, for example, oseltamivir, amantadine, rimatadine, and zanamivir. Examples of anti-bacterial agents include, without limitation, penicillins, cephalosporins, quinolones, tetracyclines, macrolides. Examples of anti-fungal agents include, without limitation, amphotericin B, fluconazole, voriconazole and the like.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascetic and solid tumors.

One promising approach for utilizing the present invention is to incorporate already characterized cancer antigens (1-10) and deliver them to the ileum and appendix to enhance the resulting immune response. Specific antigens are disclosed in the examples, which are presented in the present specification, but are not meant to be limiting, as the formulation disclosed herein may be readily adapted to any existing or newly discovered tumor antigen by one skilled in the art.

Tumor antigens recognized by autologous CD8+ T cells and/or antibodies have been classified into one or more of the following categories a) differentiation antigens e.g. tyrosinase, Melan-A/MART-1, gp100; b) mutational antigens e.g. CDK4, beta-catenin, caspase-8, and P53; c) amplification antigens e.g. Her2/neu and P53, d) splice variant antigens e.g. NY-CO-37/PDZ-45 and ING1; e) viral antigens e.g. human papilloma virus and EBV; and f) CT antigens e.g. MAGE, NY-ESO-1 and LAGE-1. (7) The CT antigens are a distinct and unique class of differentiation antigens. The defining characteristics of these antigens are the high levels of expression in adult male germ cells, but generally not in other normal adult tissues, and aberrant expression in a variable proportion of a wide range of different cancer types.

Formulations and methods of the invention, in addition to instilling immunogenicity and/or immunity against infection, also can be used for "immunotherapy" to treat a cancerous disease state, in particular, a drug resistant cancer, a multiple drug resistant cancer, a leukemia or related hematopoietic cancer, including T-ALL and related leukemias, especially drug resistant (multiple) leukemias, such as T-ALL, and numerous cancerous tumors as otherwise described herein. These diseases may include any one or more of hematopoietic neoplasms and metastasis of such neoplasms, including Hodgkin's disease, non-Hodgkin's lymphoma, leukemias, including non-acute and acute leukemias, such as acute myelogenous leukemia, acute lymphocytic leukemia, acute promyelocytic leukemia (APL), acute T-cell lymphoblastic leukemia, T-lineage acute lymphoblastic leukemia (T-ALL), adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia. Other cancers, including cancerous tumors, which may be treated using the present invention include for example, stomach (especially including gastric stromal cells), colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, skin cancer, including melanoma and non-melanoma, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others. Additional cancers which may be particularly responsive to therapeutic methods according to the present invention include for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML, breast cancer, Ewing's sarcoma, osteosarcoma and undifferentiated high-grade sarcomas, among others.

The term "neoplasia" or "neoplasm" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and may invade surrounding tissues. As used herein, the term neoplasia/neoplasm is used to describe all cancerous disease states and embraces or encompasses the pathological process associated with cancer, including hematopoietic cancers, numerous cancerous tumors and their metastasis.

A "hematopoietic neoplasm" or "hematopoietic cancer" is a neoplasm or cancer of hematopoeitic cells of the blood or lymph system and includes disease states such as Hodgkin's disease, non-Hodgkin's lymphoma, leukemias, including non-acute and acute leukemias, such as acute myelogenous leukemia, acute lymphocytic leukemia, acute promyelocytic leukemia (APL), adult T-cell leukemia, T-lineage acute lymphoblastic leukemia (T-ALL), basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia, among others.

The term "prophylactic" is used in the context of this disclosure with a similar meaning as "providing an immunogenic response" or alternatively, "vaccinating" is used to describe the use of a compound described herein which reduces the likelihood of an occurrence of a condition or disease state in a patient or subject. The term "reducing the likelihood" refers to the fact that in a given population of patients, the present invention may be used to reduce the likelihood of an occurrence, recurrence or metastasis of disease in one or more patients within that population of all patients, rather than prevent, in all patients, the occurrence, recurrence or metastasis of a disease state.

In certain aspects according to the present invention, where various cancers are to be treated, the formulations may be co-administered with at least one other anti-cancer agent such as antimetabolites, Ara C, etoposide, doxorubicin, taxol, hydroxyurea, vincristine, cytoxan (cyclophosphamide) or mitomycin C, among numerous others, including topoisomerase I and topoisomerase II inhibitors, such as adriamycin, topotecan, campothecin and irinotecan, other agent such as gemcitabine and agents based upon campothecin and cisplatin. By "co-administer" it is meant that the present compounds are administered to a patient such that the present compounds as well as the co-administered compound may be found in the patient's bloodstream at the same time, regardless when the compounds are actually administered, including simultaneously. In many instances, the co-administration of the present compounds with traditional anticancer agents produces a synergistic (i.e., more than additive) result which is unexpected.

Additional compounds which may be used in combination with the formulations of the present invention include for example: adriamycin, anastrozole, arsenic trioxide, asparaginase, azacytidine, BCG Live, bevacizumab, bexarotene capsules, bexarotene gel, bleomycin, bortezombi, busulfan intravenous, busulfan oral, calusterone, campothecin, capecitabine, carboplatin, carmustine, carmustine with polifeprosan 20 implant, celecoxib, cetuximab, chlorambucil, cisplatin, cladribine, clofarabine, cyclophosphamide, cytarabine, cytoxan, cytarabine liposomal, dacarbazine, dactinomycin, actinomycin D, dalteparin sodium, darbepoetin alfa, dasatinib, daunorubicin liposomal, daunorubicin, daunomycin, decitabine, denileukin, denileukin diftitox, dexrazoxane, dexrazoxane, docetaxel, doxorubicin, doxorubicin liposomal, dromostanolone propionate, eculizumab, Elliott's B Solution, epirubicin, epirubicin hcl, epoetin alfa, erlotinib, estramustine, etoposide phosphate, etoposide VP-16, exemestane, fentanyl citrate, filgrastim, floxuridine (intraarterial), fludarabine, fluorouracil 5-FU, fulvestrant, gefitinib, gemcitabine, gemcitabine hcl, gemcitabine, gemtuzumab ozogamicin, gleevac, goserelin acetate, goserelin acetate, histrelin acetate, hydroxyurea, ibritumomab tiuxetan, idarubicin, ifosfamide, imatinib mesylate, interferon alfa 2a, interferon alfa-2b, irinotecan, irinotecan-PEG, lapatinib ditosylate, lenalidomide, letrozole, leucovorin, leuprolide acetate, levamisole, lomustine CCNU, meclorethamine, nitrogen mustard, megestrol acetate, melphalan L-PAM, mercaptopurine 6-MP, mesna, methotrexate, methoxsalen, mitomycin C, mitotane, mitoxantrone, nandrolone phenpropionate, nelarabine, nofetumomab, oprelvekin, oxaliplatin, paclitaxel, paclitaxel protein-bound particles, palifermin, pamidronate, panitumumab, pegademase, pegaspargase, pegfilgrastim, peginterferon alfa-2b, pemetrexed disodium, pentostatin, pipobroman, plicamycin, mithramycin, porfimer sodium, procarbazine, quinacrine, rasburicase, rituximab, sargramostim, sorafenib, streptozocin, sunitinib, sunitinib maleate, talc, tamoxifen, temozolomide, teniposide VM-26, testolactone, thalidomide, thioguanine 6-TG, thiotepa, topotecan, topotecan hcl, toremifene, tositumomab, tositumomab/I-131 tositumomab, trastuzumab, tretinoin ATRA, uracil mustard, valrubicin, vinblastine, vincristine, vinorelbine, vorinostat, zoledronate, zoledronic acid and mixtures thereof.

As described herein, other diseases that can be treated or vaccinated against using formulations of the invention include, without limitation, any infection and the diseases caused by infections. In one embodiment, the infection is an acute infection. In one embodiment, the infection is a bacterial infection. In another embodiment, the infection is a viral infection. In another embodiment, the infection is a fungal infection. In one embodiment, the disease is sepsis. In another embodiment, the disease is an infection that leads to a respiratory disease (or a respiratory disease resulting from an infection), including without limitation, infections and diseases caused by gram positive and gram negative bacteria, mycobacteria (such as *mycobacterium tuberculosis*), fungal infections (e.g., infections of *Pneumocystis, Candida*, and *Histoplasma*) and viral infections (e.g., infections of influenza, varicella, and corona virus such as SARS-associated coronavirus). In another embodiment, the disease is meningitis. In another embodiment, the disease is influenza. In one embodiment, the disease is pneumonia (regardless of whether it is caused by a bacterial, viral or fungal infection). In a specific embodiment, the pneumonia is Community Acquired Pneumonia (CAP). In one embodiment, the viral infection is a retroviral infection. In one embodiment, the retroviral infection is HIV infection. In another embodiment, the infection is Hepatitis of any variety, including A, B, C or other. In another embodiment, the disease associated is associated with low MIF expression and is infection by a virus or other pathogen that use the CCR5 receptor for infection, including, without limitation, HIV-1, HCV, CMV, Epstein-Barr Virus, and *Yersinia pestis*.

Formulations of the invention can also be administered in combination with a tumor necrosis factor-α (TNFα) antagonist or an interferon (IFN) antagonist (e.g., an IFNγ antagonist) to a subject. Examples of TNFα and IFNγ antagonists include, without limitation, anti-TNF, soluble TNF receptor, anti-IFNγ, soluble IFNγ receptor, p38 MAPK inhibitors, and JAK-STAT inhibitors.

Thus, formulations of the invention can treat and/or prevent, e.g., viral infections (including retroviral infections), bacterial infections, fungal infections, infections leading to respiratory disease, infections with HIV, infections with CMV, infections with Hepatitis viruses (especially A B or C), pneumonia, Community Acquired Pneumonia (CAP), meningitis, and influenza. In certain embodiments, a formulation of the invention is used to treat and/or prevent pathogenic infections during acute stages of infection, including during a flare-up of the infection, during a change of therapy, when signs of resistance to therapy are displayed in the subject, or as an early intervention.

In one embodiment, the invention provides a method of treating and/or preventing an infection that leads to a respiratory disease comprising administering to a subject a therapeutically effective amount of a formulation of the invention. Infections that lead or may lead to respiratory disease include, without limitation, infections by gram positive and gram negative bacteria, mycobacteria (such as *mycobacte-*

*rium tuberculosis*), fungal infections (e.g., infections of *Pneumocystis, Candida,* and *Histoplasma*) and viral infections (e.g., infections of influenza, varicella, and corona virus such as SARS-associated coronavirus).

The invention also provides a method of treating and/or preventing a respiratory disease resulting from an infection comprising administering to a subject a therapeutically effective amount of a formulation of the invention.

In certain embodiments, the invention provides a method of treating and/or preventing pneumonia in a subject comprising administering to the subject a therapeutically effective amount of a formulation of the invention. Microbial infections that lead to pneumonia include, without limitation, bacterial infections (e.g., infections of gram positive bacteria, gram negative bacteria, and mycobacteria such as *mycobacterium tuberculosis*), fungal infections (e.g., infections of *Pneumocystis, Candida,* and *Histoplasma*) and viral infections (e.g., infections of influenza, varicella, and corona virus such as SARS-associated coronavirus).

In certain embodiments, the invention provides a method of treating and/or preventing a retroviral infection comprising administering to a subject a therapeutically effective amount of a formulation of the invention.

In certain embodiments, the invention provides a method of treating and/or preventing HIV infection comprising administering to a subject a therapeutically effective amount of a formulation of the invention.

The invention also comprises the use of a formulation of the invention as an immunoadjuvant, also simply termed an adjuvant. Examples of adjuvants that have been employed in vaccines available include, but are not limited to the following: Alum, Aluminum phosphate, aluminum hydroxide, polysorbate 80, virosomes in particular to enhance the response to influenza and hepatitis vaccines, squalene, Freund's adjuvant, the AS03 adjuvant system, which is an oil in water emulsion containing Vitamin E, squalene, and polysorbate 80. This is often used for influenza vaccines Bacterial endotoxin or Lipopolysaccharide or derivatives thereof is often used as an adjuvant for cancer vaccines; DNA vaccines with Adenoviral vectors are highly immunogenic against Hepatitis C viruses in testing thus far.

Again, the methods described herein may also comprise the administration of one or more other therapeutic agents, including without limitation anti-bacterial agents, anti-fungal agents and anti-microbial agents. Additional examples of anti-viral agents include, without limitation, reverse transcriptase inhibitors such as, for example, zidovudine, didanosine, zalcitabine, stavudine, lamivudine, abacavir, nevirapine, delavirdine, and efavirenz; protease inhibitors such as, for example, saquinavir, ritonavir, nelfinavir, indinavir, amprenavir, and lopinavir; agents for treating herpes viruses such as, for example, acyclovir, valacyclovir, valacyclovir, famciclovir, ganciclovir, foscarnet, and cidolovir; and, agents for treating influenza such as, for example, oseltamivir, amantadine, rimatadine, and zanamivir. Examples of anti-bacterial agents include, without limitation, penicillins, cephalosporins, quinolones, tetracyclines, macrolides. Examples of anti-fungal agents include, without limitation, amphotericin, fluconazole.

In another embodiment, the invention provides a method of inhibiting the life-cycle of a virus in a subject infected with said virus or at risk of being infected with said virus comprising administering to the subject a formulation of the invention. In one embodiment, the pathogen is HIV-1.

As used herein the "inhibiting the life cycle of a virus" includes, inhibiting viral replication, inhibiting viral infection, latency and oncogenesis.

In a specific embodiment, the invention provides a method of treating or preventing HIV (HIV 1 or 2) infection in a subject infected or at risk of being infected with HIV, comprising administering to the subject a formulation of the invention. In certain embodiments, the antigen is gp120 or gp41 or the entire trimeric structure of the HIV virus, or virus-like particles (VLPs). A small proportion of HIV-infected individuals generate a neutralizing antibody (NAb) response of exceptional magnitude and breadth. A detailed analysis of the critical epitopes targeted by broadly neutralizing antibodies should help to define optimal targets for vaccine design. HIV-1-infected subjects with potent cross-reactive serum neutralizing antibodies were identified by assaying sera from 308 subjects against a multiclade panel of 12 "tier 2" viruses (4 each of subtypes A, B, and C). Various neutralizing epitope specificities were determined for the top 9 neutralizers, including clade A-, clade B-, clade C-, and clade A/C-infected donors, by using a comprehensive set of assays. In some subjects, neutralization breadth was mediated by two or more antibody specificities. Although antibodies to the gp41 membrane-proximal external region (MPER) were identified in some subjects, the subjects with the greatest neutralization breadth targeted gp 120 epitopes, including the CD4 binding site, a glycan-containing quaternary epitope formed by the V2 and V3 loops, or an outer domain epitope containing a glycan at residue N332. The broadly reactive HIV-1 neutralization observed in some subjects is mediated by antibodies targeting several conserved regions on the HIV-1 envelope glycoprotein. (11, 12). The HIV virus has many strategies to evade the T cell mediated immune response and even the humoral B cell response to its invasion, (13-19) and these pathways are well known to those skilled in the art. They are incorporated herein by reference.

In certain embodiments, a formulation of the invention is administered to a subject during acute HIV infection or during a flare-up. These methods may also comprise the administration of one or more other therapeutic agents. In one embodiment, the methods described herein comprise the administration of a formulation of the invention in combination with anti-viral agents. Examples of anti-viral agents include, without limitation, reverse transcriptase inhibitors such as, for example, zidovudine, didanosine, zalcitabine, stavudine, lamivudine, abacavir, nevirapine, delavirdine, and efavirenz; protease inhibitors such as, for example, saquinavir, ritonavir, nelfinavir, indinavir, amprenavir, and lopinavir; agents for treating herpes viruses such as, for example, acyclovir, valacyclovir, valacyclovir, famciclovir, ganciclovir, foscarnet, and cidolovir; and, agents for treating influenza such as, for example, oseltamivir, amantadine, rimatadine, and zanamivir.

In another aspect, the invention provides a method of treating or preventing HIV infection in a subject comprising administering to the subject a therapeutically effective amount of a formulation of the invention. In one embodiment, the HIV infection is at an acute stage. In one embodiment, the method further comprises administering to the subject another anti-viral agent.

In a specific embodiment, the invention provides a method of treating and/or preventing Hepatitis infections most typically Hepatitis B or Hepatitis C in a subject infected or at risk of being infected with Hepatitis B or C, comprising administering to the subject a formulation of the invention which delivers the medicament to the ileum and/or the appendix of the patient.

The term "Hepatitis C Virus" or "HCV" is used to describe the various strains of Hepatitis C virus. HCV is one of several viruses that can cause hepatitis. It is unrelated to the other common hepatitis viruses (for example, hepatitis A or hepatitis B, among others). HCV is a member of the Flaviviridae family of viruses. Other members of this family of viruses include those that cause yellow fever and dengue. Viruses belonging to this family all have ribonucleic acid (RNA) as their genetic material. All hepatitis C viruses are made up of an outer coat (envelope) and contain enzymes and proteins that allow the virus to reproduce within the cells of the body, in particular, the cells of the liver. Although this basic structure is common to all hepatitis C viruses, there are at least six distinctly different strains of the virus which have different genetic profiles (genotypes). Treatment of HCV according to the present invention is directed to all strains of HCV, including the six or more distinct strains described above, as well as related strains which are drug resistant and multiple drug resistant strains. In the U.S., genotype 1 is the most common form of HCV. Even within a single genotype there may be some variations (genotype 1a and 1b, for example). Genotyping is viewed as important to guide treatment because some viral genotypes respond better to therapy than others. HCV genetic diversity is one reason that it has been difficult to develop an effective vaccine since the vaccine must protect against all genotypes.

A "Hepatitis C virus infection" or "Hepatitis C infection" is an infection of the liver caused by the hepatitis C virus (HCV).

In certain embodiments, a formulation of the invention is administered to a subject during acute Hepatitis C infection (weeks 12 to week 42) or during a flare-up. (20) Raghuraman and colleagues examined the time course of hepatitis C and its interaction with the cells of the host immune system. They noted that Hepatitis C virus readily establishes chronic infection with exhaustion of HCV-specific T cells and escape from neutralizing antibodies. Spontaneous recovery from chronic infection is rare and has been incompletely studied in the past. They prospectively studied, from prior to infection through >2 years of follow-up, cytokines, HCV-specific T cells, and antibodies, as well as viral sequence evolution in a white male who spontaneously cleared HCV genotype 1a after 65 weeks. Significant alanine aminotransferase and plasma cytokine elevation and broad HCV-specific T-cell responses of CD4 and CD8 T cells did not result in HCV clearance in the acute phase. Frequency and effector function of HCV-specific T cells decreased thereafter, and HCV titers stabilized as is typical for the chronic phase. HCV clearance after 65 weeks followed the appearance of neutralizing antibodies at week 48 and was associated with reversal of HCV-specific T-cell exhaustion, as evidenced by reduced programmed death-1 (PD-1) expression and improved T-cell function. Clearance occurred without inflammation or superinfection with hepatitis B virus, human cytomegalovirus virus, influenza, and Epstein-Barr virus. They concluded that T-cell exhaustion is reversible at least in the first 2 years of chronic HCV infection, and this reversion in conjunction with neutralizing antibodies may clear HCV (20). They did note that Hepatitis C does not typically clear spontaneously, and attributed the T cell defects to impairment of recognition and to T cell exhaustion, among others. The fact that a significant proportion of infected people spontaneously control HCV infection in the setting of an appropriate immune response suggests that a vaccine for HCV is a realistic goal. (21) A comparative analysis of infected people with distinct clinical outcomes has enabled the characterization of many important innate and adaptive immune processes associated with viral control. It is clear that a successful HCV vaccine will need to exploit and enhance these natural immune defense mechanisms. New HCV vaccine approaches, including peptide, recombinant protein, DNA and vector-based vaccines, have recently reached Phase I/II human clinical trials. Some of these technologies have generated robust antiviral immunity in healthy volunteers and infected patients.

The role of Interferon IFN is still under intense study; clearly, this cytokine, a product of activated $CD8^+$ T cells (absent during T cell exhaustion) has antiviral properties as well as readily inhibiting Hepatitis C replication in hepatoma cells. (21). Clearly these findings justify the continued use of IFN products as part of overall drug treatment strategies for Hepatitis C. It is also clear that many oral regimens that are being used without additional IFN are unable to completely clear the Hepatitis C virus (22). It has been postulated by Grafmueller that IL-17 has a role similar to that of IFN in Hepatitis C as well as in HIV. She found that a subset of CD8(+) T cells can secrete interleukin 17 (IL-17). To address the issues of antigen specificity, tissue distribution and biological relevance, she comprehensively analyzed peripheral and intrahepatic CD8(+) T-cell responses in a cohort of patients with chronic hepatitis C virus (HCV) infection for the antigen-specific production of IL-17 and interferon (IFN) gamma. HCV-specific IL-17-producing and retinoic acid receptor related orphan receptorgammat-expressing CD8(+) T cells were detectable in blood and liver and target different epitopes, compared with IFN-gamma-producing CD8(+) T cells. Their highest frequency was found in patients with low inflammatory activity, suggesting a protective role to IL-17 in chronic HCV infection. (23)

It is an object of the present invention to enhance the action of IFN and possibly IL-17 by the use of ileal brake hormone releasing substances as CD4 and CD8 T cell regulators, combined with active Hepatitis C vaccines to stimulate the $CD8^+$ T cells to enhance endogenous production of IFN, combined with highly active antivirals against the Hepatitis C virus.

These findings are relevant for Hepatitis C vaccination, timing of vaccination, and also follow on immunotherapy of chronic Hepatitis C infections. Timing vaccination to the stage of the Hepatitis C infection is clearly an important part of the preferred embodiment of the invention. These methods may also comprise the administration of one or more other therapeutic agents during or after the use of a vaccine with or without immunotherapy dosing. The logic of combining a vaccine or immunotherapy with a drug to lower the viral load of Hepatitis C is known to one skilled in the art, but in fact it has not been the case where anti-viral treatment alone has conferred long lasting immunity to Hepatitis C. By way of example, Rahman and colleagues examined recovery in selected patients with acute hepatitis C. (24) In most cases spontaneous recovery was associated with vigorous and long-lasting cellular immune responses. Drug Treatment-induced recovery can be achieved in the majority of patients who are treated in the acute phase, particularly with interferon containing regimens, but the kinetics and mechanisms of viral clearance and immune responsiveness are not well understood. Both direct antiviral effects and indirect immune-mediated effects, such as immune modulation of Th2 to Th1 responses and prevention of exhaustion of cellular responses by rapid reduction of viral titer, have been proposed. To investigate how early antiviral therapy affects hepatitis C virus (HCV)-specific T cell responses, Rahman performed detailed prospective clinical, virological, and immunological studies on 7 patients with acute hepatitis C who received antiviral therapy and were followed at 2 to 4 week intervals for 1 to 2 years. The total CD4(+) and CD8(+) cell response was analyzed with 600 overlapping HCV peptides and 6 proteins by ex vivo enzyme-linked immunospot (ELISpot), intracellular cytokine staining, and proliferation assays. In contrast to earlier studies with selected HCV epitopes, this extended analysis detected multi-specific interferon gamma(+) (IFN-gamma(+)) responses in each patient, even in the absence of T-cell proliferation. After initiation of antiviral therapy (at a mean of 20 weeks after infection), all sustained responders demonstrated gradually decreasing, then nearly absent HCV-specific T-cell responses, whereas the sole patient who developed viral breakthrough after initial HCV control maintained cellular immune responses. Their work points to the fundamental problem of antiviral drugs alone in hepatitis C, that is the lack of association between lowering of viral load with medications and the absence of a lasting enhancement of HCV-specific T-cell responsiveness in the blood (24).

Such observations prompt the combination of an ileum or appendix delivered hepatitis C vaccine with conventional or novel oral drug therapy, a strategy claimed herein in specific embodiments of the invention. Such disclosed combinations are needed to overcome the overall weak T cell response of the host to Hepatitis C virus during infection, the negligible added immunity that is conferred by anti-viral agents, and the need to expose alternative Lymphoid tissues to Hepatitis C in order to produce a durable T cell response which then can be amplified and transferred to long lived memory B cells in the spleen, thymus and bone marrow.

Candidate vaccines have been reviewed recently by Strickland and colleagues, and the entire listing contained therein is claimed as candidate antigens/adjuvants for oral delivery to the ileum and/or the appendix (25) This list is not meant to be limiting since the formulation could be employed for any available antigen.

Recently an oral vaccine has been developed by Rajkannan and colleagues for Hepatitis B. (26) The oral hepatitis B vaccine formulation was prepared by successful encapsulation of immunogenic peptide representing residues 127-145 of the immune-dominant B-cell epitope of hepatitis B surface antigen (HBsAg) in poly(D,L-lactide co-glycolide) (PLG) microparticles. The smooth, spherical PLG microparticles with a diameter of around 10 microns were prepared by using W/O/W double emulsion solvent evaporation method. The entrapment efficiency of B-cell epitope peptide (BCEP) into PLG microparticles was 64%. In vitro studies showed B-cell epitope loaded PLG microparticles (BCEM) released the peptide in sustained profile and reached 64.9% efficiency by Day 25. Single oral immunization of mice with BCEM led to the significant induction of specific serum IgG and IgM anti-HB antibodies. After the termination of antibody induction, the orally immunized mice were infected with HBsAg, which resulted in the rapid production of antibodies against HBsAg as a result of secondary immune response. PLG microparticles formulation approach may have potential in increasing the efficacy of microparticulate systems for the oral administration of hepatitis B vaccine. (26). This approach is notable because it is a duodenal release product but produced good immunity. It is not clear whether the strategy would create the same amount of immunity to Hepatitis C.

In one embodiment, the methods described herein comprise the administration of a formulation of the invention prior to or in combination with anti-viral agents. Examples of anti-viral agents used for Hepatitis B or C include, without limitation, Anti-viral agents including anti-hepatitis B agents and anti-hepatitis C agents are as otherwise described herein and include, for example, Hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 41-4109, EHT899, zadaxin (thymosin alpha-1) and mixtures thereof for hepatitis B infections and ribavirin, pegylated interferon, boceprevir, daclatasvir, asunapavir, INX-189, FV-100, NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, GS 9256, GS 9451, GS 5885, GS 6620, GS 9620, GS9669, ACH-1095, ACH-2928, GSK625433, TG4040 (MVA-HCV), A-831, F351, NS5A, NS4B, ANA598, A-689, GNI-104, IDX102, ADX184, ALS-2200, ALS-2158, BI 201335, BI 207127, BIT-225, BIT-8020, GL59728, GL60667, PSI-938, PSI-7977, PSI-7851, SCY-635, TLR9 Agonist, PHX1766, SP-30 and mixtures thereof for hepatitis C infections.

As used herein, the term "immune response" refers to a humoral immune response and/or cellular immune response leading to the activation or proliferation of B- and/or T-lymphocytes and/or and antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant. Preferably, antigen presenting cells may be activated.

To assess immunogenicity (e.g. whether a formulation has induced a high titer antibody responses against a virus, an anti-viral geometric mean titer (GMT) can be measured, e.g. after a few weeks of treatment (e.g. 3 or 4 weeks) and after administration of a few dosages (e.g. 3 or 4). The percentage of subjects who seroconverted for virus after a few weeks of treatment (e.g. 3 or 4 weeks) and after administration of a few dosages (e.g. 3 or 4) can also be determined to assess immunogenicity.

To determine prophylactic efficacy, an immunogenicity analysis can be conducted on subjects who remain virus seronegative and PCR-negative to virus (swab and biopsy) at various endpoints after challenge.

The invention is illustrated further by the following non-limiting examples.

EXAMPLES

Background

Gut derived mucosal immunity and thus response to vaccines depends on antigen stimulation in specialized lymphoepithelial structures such as Peyer's patches ((27, 28). The integrated dissemination of memory cells from these GI active lymphoid tissues to all exocrine tissues is the functional basis for oral vaccines. There is good evidence that endothelial determinants with affinity for GI associated lymphoid cells are shared among Peyer's Patches, mesenteric lymph nodes and the intestinal lamina propria (29-39). Isolated dendritic cells from these Peyer's Patches regulate the immune system, and have been shown to stimulate T cells in a mixed lymphocyte reaction, and to support IgA B-cell development (40-48). Terminally differentiated B cells of the bone marrow and thymus are responsible for long term immune system memory, these cells are often called plasma cells in the art.

Initial contact of the oral targeted formulation of the administered antigen and adjuvant, is with the dendritic cells of the immune system, typically with specific T cells such as CD4 and CD8. Antigen processing is performed by these initial cells and then the message of the antigen is passed on to B cells for memory and dissemination of the memory among lymphoid cells in the spleen, Liver, thymus, and bone marrow.

With the knowledge of these teachings in hand, it is curious that oral vaccine strategies have been limited in their targeting of these Peyer's patches, and that in large part there have only been enteric coatings applied to antigens in prior art. These enteric coated vaccines bypass the stomach acid and usually release contents at pH of 5.6-6.0, a formulation pathway that is illustrated in FIG. 1. On the other hand, there are no enteric coatings used as drugs or vaccines that have pH release over 7.0 because the view is that these bypass the duodenum, and the duodenum is the primary site of drug absorption. It is not also generally appreciated that the distal small intestine has pH values above 7.3 and ranging up to 8.0 in normal individuals. There is furthermore no generally accepted mechanism or explanation for this high pH in the ileum. In general, it might be stated that the distal ileum is a novel site specific drug delivery target, heretofore unstudied in the art, and because the drug delivery properties are unexplored, the ileum and appendix are also considered to be completely novel vaccine delivery targets. This latter concept arises because of the known immune regulatory actions of Peyer's Patches and the recently discovered actions of ileal brake hormone releasing substances that mimic RYGB on GI tract derived immunity, both of which are incorporated by reference into this disclosure.

It remains, however, a neglected fact that the distal intestine, already identified by our work as the primary sensor for regulation of nutrition, satiety, and control of metabolic syndrome is (because of sensor cells called Peyer's Patches and other lymphoid tissue in the appendix, the ileum and appendix), apparently the gatekeeper of the immune response to invasion by pathogens thru the GI tract. Acting via dendritic cells in Peyer's Patches and in the appendix, antigens and adjuvants impact both cellular and humoral immune pathways, which are in turn controlled by the cells of the distal ileum and the appendix.

The appendix (part of the right colon) has been long known as a primary regulator of innate immunity, and yet there is no vaccine ever proposed to target the appendix directly. Indeed it has not been thought possible to target the appendix and yet we are able to invent an effective and reliable pill within a pill formulation strategy for appendix and Right colon delivery based on the unique pH characteristics of these sites in the intestine.

Example 1

Preparation of Antigen Material for Inclusion in Vaccine Formulations Targeting the Ileum and Appendix Antigens and their associated immunogenic potential are the key component of an optimal vaccine response in both prophylactic vaccination and for immunotherapeutic treatment of disease. There are methods commonly employed to prepare antigens for vaccine, all of which are considered within the scope of this novel formulation disclosure. Antigens are typically non-invasive or inactive fragments of cells or bacteria or viral DNA/RNA that have the immune recognition properties of the whole cells. They are prepared from the whole cells by cell fragmentation and then component separation, with a focus on cell wall components. As the precise sequence of the antigenic fragment is defined, it may be prepared in quantity in bacteria, plant or lymphocytic cell lines. Examples of all of these antigen preparations and selected antigens are claimed as elements for the novel Site Specific GI delivery to the ileum and appendix.

Preparation of Adjuvants for Inclusion in Formulations Targeting the Ileum and Appendix When the immune response to an applied Antigen is weak, short-lived or otherwise insufficient, it is common in the art of vaccine development to boost the response to the antigen by adding an adjuvant to the antigen in the applied formulation. The key element of a successful adjuvant is a resulting immunogenic response to a specific antigen that is greater than the antigen alone. A boosted response to an antigen may either prolong the duration of vaccine protection or it may increase the amount of protection, or both. The net benefit is an improvement in the overall vaccine response in both prophylactic vaccination and for immunotherapeutic treatment of disease. There are methods commonly employed to prepare adjuvants for vaccines, and the inclusion of all of the known or newly developed antigen-adjuvant combinations are considered within the scope of this novel formulation disclosure. Exact compositions of formulated Antigen-Adjuvants are overall within the scope of the disclosed formulation, and specific materials are chosen to avoid inactivation of either the antigen or the adjuvant.

Figure 2:
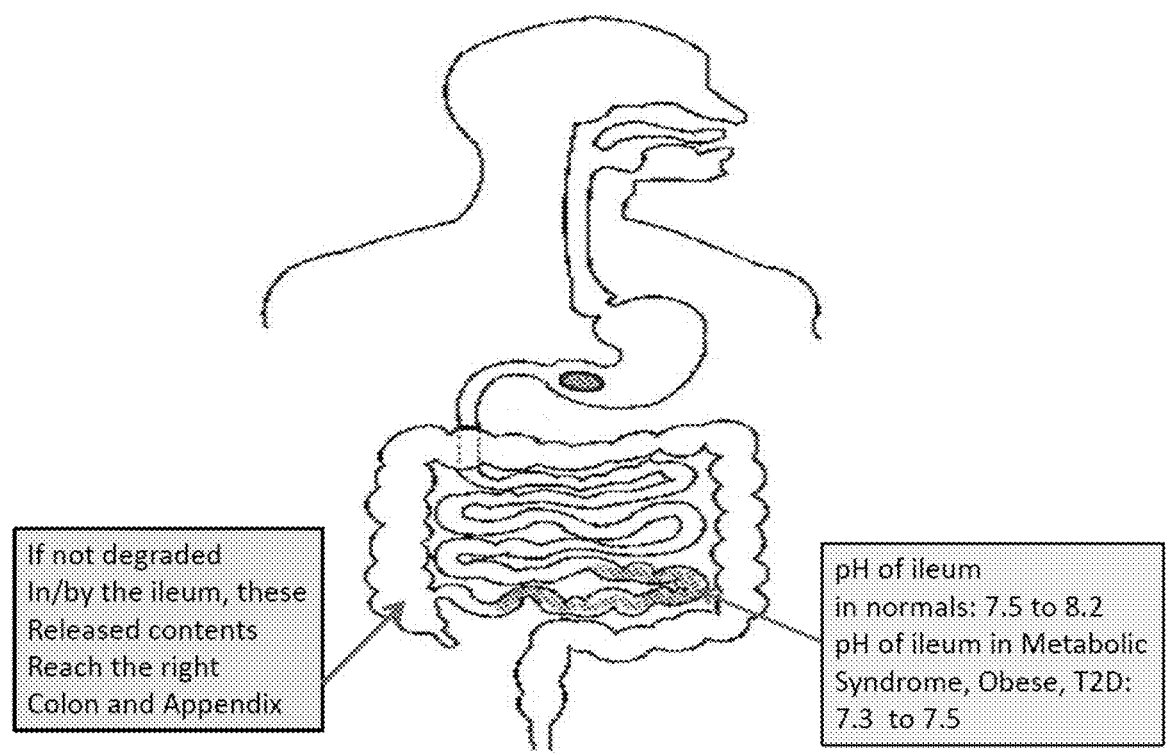
FIG. 2 depicts ileal brake delivery of vaccines: pH target for release is about 7.2-7.5. Aspects of the GI tract location and pH targets in the ileum are provided in the diagram
Figure 3:
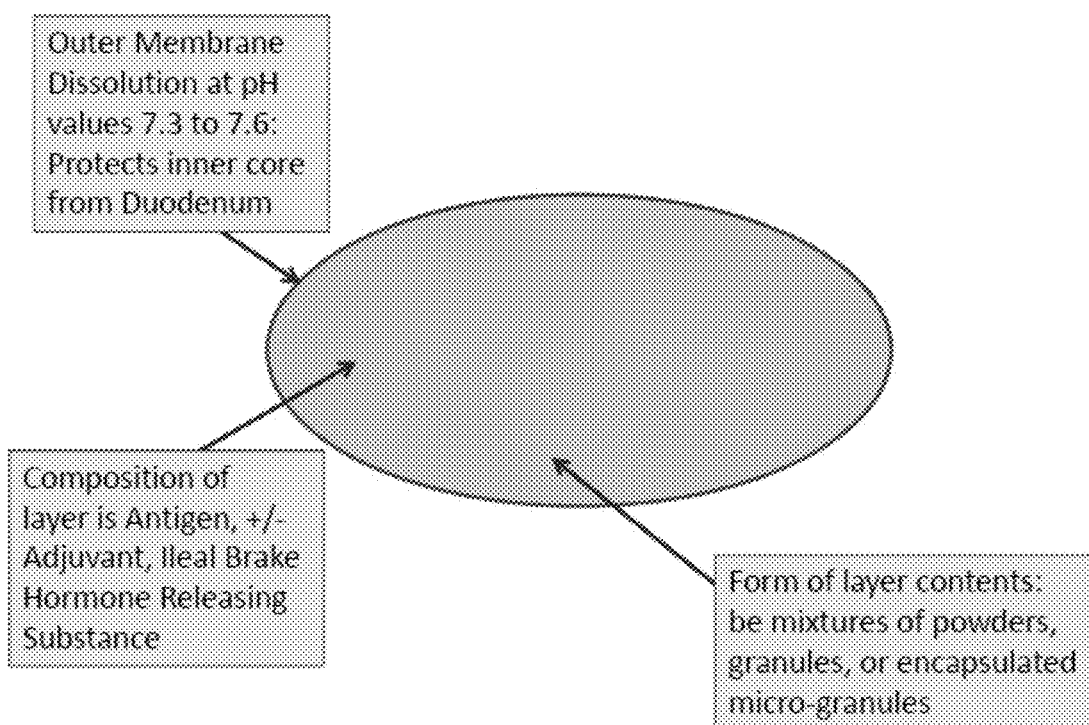
FIG. 3 illustrates the formulation detail applied to ensure ileum release of the claimed vaccine antigens and any adjuvants and/or ileal brake hormone releasing substances that comprise the vaccine. The formulation itself may be mixtures of microgranules, granules or powders, each of which can be combined within the formulation and protected by the coating until it reaches the pH value above 7.3 and target of GI release at least initially in the ileum

General Formulation Methodology:

The general formulation methodology provided herein will deliver Antigens, with or without adjuvants, and with or without ileal brake hormone releasing substances, which themselves optimize the immune response of the dendritic cells of the ileum and thereby function in the role of non-specific adjuvants. All of the formulations disclosed herein are targeting a site in the GI tract that is different from the enteric coating formulations which are applied in the art of oral vaccine delivery, which are by definition targeted to release antigens in the duodenum (see FIG. 1). Studies conducted using the SmartPill technology used to study patients establish the pH readings of the entire GI tract and reveal a target pH for dissolution in the duodenum of 5.5 to 6.0. (49, 50). It was discovered that pH readings of the intestine beyond the duodenum could enable an advanced formulation strategy for site specific oral vaccine delivery disclosed herein. Formulation of the vaccine into a pill within a pill has some common elements as well as some materials that are specific to the antigen being used. The common elements are disclosed in this example and the strategy for specific antigens are shown in later examples Formulation 1, illustrated by FIGS. 2-3, demonstrates the simplest means of GI site specific delivery of antigens with or without adjuvants to the ileum and ileal brake:

1. Identify and produce vaccine quantities of the antigen to be used in stimulating the distal ileum target cells of the immune system
2. Add any adjuvants that may further enhance target cell responsiveness
3. Incorporate any nutritional elements to maintain viability of a live organism antigen
4. Assure the mixture is stable at pH values of 7.3-8.0
5. Encapsulate the components of the mixture into microgranules, powders, or granules
6. Coat the capsule surface to be insoluble at pH<7.3

7. Administer this capsule to the subjects for purposes of determining effective vaccination dose based on measured resultant antibody response.

Figure 4:
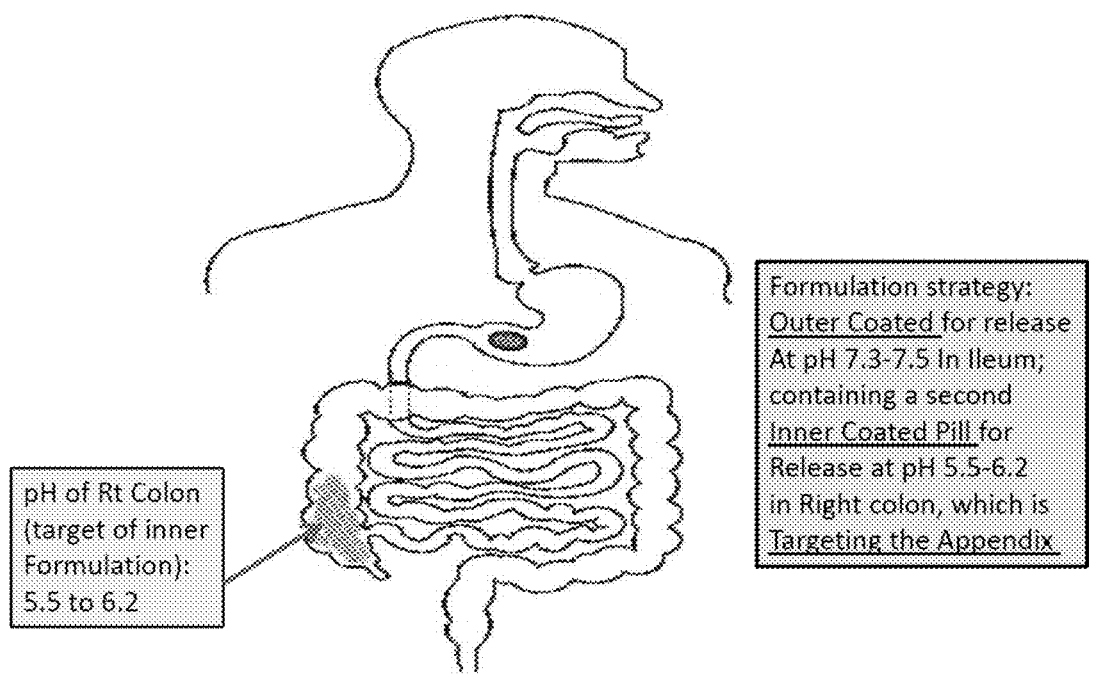
FIG. 4 illustrates that because enteric coating release at pH 5.5 alone targets the duodenum and antigen released in duodenum would not survive transit to reach the colon, right colon and appendix delivery requires an outer and an inner pill. The inner pill strategy is required to bypass the duodenum with the outer coating dissolving only at pH of about 7.3-7.6, which may release its active contents, if any, in the ileum. The inner pill is thereby released intact in the ileum, but does not dissolve there; it passes into the colon where the pH is 5.5 to 6.0 and wherein it releases its contents.
Figure 5:
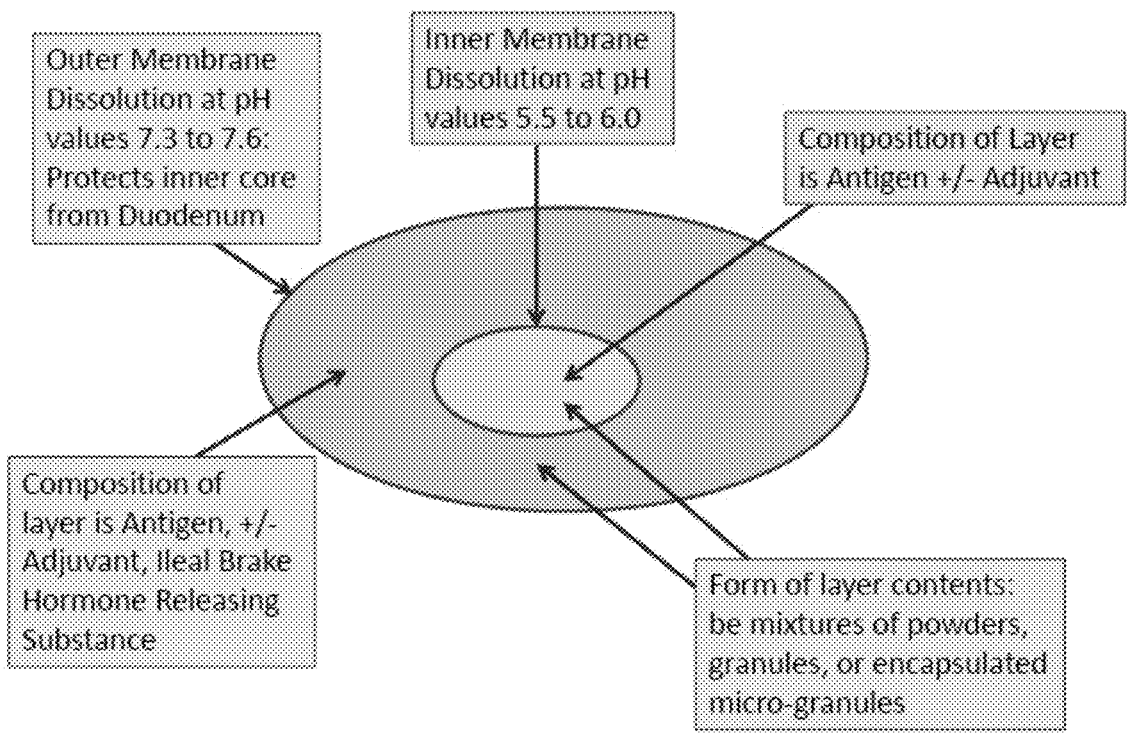
FIG. 5 illustrates the "vaccine pill within a vaccine pill" concept: ileal brake target release (pH 7.3-7.5) and colon/appendix release of inner vaccine pill, which contains vaccine formulation for Appendix target release at pH about 5.5-6.2

Further system modifications (evolution of formulation 2, "pill within a pill"), as illustrated in FIG. 4-6:
1. Develop a second formulation of vaccine antigen that is stable at pH values of about 5.5 to 6.0
2. Encapsulate said mixture with pH release coating of about 5.5
3. Add this second smaller inner pill to the capsule containing the primary antigenic mixture and releasing at about pH 7.3. The second capsule will remain intact at the distal ileum. It will pass into the right colon and reach pH of 5.5, thereby releasing is contents in the right colon and directly reaching the appendix.
4. The Purpose of the inner encapsulation of antigen and adjuvant is to present the contents to the right colon, exposing known lymphoid tissues of the right colon and appendix to vaccine antigens.
5. Administer this dual pill mixture to the subjects for purposes of determining effective vaccination dose based on measured resultant antibody response.

Additional embodiment combining elements of formulation 1 and formulation 2:
1. Create microgranules of formulation 1 mixture, encapsulate so as to release contained antigens at about pH 7.0 to 7.6, thereby spreading the microgranules in the jejunum and ileum and thereby increasing the contact of the GI surfaces such as Peyer's Patches to the antigen mixture.
2. These microgranules can be taken orally with any liquid or food, such as applesauce or yogurt, and they will reach the site of release in the ileum and ileal brake.
3. Alternatively, these microgranules could be encased in a capsule and released at pH 7.0.
4. As a further embodiment, this capsule could also contain a second smaller capsule as in formulation 2, which then would release in the Right colon and near the appendix.
5. Either formulation 1 or formulation 2 could contain ileal brake hormone releasing substances, as these are stimulants of the beneficial immune response needed for regulation of antigen recognition and immune response thereto
6. Either formulation 1 or formulation 2 could contain therapeutically active substances in active amounts directed against the disease, and thereby be used for combination immunotherapy and prevention of infections or cancers Summary—Advantages of GI Site Specific Oral Vaccination Formulations:

1. Lower antigen dose over parenteral dosing, especially when the target of vaccination is ileum and associated immune responsive areas where there is a plurality of immune system antigen receptors such as dendritic cells, T cells and B cells.
2. Oral vaccines present fewer stability problems than injectable vaccines, and they facilitate vaccine use in resource poor countries. In some cases, use of oral vaccines and strategies may even avoid any need for refrigeration.
3. No needles or access to specialized personnel to give shots, when all vaccinations are used as oral products
4. Safety advantages are maximized because lower amounts of antigen can be used to vaccinate via the GI tract, vs. higher amounts that circulate in the body.
5. Booster oral doses are technically easier to administer in cases where more than one dose is needed to maximize immune response.
6. It is easier to give booster oral doses at regular periods, even for cases when the first vaccine dose is injected, providing a means of easily and safely protecting an at-risk population.
7. Smaller amounts of antigen are needed for selective application right to the immune surveillance cells in the distal ileum and appendix
8. This would be the first orally administered vaccine that actually could reach the appendix and be active there in stimulating the immune system.
9. With oral vaccinations, there are fewer or even no concerns for foreign components added as preservatives or for systemic immune reactions to proteins that are injected into the body
10. Oral capsules facilitate booster vaccine strategies, no need to have an injection, just take a second capsule several weeks later. In this way the oral capsules are suitable for serial use in situations where antigen response is weak or short lived (HIV, staphylococcus, Influenza, Hepatitis C and cancers).

Example 2

Development of Formulations Using Supporting Literature or Disclosed Antigens Staphylococci The potential of biocompatible and biodegradable microspheres as a controlled release oral vaccine delivery system has been examined. Orally-administered 1-10 micron microspheres composed of poly (DL-lactide-co-glycolide) were specifically taken up into the Peyer's patch lymphoid tissue of the gut, where those greater than or equal to 5 micron remained for up to 35 days. Microspheres less than 5 micron disseminated within macrophages to the mesenteric lymph nodes and spleen. In contrast to soluble staphylococcal enterotoxin B toxoid, oral immunization with entero-toxoid in microspheres induced circulating toxin-specific antibodies and a concurrent secretory IgA anti-toxin response in saliva and gut fluid. (51)

Theilacker and colleagues recently developed new vaccine antigens around structural modifications of Lipoteichoic acid, and of interest these were shown to develop broad protection against several pathogenic gram positive species. Type 1 lipoteichoic acid (LTA) is present in many clinically important gram-positive bacteria, including enterococci, streptococci, and staphylococci, and antibodies against LTA have been shown to opsonize non-encapsulated *Enterococcus faecalis* strains. In the present study, they show that antibodies against *E. faecalis* LTA also bind to type 1 LTA from other gram-positive species and opsonized *Staphylococcus epidermidis* and *Staphylococcus aureus* strains as well as group B streptococci. Inhibition studies using teichoic acid oligomers indicated that cross-reactive opsonic antibodies bind to the teichoic acid backbone. Passive immunization with rabbit antibodies against *E. faecalis* LTA promoted the clearance of bacteremia by *E. faecalis* and *S. epidermidis* in mice. Furthermore, passive protection also reduced mortality in a murine *S. aureus* peritonitis model. The effectiveness of rabbit antibody against LTA suggests that this conserved bacterial structure could function as a single vaccine antigen that targets multiple gram-positive pathogens. (52). By way of specific example, the oral application of this antigen in a distal GI tract formulation is within the scope of the present invention, as is delivery to the ileum or appendix of the subject being vaccinated.

Another example of a candidate vaccine suitable for oral delivery to ileum and appendix is StaphVAX. StaphVAX is a bivalent polysaccharide- and protein-conjugated vaccine, directed against capsular *Staphylococcus aureus* types 5 and 8, which are associated with 80 to 90% of *S aureus* clinical infections. The vaccine is being developed by Nabi for the potential treatment of infections in kidney patients who are receiving peritoneal dialysis and are prone to serious staphylococcal infections. StaphVAX, in common with other vaccines against *S. aureus*, is not highly immunogenic and the protection is rather short-lived. In February 2001, the sponsoring company Nabi revealed plans to conduct a boosting study of StaphVAX in patients with end-stage renal disease (ESRD). This study would be conducted in patients who were enrolled in the first phase III trial and the company expected completion by early 2002 [283114]. The company was also progressing with scale-up of the manufacturing process for commercial production of the vaccine. The outcome of the later trials was a confirmation of the overall weak immunogenicity and short lived response, and at the present time this vaccine is waiting for a strategy to increase its immunogenicity and duration (53-57)

A vaccine strain directed against lipoteichoic acid (LTA), a major cell wall component of gram-positive bacteria, has recently completed a Phase II study suggesting efficacy and is being developed further for clinical investigation (58).

Diptheria

Liposomes have been used to encapsulate antigens and adjuvants since 1974. One major limitation for the use of liposomes in oral vaccines is the lipid structure instability caused by enzyme activities in the duodenum. The aim of the authors was to combine liposomes that could encapsulate antigens (i.e., Dtxd, diphtheria toxoid) with chitosan, which protects the particles and promotes mucoadhesibility. They employed physical techniques to understand the process by which liposomes (SPC: Cho, 3:1) can be sandwiched with chitosan (Chi) and stabilized by PVA (poly-vinylic alcohol), which are biodegradable, biocompatible polymers. Round, smooth-surfaced particles of REVs-Chi (reversed-phase vesicles sandwiched by Chi) stabilized by PVA were obtained. The REVs encapsulation efficiencies (Dtxd was used as the antigen) were directly dependent on the Chi and PVA present in the formulation. Chi adsorption on the REVs surface was accompanied by an increase of zeta-potential. In contrast, PVA adsorption on the REVs-Chi surface was accompanied by a decrease of zeta-potential. The presence of Dtxd increased the Chi surface-adsorption efficiency. The PVA affinity by mucine was 2,000 times higher than that observed with Chi alone and did not depend on the molecule being in solution or adsorbed on the liposomal surface. The liberation of encapsulated Dtxd was retarded by encapsulation within REVs-Chi-PVA. These results lead us to conclude that these new, stabilized particles were able to be adsorbed by intestinal surfaces, resisted degradation, and controlled antigen release. Therefore, REVs-Chi-PVA particles can be used as an oral delivery adjuvant. (59)

A double-blind study was performed in 12 healthy volunteers in order to determine whether circulating immunocytes are present after oral immunization. Sequential samples of peripheral blood were collected at various times after ingestion of a ribosome vaccine (D53) or placebo. Immunoglobulin-containing cells were identified in immunofluorescence and specific antibody-forming cells were detected in agarose ELISA-spot. Higher numbers of both types of cells were observed in the group of individuals receiving ribosomal extracts. An open study allowed a better approach to the kinetics of this phenomenon, related to the release of activated B-cells from Peyer's patches upon antigenic stimulation. This methodological approach has been described in animal models but seldom reported in humans. (60)

In order to elucidate the physiological basis for mucosal immunity of oral vaccination and to present the essential carrier of microparticles or nanoparticles used to investigate the orally delivered vaccine, the features of antigen presentation and mucosal immune reaction in gut-associated lymphoid tissues were analyzed. Considered the morphological and physiological barriers of the gastrointestinal tract, absorption and transport of particulates were further discussed, and the studies about particulate dosage forms for oral vaccine delivery were also summarized in this review. Peyer's patches and M-cells, involved in immune-regulation, are significant areas performing the critical role in oral vaccine delivery strategies. The applied vesicle of microparticles could overcome the barriers and degradation pathways of the gastrointestinal tract. Oral vaccination was endued with new connotation, especially the enhanced transport and immunization efficiencies promoted by the lectin anchored particles. In conclusion, oral vaccination mediated by particulate carrier via mucosal immune system, would contribute to the site-specific triggering and signal magnification. For vaccines, the prospects for the application of these promising carrier systems might have potential attraction for scientific research and commercial development. (61). The disclosed use herein of formulation 1 and formulation 2 enable these GI target site specific vaccines and provide a specific means of reducing these to practice. In this example, we claim an oral means of delivery of any distal ileum or right colon targeted vaccine to those specific sites in the GI tract, for optimized immune system vaccine response.

Hepatitis

Efficient immunization against hepatitis B virus (HBV) and other pathogens with plant-based oral vaccines has been described by Pniewski (62), and requires appropriate plant expressors and the optimization of vaccine compositions and administration protocols. Then these immunogenic components require GI site specific target formulations for the production of optimal immune response in the subject. Previous immunization studies were mainly based on a combination of the injection of a small surface antigen of HBV (S-HBsAg) and the feeding with raw tissue containing the antigen, supplemented with an adjuvant, and coming from plants conferring resistance to kanamycin. The objective of their study was to develop a prototype oral vaccine formula suitable for human immunization. Herbicide-resistant lettuce was engineered, stably expressing through progeny generation micrograms of S-HBsAg per g of fresh weight and formed into virus-like particles (VLPs). Lyophilized tissue containing a relatively low, 100-ng VLP-assembled antigen dose, administered only orally to mice with a long, 60-day interval between prime and boost immunizations and without exogenous adjuvant, elicited mucosal and systemic humoral anti-HBs responses at the nominally protective level. Lyophilized tissue was converted into tablets, which preserved S-HBsAg content for at least one year of room temperature storage. The results of the study provide indications on immunization methodology using a durable, efficacious, and convenient plant-derived prototype oral vaccine against hepatitis B. (62)

Current immunization programs against hepatitis B virus (HBV) increasingly often involve novel tri-component vaccines containing—together with the small (S-HBsAg)—also medium and large surface antigens of HBV (M- and L-HBsAg). Plants producing all HBsAg proteins can be a source of components for a potential oral 'triple' anti-HBV vaccine.

The objective of the presented research was to study the potential of M/L-HBsAg expression in leaf tissue and conditions of its processing for a prototype oral vaccine. Tobacco and lettuce carrying M- or L-HBsAg genes and resistant to the herbicide glufosinate were engineered and integration of the transgenes was verified by PCR and Southern hybridizations. M- and L-HBsAg expression was confirmed by Western blot and assayed by ELISA at the level of micrograms per g of fresh weight. The antigens displayed a common S domain and characteristic domains preS2 and preS1 and were assembled into virus-like particles (VLPs). Leaf tissues containing M- and L-HBsAg were lyophilised to produce a starting material of an orally administered vaccine formula. The antigens were distinctly sensitive to freeze-drying conditions and storage temperature, in the aspect of stability of S and preS domains and formation of multimeric particles. Efficiency of lyophilisation and storage depended also on the initial antigen content in plant tissue, yet M-HBsAg appeared to be approximately 1.5-2 times more stable than L-HBsAg. The results of the study provide indications concerning the preparation of two other constituents, next to S-HBsAg, for a plant-derived prototype oral tri-component vaccine against hepatitis B. (63)

An oral hepatitis B vaccine formulation was prepared by successful encapsulation of immunogenic peptide representing residues 127-145 of the immunodominant B-cell epitope of hepatitis B surface antigen (HBsAg) in poly(D,L-lactide co-glycolide) (PLG) microparticles. The smooth, spherical PLG microparticles with a diameter of around 10 microns was prepared by using W/O/W double emulsion solvent evaporation method. The entrapment efficiency of B-cell epitope peptide (BCEP) into PLG microparticles was 64%. In vitro studies showed B-cell epitope loaded PLG microparticles (BCEM) released the peptide in sustained profile and reached 64.9% efficiency by Day 25. Single oral immunization of mice with BCEM led to the significant induction of specific serum IgG and IgM anti-HB antibodies. After the termination of antibody induction, the orally immunized mice were infected with HBsAg, which resulted in the rapid production of antibodies against HBsAg as a result of secondary immune response. PLG microparticle formulations may have potential for increasing the efficacy of microparticulate systems for the oral administration of hepatitis B vaccine. (26)

An oral vaccine formulation comprised of starch microparticles with conjugated antigens is being developed, and the authors have examined the uptake of such microparticles by the intestinal mucosa and examined whether the conjugated antigen can influence the uptake. Two model antigens were used: recombinant cholera toxin B subunit (rCTB), which is known to bind to the ubiquitous GM1-receptor, and human serum albumin (HSA) which is not known to have any specific binding properties. The uptake was studied in mouse ligated intestinal loops into which the microparticles were injected. The intestinal loops were excised, fixed in ice-cold 95% ethanol. Entire specimens were mounted, exposed to fluorescence-labeled reagents staining the cytoskeleton, the particles and/or M cells and examined in a confocal laser-scanning microscope. A qualitative difference in the uptake of the rCTB- and HSA-conjugated microparticles was seen. The rCTB-conjugated microparticles were found both in villi and in the follicles of the Peyer's patches. HSA-conjugated microparticles could only be detected in the follicles of the Peyer's patches and not in villi. The rCTB conjugated to the microparticles did not lose its ability to bind the GM1-receptor, as shown with a GM1-ELISA, and the uptake of rCTB-conjugated microparticles in villi is most probably facilitated by the rCTB binding to the GM1-receptor. The qualitative difference in uptake could be of importance for the development of an immune response as the cytokine and chemokine microenvironment during antigen presentation will decide the differentiation of the immune response induced. (64)

Influenza

Induction of mucosal immunity through oral immunization is an effective way to control influenza infection. The approach is so successful that even patients with compromised immune systems such as occurs in HIV and cancers can achieve immunity to Influenza. In the course of animal testing with a product related embodiment, baculovirus displaying influenza hemagglutinin was encapsulated within a reverse micelle structure of phosphatidylcholine and delivered into the gastrointestinal tract of mice to study its efficacy as an oral vaccine against cross-clade H5N1 infection. Mice vaccinated with encapsulated baculovirus displaying HA (En-BacHA) showed significantly enhanced HA specific serum IgG and mucosal IgA antibodies, and higher hemagglutination inhibition (HI) titers, when compared to its non-encapsulated form (BacHA). Estimation of serum neutralizing antibodies also indicated that En-BacHA formulation was able to induce strong cross-clade neutralization against heterologous H5N1 strains (clade 1.0, clade 2.1, clade 4.0 and clade 8.0). Further, mice vaccinated with En-BacHA alone were able to confer 100% protection against 5MLD50 of HPAI heterologous H5N1 strain (clade 1). Inclusion of recombinant cholera toxin B subunit as a mucosal adjuvant in the vaccine formulation did not show any significant effect in both systemic and mucosal immune responses. The authors concluded that oral delivery of encapsulated recombinant H5 HA expressed on baculovirus surface was an effective way to prime the immune system against H5N1 infection in mice and will have no biosafety concerns associated with their production or administration. (65)

These are products in need of targeted delivery. Using the instant invention, these products could readily be formulated for delivery to the ileum and appendix, with the expected increase in antibody protective response, a direct benefit of the antigen surviving beyond the acid of the stomach and the proteases in the duodenum.

An effective experimental vaccine may fail to become a therapeutic reality for a number of scientific, regulatory or commercial reasons. In this review, the authors share some of their personal experiences as University-based researchers and provide an account of some of the problems encountered during preliminary scale-up and assessment of an oral influenza vaccine formulation. Many of the problems faced have been non-scientific, and related to identifying project-funding sources, finding suitable contract manufacturing companies that are GMP compliant, and protecting intellectual property generated from the scientific studies. The review is intended as a practical guide that will allow other researchers to adopt effective strategies to permit the translation of an effective experimental formulation to a viable commercial product. (66)

Influenza would appear a promising candidate for oral vaccination via the ileum and appendix, and there are many potential and obvious advantages to adoption of this route of vaccination over the currently available methods of intramuscular injection or nasal inhalation. Every year, FDA convenes a meeting with manufacturers to define the vaccine strains to be used in the fall season. In 2012, the FDA Committee established a trivalent Influenza vaccine containing 3 strains: Strain A/California/7/2009 (H1N1)-like virus; Strain A/Victoria/361/2011 (H3N2)-like virus; Strain B/Wisconsin/1/2010-like virus (B/Yamagata lineage). In order to produce an oral influenza vaccine targeting the ileum and appendix using the instant invention, each of these FDA selected strains would be encapsulated separately into microgranules. The microgranules would be mixed in 1:1:1 ratio and placed into the capsule prior to coating to pH release above 7.3. To target the appendix, the mixture of microgranules would be first encapsulated into an inner pill with dissolution at pH between 5.5 and 6.0. In this way, the contents of the inner pill would reach the appendix according to the teachings of FIGS. 4-6 when the microgranules are encapsulated into Formulation 1 and 2. Oral use of this formulation for influenza vaccine 2012 would be proposed as an alternative to a mixture of these same strains in a vaccine to be injected or inhaled. We would test this influenza formulation with and without the non-specific adjuvant. According to the teachings of this formulation approach to Influenza, a similar approach would be applied to the strains selected by the FDA committee in each year a selection is made.

Obesity is probably the most important risk factor for increased severity of influenza virus infections and mortality (67), and is believed to have negative impact on vaccine efficacy. Recently, mortality has emerged as an outcome of pandemic influenza A virus subtype H1N1, necessitating development of more effective vaccine strategies, perhaps targeting the immune responsive gastrointestinal tract.

In obese mice, Kim and colleagues investigated effects of diet-induced obesity on vaccine-induced immune responses and protective efficacy against pandemic H1N1 influenza virus. Diet-induced obese and lean C57BL/6J mice were immunized with commercial monovalent 2009 H1N1 vaccine, and antigen-specific antibody responses and neutralizing activities were observed. Following vaccination, mice were challenged with homologous H1N1 virus, and pathogenesis and mortality were examined. Vaccine-induced H1N1-specific antibody responses and neutralizing activities were markedly reduced in obese mice. Consistent with antibody responses, lung virus titers were significantly higher in obese mice than in lean controls after challenge. In addition, obese group showed greatly increased expression of proinflammatory cytokines and chemokines in lung tissue, severe lung inflammation, and higher eventual mortality rate (100%) compared with that among lean control mice (14%). The study results show that prophylactic immune responses and protectiveness induced by 2009 H1N1 vaccine could be extremely compromised in diet-induced obesity. These results suggest that novel vaccination strategies are required for high-risk groups, including the obese population. (68)

It is of note that pH of the ileum is different in obesity from that of normals, and these results have already led to the improved use of ileal brake hormone releasing substances in the manner of mimicry of RYGB surgery, results incorporated by reference. Clearly, oral vaccine formulations for influenza and potentially other ileum targeted oral vaccines should be adjusted for the somewhat lower pH found in the ileum of obese subjects. Accordingly, we have set the target for release at pH of 7.3, which should allow for effective use of oral vaccines in the obese patient as well as normal or lean.

Others have noted a need for a better immunogenic response to the influenza vaccine, and Kim and colleagues set out to develop a novel skin delivery method that is simple and allows for easy self-administration. They prepared microneedle patches with stabilized influenza vaccine and investigated their protective immune responses in mice. Mice vaccinated with a single microneedle dose of trehalose-stabilized influenza vaccine developed strong antibody responses that were long-lived. Compared with traditional intramuscular vaccination, stabilized microneedle vaccination was superior in inducing protective immunity, as was evidenced by efficient clearance of virus from the lung and enhanced humoral and antibody-secreting cell immune responses after 100% survival from lethal challenge. Vaccine stabilization was found to be important, because mice vaccinated with an unstabilized microneedle vaccine elicited a weaker immunoglobulin G 2a antibody response, compared with the stabilized microneedle vaccine, and were only partially protected against viral challenge. It was their hypothesis that improved trafficking of dendritic cells to regional lymph nodes as a result of microneedle delivery to the skin might play a role in contributing to improved protective immunity. CONCLUSIONS: These findings suggest that vaccination of the skin using a microneedle patch can improve protective efficacy and induce long-term sustained immunogenicity and may also provide a simple method of administration to improve influenza vaccination coverage. (69)

These experiments offer another potential advantage of target administration of vaccines to the GI tract via an oral formulation targeting the dendritic cells and lymphoid tissues of the ileum and appendix. Specifically the vaccination will be more potent when applied in this manner.

Cholera

The emergence of the *Vibrio cholerae* O139 serogroup of *V. cholera*, capable of causing severe dehydrating cholera has over the decade led to efforts in formulation of vaccines to protect against this pathogen. Although the prevalence of diarrhea due to *V. cholerae* O139 has recorded a decrease, efforts on vaccine development continues to formulate an oral vaccine capable of stimulating the gut mucosal system. We have studied the mucosal immunogenicity in Bangladeshi adults to a killed whole cell (WC) bivalent cholera vaccine composed of *V. cholerae* O139 as well as *V. cholerae* O1 strains together with the recombinant cholera toxin B subunit (CTB) (WC-O1/O139/CTB) and compared the immune responses to that obtained with the licensed monovalent cholera vaccine, Dukoral (WC-O1/CTB). Direct estimation of the WC-O1/O139/CTB vaccine-specific mucosal responses were carried out using lymphocytes isolated from duodenal biopsies, intestinal lavage fluid and feces. The vaccine induced robust antibody-secreting cell responses in the duodenum specific to CTB as well as the O1 and O139 lipopolysaccharide (LPS). Magnitude of response was higher in the gut than in the circulation in all three antibody isotypes. The CTB and LPS-specific mucosal antibody responses were also seen in intestinal lavage fluid and fecal extracts. Vibriocidal antibody responses in plasma were observed to both the *V. cholerae* O1 and O139 serogroups (76% and 57% response rates, respectively). Plasma IgA and IgG responses to CTB and IgA responses to both O1 and O139 LPS were elevated. The immune responses were comparable to that seen to the monovalent WC-O1/CTB recipients in all components studied. Overall, the bivalent cholera vaccine induces strong mucosal responses and the addition of the O139 component does not interfere with the responses to the licensed vaccine Dukoral. This sets the ground for testing such vaccines in large field trials in Bangladesh and also demonstrates that addition of other vibrio components to the existing cholera vaccine does not alter the responses to the O1 vaccine components. (70)

The aim of this work was to evaluate the microencapsulation by spray-drying of inactivated *Vibrio cholerae*, using methacrylic copolymers Eudragit® L30D-55 and FS30D. The microparticles obtained presented a particle size around 3.0 mum. The preparation temperature affected the morphology and the antigenicity of microparticles, but it did not affect the *V. cholerae* content. In vitro release studies showed that in acid medium less than 5% of bacteria was released, and in neutral medium, Eudragit® L30D-55 microparticles released 86% after 24 h, whereas FS30D released less than 30%. Rats inoculated with microparticles exhibited vibriocidal antibody titres. Microencapsulation by spray-drying of inactivated *V. cholerae* could be proposed as a method to obtain an oral vaccine which provides controlled release of the bacteria. (71)

BCG for TB

Bovine tuberculosis (bTB) caused by infection with *Mycobacterium bovis* is causing considerable economic loss to farmers and Government in the United Kingdom as its incidence is increasing. Efforts to control bTB in the UK are hampered by the infection in Eurasian badgers (Meles meles) that represent a wildlife reservoir and source of recurrent *M. bovis* exposure to cattle. Vaccination of badgers with the human TB vaccine, *M. bovis* Bacille Calmette-Guerin (BCG), in oral bait represents a possible disease control tool and holds the best prospect for reaching badger populations over a wide geographical area. Using mouse and guinea pig models, we evaluated the immunogenicity and protective efficacy, respectively, of candidate badger oral vaccines based on formulation of BCG in lipid matrix, alginate beads, or a novel microcapsular hybrid of both lipid and alginate. Two different oral doses of BCG were evaluated in each formulation for their protective efficacy in guinea pigs, while a single dose was evaluated in mice. In mice, significant immune responses (based on lymphocyte proliferation and expression of IFN-gamma) were only seen with the lipid matrix and the lipid in alginate microcapsular formulation, corresponding to the isolation of viable BCG from alimentary tract lymph nodes. In guinea pigs, only BCG formulated in lipid matrix conferred protection to the spleen and lungs following aerosol route challenge with *M. bovis*. Protection was seen with delivery doses in the range 10(6)-10(7) CFU, although this was more consistent in the spleen at the higher dose. No protection in terms of organ CFU was seen with BCG administered in alginate beads or in lipid in alginate microcapsules, although 10(7) in the latter formulation conferred protection in terms of increasing body weight after challenge and a smaller lung to body weight ratio at necropsy. These results highlight the potential for lipid, rather than alginate, -based vaccine formulations as suitable delivery vehicles for an oral BCG vaccine in badgers. (72)

Novel poly (dl-lactide-co-glycolide) microparticles for oral vaccine delivery were formulated using the enteric polymers Eudragit L100-55 and carboxymethylethylcellulose (CMEC) as stabilizers. To serve as a control, microparticles were also produced using the conventional PVA surfactant. In all three cases the antigen, ovalbumin (OVA)-loaded microparticles produced were less than 5 microns in diameter and had a spherical, smooth rounded appearance. The presence of surfactants at the microparticle surface was demonstrated by the surface analysis techniques, XPS and SSIMS. Incubation of microparticles with solutions of pepsin or trypsin led to the removal of a proportion of the antigen associated with all three systems. However, in three CMEC-stabilised microparticle formulations and one of three Eudragit formulations, a high percentage of the associated antigen was protected from removal by a solution of pepsin at pH 1.2 compared with the PVA-stabilised microparticles. In addition, with certain CMEC and Eudragit formulations a degree of protection was also afforded to the associated OVA against removal by trypsin at pH 7.4. Following the incubation of microparticles in simulated gastric fluid a higher percentage of intact antigenic OVA was detected in microparticles stabilised using CMEC than in the PVA- and Eudragit-stabilised formulations. Oral immunisation of mice with OVA-loaded microparticles stabilised using either of the three surfactants led to the induction of specific serum IgG and salivary IgA antibodies. Significantly higher levels of specific salivary IgA antibody to OVA were measured in mice immunised with the CMEC-stabilised microparticles than with the other two formulations. This novel approach in PLG microparticle formulation may have potential in increasing the efficacy of microparticulate systems for the oral administration of vaccines. (73)

In summary, the strategies for oral vaccination are much more commonly used to immunize animal populations than for human immunization. However, the novel formulation strategy for antigens disclosed herein will permit widespread use of oral vaccination to prevent serious infectious disease, as well as oral immunotherapy in support of treatment for chronic viral infections or cancers.

Example 3

A General Stimulant of the B Cell Responses from Cancer Antigens and Fragments that could be Easily Delivered to the Appendix A great deal of work on cancer antigens has been carried out at Roswell Park Cancer center in Buffalo N.Y. This work has lead to a large number of antigens to solid tumors (1-10). The use of these antigens in a formulation delivering them to the ileum and appendix (formulation 2) is hereby claimed as within the scope of this technology.

Other examples of tumor antigens are known by those skilled in the art. For example, Kozbor studied the GD2 ganglioside, displayed by five carbohydrate Neu5Acalpha2-8Neu5Acalpha2-3(GalNAcbeta1-4) Galbeta1-4Glcbeta residues attached to a ceramide chain that anchors the ganglioside in the cell membrane, which is expressed on neuroectodermally derived tumors. GD2 has been used as a target for passive and active immunotherapy in patients with malignant melanoma and neuroblastoma. Kozbor generated a 47-LDA mimotope of GD2 by screening a phage display peptide library with anti-GD2 mAb 14G2a, and reported that vaccination with the 47-LDA mimotope elicited GD2 cross-reactive IgG antibody responses as well as MHC class I-restricted CD8(+) T cells to syngeneic neuroblastoma tumor cells. The cytotoxic activity of the vaccine-induced CTLs was independent of GD2 expression, suggesting recognition of a novel tumor-associated antigen cross-reacting with 47-LDA. Immunoblotting studies using 14G2a mAb demonstrated that this antibody cross-reacts with a 105 kDa glycoprotein expressed by GD2(+) and GD2(−) neuroblastoma and melanoma cells. Functional studies of tumor cells grown in three-dimensional (3D) collagen cultures with 14G2a mAb showed decreases in matrix metalloproteinase-2 activation, a process regulated by 105 kDa activated leukocyte cell adhesion molecules (ALCAM/CD166). The CD166 glycoprotein was shown to be recognized by 14G2a antibody, and inhibition of CD166 expression by RNA interference ablated the cell sensitivity to lysis by 47-LDA-induced CD8(+) T cells in vitro and in vivo. These results suggest that the vaccine-induced CTLs recognize a 47-LDA cross-reactive epitope expressed by CD166 and reveal a novel mechanism of induction of potent tumor-specific cellular responses by mimotopes of tumor-associated carbohydrate antigens. (74)

Segal et al studied heat shock proteins (HSPs), which are potent inducers of immunity and have been harnessed as vaccine adjuvants targeted to cancers and infections. HSPs are a group of ubiquitous intracellular molecules that function as molecular chaperones in numerous processes, such as protein folding and transport, and are induced under stress conditions, such as fever and radiation. Certain HSPs are potent inducers of innate and antigen-specific immunity. They activate dendritic cells partly through toll-like receptors, activate natural killer cells, increase presentation of antigens to effector cells and augment T-cell and humoral immune responses against their associated antigens. Their roles in priming multiple host defense pathways are being exploited in vaccine development for cancer and infectious diseases. (75)

Further specifics on Heat Shock Proteins: Several studies have confirmed that certain stress proteins can function as potent vaccines against a specific cancer when purified from the same tumor. Recent studies of two long-recognized but unexamined stress proteins, heat shock protein (HSP) 110 and glucose-regulated protein (grp) 170, have shown them to be efficient peptide chain-binding proteins. The present investigation examines the vaccine potential of HSP110 and grp170. First, it is shown that prior vaccination with HSP110 or grp170 purified from methylcholanthrene-induced fibrosarcoma caused complete regression of the tumor. In a second tumor model, HSP110 or grp 170 purified from Colon 26 tumors led to a significant growth inhibition of this tumor. In addition, HSP110 or grp170 immunization significantly extended the life span of Colon 26 tumor-bearing mice when applied after tumor transplantation. A tumor-specific cytotoxic T lymphocyte response developed in the mice immunized with tumor-derived HSP 110 or grp 170. Furthermore, treatments of the mice with bone marrow-derived dendritic cells pulsed with these two proteins from tumor also elicited a strong antitumor response. Studies showed that mild, fever-like hyperthermic conditions enhance the vaccine efficiency of HSP110 as well as heat shock cognate 70, but not grp170. These studies indicate that HSP110 and grp170 can be used in HSP-based cancer immunotherapy, that Ag-presenting dendritic cells can be used to mediate this therapeutic approach, and that fever-level hyperthermia can significantly enhance the vaccine efficiency of HSPs. (76)

Ovarian Cancer. Cancer-testis (CT) antigens are expressed in a variety of cancers, but not in normal adult tissues, except for germ cells of the testis, and hence appear to be ideal targets for immunotherapy. In an effort to examine the potential of NY-ESO-1 and LAGE-1 CT antigens for immunotherapy in epithelial ovarian cancer (EOC), we examined the expression of these antigens by reverse transcription-PCR (RT-PCR) and immunohistochemistry (IHC) in a large panel of EOC tissues and cell lines. Sera from a subgroup of the patients were tested for NY-ESO-1/LAGE-1 antibody by ELISA. The data indicated that four ovarian cancer cell lines were positive for one or both CT antigens. Expression of NY-ESO-1 in EOC was demonstrated by RT-PCR and/or IHC in 82 of 190 (43%) specimens. NY-ESO-1 expression by IHC ranged from homogeneous to heterogeneous pattern. LAGE-1 mRNA expression was present in 22 of 107 (21%) tumor tissues. Overall, the expression of either NY-ESO-1 or LAGE-1 mRNA was present in 42 of 107 (40%) EOC specimens and co-expression of both antigens was demonstrated in 11% of specimens. Antibody to NY-ESO-1/LAGE-1 was present in 11 of 37 (30%) patients whose tumors expressed either NY-ESO-1 or LAGE-1. Detectable antibodies were present for up to 3 years after initial diagnosis. Although there was no statistically significant relation between expression of NY-ESO-1/LAGE-1 antigen and survival, the data showed aberrant expression of NY-ESO-1 and LAGE-1 by IHC/RT-PCR in a significant proportion of EOC patients. These findings indicate that NY-ESO-1 and LAGE-1 are attractive targets for antigen-specific immunotherapy in EOC. (77)

Adjuvants do not have to be proteins, especially if the ileum associated Peyer's Patches are targeted by means of the presently claimed invention.

Example 4

Oral Vaccine Formulation

An oral vaccine formulation comprised of starch microparticles with conjugated antigens was developed.

The uptake of such microparticles by the intestinal mucosa was measured and the authors examined whether the conjugated antigen can influence the uptake.

Two model antigens were used in the preparation of this vaccine: recombinant cholera toxin B subunit (rCTB), which is known to bind to the ubiquitous GM 1-receptor, and human serum albumin (HSA) which is not known to have any specific binding properties. The uptake was studied in mouse ligated intestinal loops into which the microparticles were injected. The intestinal loops were excised, fixed in ice-cold 95% ethanol. Entire specimens were mounted, exposed to fluorescence-labeled reagents staining the cytoskeleton, the particles and/or M cells and were examined in a confocal laser-scanning microscope. A qualitative difference in the uptake of the rCTB- and HSA-conjugated microparticles was seen. The rCTB-conjugated microparticles were found both in villi and in the follicles of the Peyer's patches. HSA-conjugated microparticles could only be detected in the follicles of the Peyer's patches and not in villi. The rCTB conjugated to the microparticles did not lose its ability to bind the GM1-receptor, as shown with a GM1-ELISA, and the uptake of rCTB-conjugated microparticles in villi is most probably facilitated by the rCTB binding to the GM 1-receptor. The qualitative difference in uptake could be of importance for the development of an immune response as the cytokine and chemokine microenvironment during antigen presentation will decide the differentiation of the immune response induced. (64) The experimental findings of this work enable the use of formulation 1 in oral GI site specific targeting of vaccines, as the sites in the intestine reached in the experimental preparation are the same as those enabled in human use of oral vaccination by said site specific release methodology.

Example 5 is directed toward the making and testing of a vaccine oral formulation for GI site specific delivery of antigens with or without adjuvants initially to the ileum and following thereafter to the appendix for stimulating the distal ileum target and/or appendix cells of the immune system.

Target delivery: vaccine (live attenuated bacteria "*listeria monocytogenes*" with/or without peptide fusion proteins as antigens with "L-leucine" as a pharmaceutical aid) for delivery in ileum at pH 7.3 to 7.6 and appendix at pH 5.5-6.2 Active Pharmaceutical Ingredient (API):

Live highly attenuated bacteria: *listeria monocytogenes* are provided by Denisco, CHR Hansen, Institu Risell—Lallemand and/or other high quality global suppliers L-leucine (dispersibility aid)—supplied by Ajinomoto and Tyloxapol, USP (Anti-clumping aid) supplied by Sigma Aldrich Inactive ingredients (excipients)—microcrystalline cellulose, lactose, pregelatinized starch, silicon dioxide, HPMC or equivalent "polymers", hard gelatin or HPMC capsules, gelatin, vegetable oil and other fillers, etc.—purchased from local us supplier such as FMC, Capsugel, Colorcon, Evonik, etc.

Intermediate formulation/manufacturing process (at local CMO, controlled room and humidity conditions throughout the process):

"Dried Vaccine Powder (10-100 Microns) Intermediate Formulation"

| Ingredients | Amount (%) |
|---|---|
| Freeze dried, live and highly attenuated bacteria (species of *listeria monocytogenes*) | 5% |
| L-leucine | 95% |
| Water as required | 0% |

Prepared by mixing l-leucine, freeze dried, live and highly attenuated bacteria (species of *listeria monocytogenes*) with water and further freeze/spray dried in freeze/spray drier to remove water.

Example final product—capsule-in-capsule (hard gelatin)—formulation/manufacturing process (at local CMO, controlled room and humidity conditions throughout the process):

| Ingredients | Amount (%) |
|---|---|
| Dried vaccine powder intermediate formulation | 10% |
| Excipients (Microcrystalline cellulose - filler, Silicon dioxide - glidant/flow aid) | 58% |
| Hard gelatin or HPMC capsules | 9% |
| HPMC or equivalent "polymers" (Barrier coat) | 1% |
| "Polymers" (pH 5.5 to 6.2 sensitive coating) | 10% |
| HPMC or equivalent "polymers" (Barrier coat) | 1% |
| "Polymers" (pH 7.2 to 7.6 sensitive coating) | 10% |
| HPMC or equivalent "polymers" (Seal coat) | 1% |
| Water/solvents as required | 0% |

The above dried vaccine powder intermediate formulation, and a portion of excipients are blended in a V-type or similar blender. The blended powders are filled into small (~22 microliter capacity) HPMC capsules using encapsulating equipment. The above capsules are coated (barrier coat) with aqueous or solvent coating solution of HPMC or equivalent "polymers" in a coating pan or fluid bed drier/coater using optimized conditions. The coated capsules are coated with aqueous or solvent coating solution of "polymers" (pH 5.5 to 6.2 sensitive coating) in a coating pan or fluid bed drier/coater using optimized conditions. The pH 5.5 to 6.2 enteric coated (EC) capsules are coated (barrier) with aqueous or solvent coating solution of HPMC or equivalent "polymers" in a coating pan or fluid bed drier/coater using optimized conditions. The pH 5.5 to 6.2 EC capsules are coated with aqueous or solvent coating solution of "polymers" (pH 7.2 to 7.6 sensitive coating) in a coating pan or fluid bed drier/coater using optimized conditions. Finally, the pH 7.2 to 7.6 EC capsules are seal coated with aqueous or solvent coating solution of HPMC or equivalent "polymers" in a coating pan or fluid bed drier/coater using optimized conditions. The small pH 7.2 to 7.6 EC capsules along with a portion of the excipients are filled into a larger hard gelatin capsules using encapsulating equipment. These large capsules are coated (barrier coat) with aqueous or solvent coating solution of HPMC or equivalent "polymers" in a coating pan or fluid bed drier/coater using optimized conditions. The coated capsules are further coated with aqueous or solvent coating solution of "polymers" (pH 7.2 to 7.6 sensitive coating) in a coating pan or fluid bed drier/coater using optimized conditions. Finally, the EC capsules are seal coated with aqueous or solvent coating solution of HPMC or equivalent "polymers" in a coating pan or fluid bed drier/coater using optimized conditions Example final product—capsule-in-capsule (liquid/powder filled)—formulation/manufacturing process (at local CMO, controlled room and humidity conditions throughout the process):

| Ingredients | Amount (%) |
|---|---|
| Dried vaccine powder intermediate formulation | 7% |
| Excipients (Microcrystalline cellulose - filler, Silicon dioxide - glidant/flow aid) | 5% |
| Vegetable oil | 55% |
| Gelatin as a powder (soft gelatin) | 5% |
| Hard gelatin or HPMC capsules | 5% |
| HPMC or equivalent "polymers" (Barrier coat) | 1% |
| "Polymers" (pH 5.5 to 6.2 sensitive coating) | 10% |
| HPMC or equivalent "polymers" (Barrier coat) | 1% |
| "Polymers" (pH 7.2 to 7.6 sensitive coating) | 10% |
| HPMC or equivalent "polymers" (Seal coat) | 1% |
| Water/solvents as required | 0% |

The dried vaccine powder intermediate formulation is blended in desired portions with vegetable oil (immiscible liquid) in a blender. The liquid is filled into small soft or hard gelatin/HPMC capsules using soft or hard gelatin encapsulating equipment. The above capsules are coated (barrier coat) with aqueous or solvent coating solution of HPMC or equivalent "polymers" in a coating pan or fluid bed drier/coater using optimized conditions. The coated capsules are coated with aqueous or solvent coating solution of "polymers" (pH 5.5 to 6.2 sensitive coating) in a coating pan or fluid bed drier/coater using optimized conditions. The pH 5.5 to 6.2 enteric coated (EC) capsules are coated (barrier) with aqueous or solvent coating solution of HPMC or equivalent "polymers" in a coating pan or fluid bed drier/coater using optimized conditions. The pH 5.5 to 6.2 EC capsules are with coated aqueous or solvent coating solution of "polymers" (pH 7.2 to 7.6 sensitive coating) in a coating pan or fluid bed drier/coater using optimized conditions. Finally, the pH 7.2 to 7.6 EC capsules are seal coated with aqueous or solvent coating solution of HPMC or equivalent "polymers" in a coating pan or fluid bed drier/coater using optimized conditions. The small liquid-filled pH 7.2 to 7.6 EC capsules along with a portion of the excipients are filled into a larger hard gelatin capsules using encapsulating equipment. These large capsules are coated (barrier coat) with aqueous or solvent coating solution of HPMC or equivalent "polymers" in a coating pan or fluid bed drier/coater using optimized conditions. The coated capsules are further coated with aqueous or solvent coating solution of "polymers" (pH 7.2 to 7.6 sensitive coating) in a coating pan or fluid bed drier/coater using optimized conditions. Finally, the EC capsules are seal coated with aqueous or solvent coating solution of HPMC or equivalent "polymers" in a coating pan or fluid bed drier/coater using optimized conditions Example final product—capsule/capsule (co-pack)—formulation/manufacturing process (at local CMO, controlled room and humidity conditions throughout the process):

| Ingredients | Amount (%) |
|---|---|
| Dried vaccine powder intermediate formulation | 10% |
| Excipients (Microcrystalline cellulose - filler, Silicon dioxide - glidant/flow aid) | 58% |
| Hard gelatin or HPMC capsules | 9% |
| HPMC or equivalent "polymers" (Barrier coat) | 1% |
| "Polymers" (pH 5.5 to 6.2 sensitive coating) | 10% |
| HPMC or equivalent "polymers" (Barrier coat) | 1% |
| "Polymers" (pH 7.2 to 7.6 sensitive coating) | 10% |
| HPMC or equivalent "polymers" (Seal coat) | 1% |
| Water/solvents as required | 0% |

A portion of the above dried vaccine powder intermediate formulation, and a portion of excipients are blended in a V-type or similar blender. The blended powders are filled into HPMC capsules using encapsulating equipment. The above capsules are coated (barrier coat) with aqueous or solvent coating solution of HPMC or equivalent "polymers" in a coating pan or fluid bed drier/coater using optimized conditions. The coated capsules are coated with aqueous or solvent coating solution of "polymers" (pH 5.5 to 6.2 sensitive coating) in a coating pan or fluid bed drier/coater using optimized conditions. The pH 5.5 to 6.2 enteric coated (EC) capsules are coated (barrier) with aqueous or solvent coating solution of HPMC or equivalent "polymers" in a coating pan or fluid bed drier/coater using optimized conditions. The pH 5.5 to 6.2 EC capsules are coated with aqueous or solvent coating solution of "polymers" (pH 7.2 to 7.6 sensitive coating) in a coating pan or fluid bed drier/coater using optimized conditions. Finally, the pH 7.2 to 7.6 EC capsules are seal coated with aqueous or solvent coating solution of HPMC or equivalent "polymers" in a coating pan or fluid bed drier/coater using optimized conditions. Remaining portion of the above dried vaccine powder intermediate formulation, and excipients are blended in a V-type or similar blender. The blended powders are filled into hard gelatin/HPMC capsules using encapsulating equipment. These capsules are coated (barrier coat) with aqueous or solvent coating solution of HPMC or equivalent "polymers" in a coating pan or fluid bed drier/coater using optimized conditions. The coated capsules are further coated with aqueous or solvent coating solution of "polymers" (pH 7.2 to 7.6 sensitive coating) in a coating pan or fluid bed drier/coater using optimized conditions. Finally, the EC capsules are seal coated with aqueous or solvent coating solution of HPMC or equivalent "polymers" in a coating pan or fluid bed drier/coater using optimized conditions. The two capsule products are co-packed in a blister (see final product packaging)

Example final product capsule/capsule co-pack (liquid/powder filled)—formulation/manufacturing process (at local CMO, controlled room and humidity conditions throughout the process):

| Ingredients | Amount (%) |
|---|---|
| Dried vaccine powder intermediate formulation | 7% |
| Excipients (Microcrystalline cellulose - filler, Silicon dioxide - glidant/flow aid) | 5% |
| Vegetable oil | 55% |
| Gelatin as a powder (soft gelatin) | 5% |
| Hard gelatin or HPMC capsules | 5% |
| HPMC or equivalent "polymers" (Barrier coat) | 1% |
| "Polymers" (pH 5.5 to 6.2 sensitive coating) | 10% |
| HPMC or equivalent "polymers" (Barrier coat) | 1% |
| "Polymers" (pH 7.2 to 7.6 sensitive coating) | 10% |
| HPMC or equivalent "polymers" (Seal coat) | 1% |
| Water/solvents as required | 0% |

A portion of the dried vaccine powder intermediate formulation is blended in with vegetable oil (immiscible liquid) in a blender. The liquid is filled into soft or hard gelatin/HPMC capsules using soft or hard gelatin encapsulating equipment. These capsules are coated (barrier coat) with aqueous or solvent coating solution of HPMC or equivalent "polymers" in a coating pan or fluid bed drier/coater using optimized conditions. The coated capsules are coated with aqueous or solvent coating solution of "polymers" (pH 5.5 to 6.2 sensitive coating) in a coating pan or fluid bed drier/coater using optimized conditions. The pH 5.5 to 6.2 enteric coated (EC) capsules are coated (barrier) with aqueous or solvent coating solution of HPMC or equivalent "polymers" in a coating pan or fluid bed drier/coater using optimized conditions. The pH 5.5 to 6.2 EC capsules are coated with aqueous or solvent coating solution of "polymers" (pH 7.2 to 7.6 sensitive coating) in a coating pan or fluid bed drier/coater using optimized conditions. Finally, the pH 7.2 to 7.6 EC capsules are seal coated with aqueous or solvent coating solution of HPMC or equivalent "polymers" in a coating pan or fluid bed drier/coater using optimized conditions.

The remaining portion of the above dried vaccine powder intermediate formulation, and excipients are blended in a V-type or similar blender. The blended powders are filled into hard gelatin/HPMC capsules using encapsulating equipment. These capsules are coated (barrier coat) with aqueous or solvent coating solution of HPMC or equivalent "polymers" in a coating pan or fluid bed drier/coater using optimized conditions. The coated capsules are further coated with aqueous or solvent coating solution of "polymers" (pH 7.2 to 7.6 sensitive coating) in a coating pan or fluid bed drier/coater using optimized conditions. Finally, the EC capsules are seal coated with aqueous or solvent coating solution of HPMC or equivalent "polymers" in a coating pan or fluid bed drier/coater using optimized conditions. The two capsule products are co-packed in a blister (see final product packaging)

Example final product capsule/capsule co-pack (both liquid filled)—formulation/manufacturing process (at local CMO, controlled room and humidity conditions throughout the process):

| Ingredients | Amount (%) |
|---|---|
| Dried vaccine powder intermediate formulation | 7% |
| Vegetable oil | 60% |
| Gelatin as a powder (soft gelatin) | 5% |
| Hard gelatin or HPMC capsules | 5% |
| HPMC or equivalent "polymers" (Barrier coat) | 1% |
| "Polymers" (pH 5.5 to 6.2 sensitive coating) | 10% |
| HPMC or equivalent "polymers" (Barrier coat) | 1% |
| "Polymers" (pH 7.2 to 7.6 sensitive coating) | 10% |
| HPMC or equivalent "polymers" (Seal coat) | 1% |
| Water/solvents as required | 0% |

A portion of the dried vaccine powder intermediate formulation is blended in with vegetable oil (immiscible liquid) in a blender. The liquid is filled into soft or hard gelatin/HPMC capsules using soft or hard gelatin encapsulating equipment. These capsules are coated (barrier coat) with aqueous or solvent coating solution of HPMC or equivalent "polymers" in a coating pan or fluid bed drier/coater using optimized conditions. The coated capsules are coated with aqueous or solvent coating solution of "polymers" (pH 5.5 to 6.2 sensitive coating) in a coating pan or fluid bed drier/coater using optimized conditions. The pH 5.5 to 6.2 enteric coated (EC) capsules are coated (barrier) with aqueous or solvent coating solution of HPMC or equivalent "polymers" in a coating pan or fluid bed drier/coater using optimized conditions. The pH 5.5 to 6.2 EC capsules are coated with aqueous or solvent coating solution of "polymers" (pH 7.2 to 7.6 sensitive coating) in a coating pan or fluid bed drier/coater using optimized conditions. Finally, the pH 7.2 to 7.6 EC capsules are seal coated with aqueous or solvent coating solution of HPMC or equivalent "polymers" in a coating pan or fluid bed drier/coater using optimized conditions.

The remaining portion of the above dried vaccine powder intermediate formulation is blended in with vegetable oil (immiscible liquid) in a blender. The liquid is filled into soft or hard gelatin/HPMC capsules using soft or hard gelatin encapsulating equipment. These capsules are coated (barrier coat) with aqueous or solvent coating solution of HPMC or equivalent "polymers" in a coating pan or fluid bed drier/coater using optimized conditions. The coated capsules are further coated with aqueous or solvent coating solution of "polymers" (pH 7.2 to 7.6 sensitive coating) in a coating pan or fluid bed drier/coater using optimized conditions. Finally, the EC capsules are seal coated with aqueous or solvent coating solution of HPMC or equivalent "polymers" in a coating pan or fluid bed drier/coater using optimized conditions. The two capsule products are co-packed in a blister (see final product packaging)

Example final product capsule-in-capsule (liquid filled)—formulation/manufacturing process (at local CMO, controlled room and humidity conditions throughout the process):

| Ingredients | Amount (%) |
| --- | --- |
| Dried vaccine powder intermediate formulation | 7% |
| Excipients (Microcrystalline cellulose - filler, Silicon dioxide - glidant/flow aid) | 5% |
| Vegetable oil | 55% |
| Gelatin as a powder (soft gelatin) | 5% |
| Hard gelatin or HPMC capsules (small and large) | 5% |
| HPMC or equivalent "polymers" (Barrier coat) | 1% |
| "Polymers" (pH 5.5 to 6.2 sensitive coating) | 10% |
| HPMC or equivalent "polymers" (Barrier coat) | 1% |
| "Polymers" (pH 7.2 to 7.6 sensitive coating) | 10% |
| HPMC or equivalent "polymers" (Seal coat) | 1% |
| Water/solvents as required | 0% |

A portion of the dried vaccine powder intermediate formulation is blended in with vegetable oil (immiscible liquid) in a blender. The liquid is filled into small (~22 microliter capacity) soft or hard gelatin/HPMC capsules using soft or hard gelatin encapsulating equipment. These capsules are coated (barrier coat) with aqueous or solvent coating solution of HPMC or equivalent "polymers" in a coating pan or fluid bed drier/coater using optimized conditions. The coated capsules are coated with aqueous or solvent coating solution of "polymers" (pH 5.5 to 6.2 sensitive coating) in a coating pan or fluid bed drier/coater using optimized conditions. The pH 5.5 to 6.2 enteric coated (EC) capsules are coated (barrier) with aqueous or solvent coating solution of HPMC or equivalent "polymers" in a coating pan or fluid bed drier/coater using optimized conditions. The pH 5.5 to 6.2 EC capsules are coated with aqueous or solvent coating solution of "polymers" (pH 7.2 to 7.6 sensitive coating) in a coating pan or fluid bed drier/coater using optimized conditions. Finally, the pH 7.2 to 7.6 EC capsules are seal coated with aqueous or solvent coating solution of HPMC or equivalent "polymers" in a coating pan or fluid bed drier/coater using optimized conditions.

The remaining portion of the above dried vaccine powder intermediate formulation is blended in with vegetable oil (immiscible liquid) in a blender. The liquid is filled into small (~22 microliter capacity) soft or hard gelatin/HPMC capsules using a soft or hard gelatin encapsulating equipment. These capsules are coated (barrier coat) with aqueous or solvent coating solution of HPMC or equivalent "polymers" in a coating pan or fluid bed drier/coater using optimized conditions. The coated capsules are further coated with aqueous or solvent coating solution of "polymers" (pH 7.2 to 7.6 sensitive coating) in a coating pan or fluid bed drier/coater using optimized conditions. Finally, the EC capsules are seal coated with aqueous or solvent coating solution of HPMC or equivalent "polymers" in a coating pan or fluid bed drier/coater using optimized conditions. The two small soft or hard gelatin/HPMC capsule products are filled along with excipients into a larger or hard gelatin/HPMC capsule using a hard encapsulating equipment Example final product capsule-in-capsule (liquid filled)—formulation/manufacturing process (at local CMO, controlled room and humidity conditions throughout the process):

| Ingredients | Amount (%) |
| --- | --- |
| Dried vaccine powder intermediate formulation | 7% |
| Excipients (Microcrystalline cellulose - filler, Silicon dioxide - glidant/flow aid) | 5% |
| Vegetable oil | 55% |
| Gelatin as a powder (soft gelatin) | 5% |
| Hard gelatin or HPMC capsules (small and large) | 5% |
| HPMC or equivalent "polymers" (Barrier coat) | 1% |
| "Polymers" (pH 5.5 to 6.2 sensitive coating) | 10% |
| HPMC or equivalent "polymers" (Barrier coat) | 1% |
| "Polymers" (pH 7.2 to 7.6 sensitive coating) | 10% |
| HPMC or equivalent "polymers" (Seal coat) | 1% |
| Water/solvents as required | 0% |

A portion of the dried vaccine powder intermediate formulation is blended in with vegetable oil (immiscible liquid) in a blender. The liquid is filled into small (~22 microliter capacity) soft or hard gelatin/HPMC capsules using soft or hard gelatin encapsulating equipment. These capsules are coated (barrier coat) with aqueous or solvent coating solution of HPMC or equivalent "polymers" in a coating pan or fluid bed drier/coater using optimized conditions. The coated capsules are coated with aqueous or solvent coating solution of "polymers" (pH 5.5 to 6.2 sensitive coating) in a coating pan or fluid bed drier/coater using optimized conditions. The pH 5.5 to 6.2 enteric coated (EC) capsules are coated (barrier) with aqueous or solvent coating solution of HPMC or equivalent "polymers" in a coating pan or fluid bed drier/coater using optimized conditions.

The remaining portion of the above dried vaccine powder intermediate formulation is blended in with vegetable oil (immiscible liquid) in a blender. The liquid is filled into small (~22 microliter capacity) soft or hard gelatin/HPMC capsules using soft or hard gelatin encapsulating equipment. The two small soft or hard gelatin/HPMC capsule products are filled along with excipients into a larger or hard gelatin/HPMC capsule using a soft or hard encapsulating apparatus. The larger capsules are coated with aqueous or solvent coating solution of "polymers" (pH 7.2 to 7.6 sensitive coating) in a coating pan or fluid bed drier/coater using optimized conditions. Finally, the pH 7.2 to 7.6 EC capsules are seal coated with aqueous or solvent coating solution of HPMC or equivalent "polymers" in a coating pan or fluid bed drier/coater using optimized conditions.

Final product packaging (at local CMO, dry low humidity and low oxygen (N2 purging) conditions throughout the process):

The above coated capsules are packaged into bottles with induction sealing or blistered at low humidity (at or below 40% RH) and controlled room temperature conditions (at 20 to 25 degrees c). They may also be blistered in blister-packaging machine Quality Control Release Testing (Active Pharmaceutical Ingredient (API) and Final Drug Product)
Vaccine—

Example 6

Oral Ovarian Cancer Vaccine Formulation Targeting Ileum and Appendix

Ovarian Cancer Vaccine with ileum and appendix delivery, source of vaccine material:
  surgically removed ovarian tumor antigens are captured from the Originating patient and processed for return use in the originating patient
  assurance that antigens used are not in themselves oncogenic
  Mixtures of surgically removed and processed antigens from several patients given to new tumor bearing but vaccine-naive patients
  Captured circulating antigens and/or metastatic cells from the blood of one or more patients, processed for oral vaccination of the index patient or mixed for use in new tumor bearing but vaccine-naive patients
Ovarian Cancer Antigen for Human use: rCNP—NY-ESO-1/TRICOM for ileal and Right Colon/Appendix targeting
Adjuvants can be added to the formulation such as Heat Shock Proteins

| Tests | Methods and assessment |
|---|---|
| Description | Granules, pellets, capsules in blisters or bottles, etc. |
| Appearance | Visual inspection for color, shape, etc. |
| Identification | Genes, species, strains. Morphological appearance via microscopic evaluation and/or multiplex PCR as well as other tests including biochemical methods such as fermentation profile or genotypic methods. In addition, develop a specific identity assay for critical biological activity. Others test may include: DNA-DNA hybridization to specify strains in species; DNA sequence coding per who; strain typing include pulsed field gel electrophoresis (PFGE), etc. |
| Potency - viable organisms | Microscopic testing, or opacity to measure viable cells per unit or dose, i.e. Colony forming units (cfu) |
| Potency assay | Assessment of cfu (e.g. On solid medium) and tests to correlating with activity. M-viability plating or other in-vitro testing methods. |
| Purity | Endotoxin content, residual antibiotics, and/or the quantification of residual toxic components or contaminants introduced during manufacture by Elisa or amino acid profile |
| Microbial bioburden or contaminants and limits | Extraneous materials including pathogens by using Elisa or amino acid profile or SDS page or ion exchange chromatography, etc. Microbial limits by us pharmacopeia (USP31 <61>). |
| Percent viable cells | Micro testing after regrown in appropriate media and tests, e.g., dead/live assay by ATP. Also determination of non-viable units per g i.e., by electro-zone count of non-fluorescent cells (SDS page) |
| Particulate matter | USP31 <788> |
| Pyrogens | Rabbit pyrogencity test (USP31 <151>) |
| PH testing | PH meter |
| Residual moisture | Water content, USP31 <921> |
| Content uniformity | Atp or other assay methodology |
| Package integrity | Leaker test by vacuum |
| Stability | Potency, viable cell determination, microbial contamination, pH an residual moisture |
| In-vitro release testing (via dissolution testing equipment): USPpaddle or basket | Medium: pH 1 buffer (simulated gastric), pH 6 buffer, pH 7.2 to 7.6 buffer (simulated intestinal fluid), followed by pH 5.5-6.2 buffer (simulated colonic fluid). Sample times: PH 1 buffer - 1 hour PH 6 buffer - 1 hour PH 7.2 to 7.6 - 1, 2, 3 and 4 hours PH 5.5 to 6.2 - 1, 2, 4 and 8 hours Vaccine assay: Microbiology testing for count (cfu/gram) and other special technology |
| Stability testing (0, 6, 12, 18 and 24 months): | Vaccine: Identification, potency, viable cell determination, microbial contamination, pH and residual moisture, etc. |

Any or all of the above inner pill strategies combined with use of outer pill substances in formulations which enhance immune system functions in the GI-Pancreatic-Hepatic axis.

Outer Pill can be vaccine in combination with adjuvants; inner pill targeting the appendix can be a vaccine with or without an adjuvant.

Target delivery: vaccine (Ovarian Cancer Antigen for Human use: rCNP—NY-ESO-1/TRICOM for ileal and Right Colon/Appendix targeting with/or without adjuvants with "l-leucine" as a pharmaceutical aid) for delivery in ileum at pH 7.3 to 7.6 and appendix at pH 5.5-6.2

Materials and Methods:

Active Pharmaceutical Ingredient (API):

Ovarian Cancer Antigen for Human use: rCNP—NY-ESO-1/TRICOM is provided by high quality global suppliers L-leucine (dispersibility aid)—supplied by Ajinomoto and Tyloxapol, USP (Anti-clumping aid) supplied by Sigma Aldrich Inactive ingredients (excipients)—microcrystalline cellulose, lactose, pregelatinized starch, silicon dioxide, HPMC or equivalent "polymers", hard gelatin or HPMC capsules, gelatin, vegetable oil and other fillers, etc.—purchased from local us supplier such as FMC, Capsugel, Colorcon, Evonik, etc.

Intermediate formulation/manufacturing process (at local CMO, controlled room and humidity conditions throughout the process):

"Dried vaccine powder (10-100 microns) intermediate formulation"

| Ingredients | Amount (%) |
| --- | --- |
| rCNP - NY-ESO-1/TRICOM | 5% |
| L-leucine | 95% |
| Water as required | 0% |

Prepared by mixing l-leucine, and rCNP—NY-ESO-1/TRICOM with water and freeze/spray dried in freeze/spray drier to remove water.

Example final product—capsule-in-capsule (hard gelatin)—formulation/manufacturing process (at local CMO, controlled room and humidity conditions throughout the process):

| Ingredients | Amount (%) |
| --- | --- |
| Dried vaccine powder intermediate formulation | 10% |
| Excipients (Microcrystalline cellulose - filler, Silicon dioxide - glidant/flow aid) | 58% |
| Hard gelatin or HPMC capsules | 9% |
| HPMC or equivalent "polymers" (Barrier coat) | 1% |
| "Polymers" (pH 5.5 to 6.2 sensitive coating) | 10% |
| HPMC or equivalent "polymers" (Barrier coat) | 1% |
| "Polymers" (pH 7.2 to 7.6 sensitive coating) | 10% |
| HPMC or equivalent "polymers" (Seal coat) | 1% |
| Water/solvents as required | 0% |

The above dried vaccine powder intermediate formulation, and a portion of excipients are blended in a V-type or similar blender. The blended powders are filled into small (~22 microliter capacity) HPMC capsules using encapsulating equipment. The capsules are coated (barrier coat) with aqueous or solvent coating solution of HPMC or equivalent "polymers" in a coating pan or fluid bed drier/coater using optimized conditions. The coated capsules are coated with aqueous or solvent coating solution of "polymers" (pH 5.5 to 6.2 sensitive coating) in a coating pan or fluid bed drier/coater using optimized conditions. The pH 5.5 to 6.2 enteric coated (EC) capsules are coated (barrier) with aqueous or solvent coating solution of HPMC or equivalent "polymers" in a coating pan or fluid bed drier/coater using optimized conditions. The pH 5.5 to 6.2 EC capsules are coated with aqueous or solvent coating solution of "polymers" (pH 7.2 to 7.6 sensitive coating) in a coating pan or fluid bed drier/coater using optimized conditions. Finally, the pH 7.2 to 7.6 EC capsules are seal coated with aqueous or solvent coating solution of HPMC or equivalent "polymers" in a coating pan or fluid bed drier/coater using optimized conditions. The small pH 7.2 to 7.6 EC capsules along with a portion of the excipients are filled into a larger hard gelatin capsules using encapsulating equipment. These large capsules are coated (barrier coat) with aqueous or solvent coating solution of HPMC or equivalent "polymers" in a coating pan or fluid bed drier/coater using optimized conditions. The coated capsules are further coated with aqueous or solvent coating solution of "polymers" (pH 7.2 to 7.6 sensitive coating) in a coating pan or fluid bed drier/coater using optimized conditions. Finally, the EC capsules are seal coated with aqueous or solvent coating solution of HPMC or equivalent "polymers" in a coating pan or fluid bed drier/coater using optimized conditions Example final product—capsule-in-capsule (liquid/powder filled)—formulation/manufacturing process (at local CMO, controlled room and humidity conditions throughout the process):

| Ingredients | Amount (%) |
| --- | --- |
| Dried vaccine powder intermediate formulation | 7% |
| Excipients (Microcrystalline cellulose - filler, Silicon dioxide - glidant/flow aid) | 5% |
| Vegetable oil | 55% |
| Gelatin as a powder (soft gelatin) | 5% |
| Hard gelatin or HPMC capsules | 5% |
| HPMC or equivalent "polymers" (Barrier coat) | 1% |
| "Polymers" (pH 5.5 to 6.2 sensitive coating) | 10% |
| HPMC or equivalent "polymers" (Barrier coat) | 1% |
| "Polymers" (pH 7.2 to 7.6 sensitive coating) | 10% |
| HPMC or equivalent "polymers" (Seal coat) | 1% |
| Water/solvents as required | 0% |

The dried vaccine powder intermediate formulation is blended in desired portions with vegetable oil (immiscible liquid) in a blender. The liquid is filled into small soft or hard gelatin/HPMC capsules using soft or hard gelatin encapsulating equipment. The above capsules are coated (barrier coat) with aqueous or solvent coating solution of HPMC or equivalent "polymers" in a coating pan or fluid bed drier/coater using optimized conditions. The coated capsules are coated with aqueous or solvent coating solution of "polymers" (pH 5.5 to 6.2 sensitive coating) in a coating pan or fluid bed drier/coater using optimized conditions. The pH 5.5 to 6.2 enteric coated (EC) capsules are coated (barrier) with aqueous or solvent coating solution of HPMC or equivalent "polymers" in a coating pan or fluid bed drier/coater using optimized conditions. The pH 5.5 to 6.2 EC capsules are with coated aqueous or solvent coating solution of "polymers" (pH 7.2 to 7.6 sensitive coating) in a coating pan or fluid bed drier/coater using optimized conditions. Finally, the pH 7.2 to 7.6 EC capsules are seal coated with aqueous or solvent coating solution of HPMC or equivalent "polymers" in a coating pan or fluid bed drier/coater using optimized conditions. The small liquid-filled pH 7.2 to 7.6

EC capsules along with a portion of the excipients are filled into a larger hard gelatin capsules using an encapsulating equipment. These large capsules are coated (barrier coat) with aqueous or solvent coating solution of HPMC or equivalent "polymers" in a coating pan or fluid bed drier/coater using optimized conditions. The coated capsules are further coated with aqueous or solvent coating solution of "polymers" (pH 7.2 to 7.6 sensitive coating) in a coating pan or fluid bed drier/coater using optimized conditions. Finally, the EC capsules are seal coated with aqueous or solvent coating solution of HPMC or equivalent "polymers" in a coating pan or fluid bed drier/coater using optimized conditions Example final product—capsule/capsule (co-pack)—formulation/manufacturing process (at local CMO, controlled room and humidity conditions throughout the process):

| Ingredients | Amount (%) |
| --- | --- |
| Dried vaccine powder intermediate formulation | 10% |
| Excipients (Microcrystalline cellulose - filler, Silicon dioxide - glidant/flow aid) | 58% |
| Hard gelatin or HPMC capsules | 9% |
| HPMC or equivalent "polymers" (Barrier coat) | 1% |
| "Polymers" (pH 5.5 to 6.2 sensitive coating) | 10% |
| HPMC or equivalent "polymers" (Barrier coat) | 1% |
| "Polymers" (pH 7.2 to 7.6 sensitive coating) | 10% |
| HPMC or equivalent "polymers" (Seal coat) | 1% |
| Water/solvents as required | 0% |

A portion of the above dried vaccine powder intermediate formulation, and a portion of excipients are blended in a V-type or similar blender. The blended powders are filled into HPMC capsules using encapsulating equipment. The above capsules are coated (barrier coat) with aqueous or solvent coating solution of HPMC or equivalent "polymers" in a coating pan or fluid bed drier/coater using optimized conditions. The coated capsules are coated with aqueous or solvent coating solution of "polymers" (pH 5.5 to 6.2 sensitive coating) in a coating pan or fluid bed drier/coater using optimized conditions. The pH 5.5 to 6.2 enteric coated (EC) capsules are coated (barrier) with aqueous or solvent coating solution of HPMC or equivalent "polymers" in a coating pan or fluid bed drier/coater using optimized conditions. The pH 5.5 to 6.2 EC capsules are coated with aqueous or solvent coating solution of "polymers" (pH 7.2 to 7.6 sensitive coating) in a coating pan or fluid bed drier/coater using optimized conditions. Finally, the pH 7.2 to 7.6 EC capsules are seal coated with aqueous or solvent coating solution of HPMC or equivalent "polymers" in a coating pan or fluid bed drier/coater using optimized conditions.

Remaining portion of the above dried vaccine powder intermediate formulation, and excipients are blended in a V-type or similar blender. The blended powders are filled into hard gelatin/HPMC capsules using encapsulating equipment. These capsules are coated (barrier coat) with aqueous or solvent coating solution of HPMC or equivalent "polymers" in a coating pan or fluid bed drier/coater using optimized conditions. The coated capsules are further coated with aqueous or solvent coating solution of "polymers" (pH 7.2 to 7.6 sensitive coating) in a coating pan or fluid bed drier/coater using optimized conditions. Finally, the EC capsules are seal coated with aqueous or solvent coating solution of HPMC or equivalent "polymers" in a coating pan or fluid bed drier/coater using optimized conditions. The two capsule products are co-packed in a blister (see final product packaging)

Example final product capsule/capsule co-pack (liquid/powder filled)—formulation/manufacturing process (at local CMO, controlled room and humidity conditions throughout the process):

| Ingredients | Amount (%) |
| --- | --- |
| Dried vaccine powder intermediate formulation | 7% |
| Excipients (Microcrystalline cellulose - filler, Silicon dioxide - glidant/flow aid) | 5% |
| Vegetable oil | 55% |
| Gelatin as a powder (soft gelatin) | 5% |
| Hard gelatin or HPMC capsules | 5% |
| HPMC or equivalent "polymers" (Barrier coat) | 1% |
| "Polymers" (pH 5.5 to 6.2 sensitive coating) | 10% |
| HPMC or equivalent "polymers" (Barrier coat) | 1% |
| "Polymers" (pH 7.2 to 7.6 sensitive coating) | 10% |
| HPMC or equivalent "polymers" (Seal coat) | 1% |
| Water/solvents as required | 0% |

A portion of the dried vaccine powder intermediate formulation is blended in with vegetable oil (immiscible liquid) in a blender. The liquid is filled into soft or hard gelatin/HPMC capsules using soft or hard gelatin encapsulating equipment. These capsules are coated (barrier coat) with aqueous or solvent coating solution of HPMC or equivalent "polymers" in a coating pan or fluid bed drier/coater using optimized conditions. The coated capsules are coated with aqueous or solvent coating solution of "polymers" (pH 5.5 to 6.2 sensitive coating) in a coating pan or fluid bed drier/coater using optimized conditions. The pH 5.5 to 6.2 enteric coated (EC) capsules are coated (barrier) with aqueous or solvent coating solution of HPMC or equivalent "polymers" in a coating pan or fluid bed drier/coater using optimized conditions. The pH 5.5 to 6.2 EC capsules are coated with aqueous or solvent coating solution of "polymers" (pH 7.2 to 7.6 sensitive coating) in a coating pan or fluid bed drier/coater using optimized conditions. Finally, the pH 7.2 to 7.6 EC capsules are seal coated with aqueous or solvent coating solution of HPMC or equivalent "polymers" in a coating pan or fluid bed drier/coater using optimized conditions.

The remaining portion of the above dried vaccine powder intermediate formulation, and excipients are blended in a V-type or similar blender. The blended powders are filled into hard gelatin/HPMC capsules using encapsulating equipment. These capsules are coated (barrier coat) with aqueous or solvent coating solution of HPMC or equivalent "polymers" in a coating pan or fluid bed drier/coater using optimized conditions. The coated capsules are further coated with aqueous or solvent coating solution of "polymers" (pH 7.2 to 7.6 sensitive coating) in a coating pan or fluid bed drier/coater using optimized conditions. Finally, the EC capsules are seal coated with aqueous or solvent coating solution of HPMC or equivalent "polymers" in a coating pan or fluid bed drier/coater using optimized conditions. The two capsule products are co-packed in a blister (see final product packaging)

Example final product capsule/capsule co-pack (both liquid filled)—formulation/manufacturing process (at local CMO, controlled room and humidity conditions throughout the process):

| Ingredients | Amount (%) |
| --- | --- |
| Dried vaccine powder intermediate formulation | 7% |
| Vegetable oil | 60% |

-continued

| Ingredients | Amount (%) |
| --- | --- |
| Gelatin as a powder (soft gelatin) | 5% |
| Hard gelatin or HPMC capsules | 5% |
| HPMC or equivalent "polymers" (Barrier coat) | 1% |
| "Polymers" (pH 5.5 to 6.2 sensitive coating) | 10% |
| HPMC or equivalent "polymers" (Barrier coat) | 1% |
| "Polymers" (pH 7.2 to 7.6 sensitive coating) | 10% |
| HPMC or equivalent "polymers" (Seal coat) | 1% |
| Water/solvents as required | 0% |

A portion of the dried vaccine powder intermediate formulation is blended in with vegetable oil (immiscible liquid) in a blender. The liquid is filled into soft or hard gelatin/HPMC capsules using soft or hard gelatin encapsulating equipment. These capsules are coated (barrier coat) with aqueous or solvent coating solution of HPMC or equivalent "polymers" in a coating pan or fluid bed drier/coater using optimized conditions. The coated capsules are coated with aqueous or solvent coating solution of "polymers" (pH 5.5 to 6.2 sensitive coating) in a coating pan or fluid bed drier/coater using optimized conditions. The pH 5.5 to 6.2 enteric coated (EC) capsules are coated (barrier) with aqueous or solvent coating solution of HPMC or equivalent "polymers" in a coating pan or fluid bed drier/coater using optimized conditions. The pH 5.5 to 6.2 EC capsules are coated with aqueous or solvent coating solution of "polymers" (pH 7.2 to 7.6 sensitive coating) in a coating pan or fluid bed drier/coater using optimized conditions. Finally, the pH 7.2 to 7.6 EC capsules are seal coated with aqueous or solvent coating solution of HPMC or equivalent "polymers" in a coating pan or fluid bed drier/coater using optimized conditions.

The remaining portion of the above dried vaccine powder intermediate formulation is blended in with vegetable oil (immiscible liquid) in a blender. The liquid is filled into soft or hard gelatin/HPMC capsules using soft or hard gelatin encapsulating equipment. These capsules are coated (barrier coat) with aqueous or solvent coating solution of HPMC or equivalent "polymers" in a coating pan or fluid bed drier/coater using optimized conditions. The coated capsules are further coated with aqueous or solvent coating solution of "polymers" (pH 7.2 to 7.6 sensitive coating) in a coating pan or fluid bed drier/coater using optimized conditions. Finally, the EC capsules are seal coated with aqueous or solvent coating solution of HPMC or equivalent "polymers" in a coating pan or fluid bed drier/coater using optimized conditions. The two capsule products are co-packed in a blister (see final product packaging)

Example final product capsule-in-capsule (liquid filled)—formulation/manufacturing process (at local CMO, controlled room and humidity conditions throughout the process):

| Ingredients | Amount (%) |
| --- | --- |
| Dried vaccine powder intermediate formulation | 7% |
| Excipients (Microcrystalline cellulose - filler, Silicon dioxide - glidant/flow aid) | 5% |
| Vegetable oil | 55% |
| Gelatin as a powder (soft gelatin) | 5% |
| Hard gelatin or HPMC capsules (small and large) | 5% |
| HPMC or equivalent "polymers" (Barrier coat) | 1% |
| "Polymers" (pH 5.5 to 6.2 sensitive coating) | 10% |
| HPMC or equivalent "polymers" (Barrier coat) | 1% |
| "Polymers" (pH 7.2 to 7.6 sensitive coating) | 10% |
| HPMC or equivalent "polymers" (Seal coat) | 1% |
| Water/solvents as required | 0% |

A portion of the dried vaccine powder intermediate formulation is blended in with vegetable oil (immiscible liquid) in a blender. The liquid is filled into small (~22 microliter capacity) soft or hard gelatin/HPMC capsules using soft or hard gelatin encapsulating equipment. These capsules are coated (barrier coat) with aqueous or solvent coating solution of HPMC or equivalent "polymers" in a coating pan or fluid bed drier/coater using optimized conditions. The coated capsules are coated with aqueous or solvent coating solution of "polymers" (pH 5.5 to 6.2 sensitive coating) in a coating pan or fluid bed drier/coater using optimized conditions. The pH 5.5 to 6.2 enteric coated (EC) capsules are coated (barrier) with aqueous or solvent coating solution of HPMC or equivalent "polymers" in a coating pan or fluid bed drier/coater using optimized conditions. The pH 5.5 to 6.2 EC capsules are coated with aqueous or solvent coating solution of "polymers" (pH 7.2 to 7.6 sensitive coating) in a coating pan or fluid bed drier/coater using optimized conditions. Finally, the pH 7.2 to 7.6 EC capsules are seal coated with aqueous or solvent coating solution of HPMC or equivalent "polymers" in a coating pan or fluid bed drier/coater using optimized conditions.

The remaining portion of the above dried vaccine powder intermediate formulation is blended in with vegetable oil (immiscible liquid) in a blender. The liquid is filled into small (~22 microliter capacity) soft or hard gelatin/HPMC capsules using a soft or hard gelatin encapsulating equipment. These capsules are coated (barrier coat) with aqueous or solvent coating solution of HPMC or equivalent "polymers" in a coating pan or fluid bed drier/coater using optimized conditions. The coated capsules are further coated with aqueous or solvent coating solution of "polymers" (pH 7.2 to 7.6 sensitive coating) in a coating pan or fluid bed drier/coater using optimized conditions. Finally, the EC capsules are seal coated with aqueous or solvent coating solution of HPMC or equivalent "polymers" in a coating pan or fluid bed drier/coater using optimized conditions. The two small soft or hard gelatin/HPMC capsule products are filled along with excipients into a larger or hard gelatin/HPMC capsule using a hard encapsulating equipment Example final product capsule-in-capsule (liquid filled)—formulation/manufacturing process (at local CMO, controlled room and humidity conditions throughout the process):

| Ingredients | Amount (%) |
| --- | --- |
| Dried vaccine powder intermediate formulation | 7% |
| Excipients (Microcrystalline cellulose - filler, Silicon dioxide - glidant/flow aid) | 5% |
| Vegetable oil | 55% |
| Gelatin as a powder (soft gelatin) | 5% |
| Hard gelatin or HPMC capsules (small and large) | 5% |
| HPMC or equivalent "polymers" (Barrier coat) | 1% |
| "Polymers" (pH 5.5 to 6.2 sensitive coating) | 10% |
| HPMC or equivalent "polymers" (Barrier coat) | 1% |
| "Polymers" (pH 7.2 to 7.6 sensitive coating) | 10% |
| HPMC or equivalent "polymers" (Seal coat) | 1% |
| Water/solvents as required | 0% |

A portion of the dried vaccine powder intermediate formulation is blended in with vegetable oil (immiscible liquid) in a blender. The liquid is filled into small (~22 microliter capacity) soft or hard gelatin/HPMC capsules using soft or hard gelatin encapsulating equipment. These capsules are coated (barrier coat) with aqueous or solvent coating solution of HPMC or equivalent "polymers" in a coating pan or fluid bed drier/coater using optimized conditions. The coated capsules are coated with aqueous or solvent coating solution of "polymers" (pH 5.5 to 6.2 sensitive coating) in a coating pan or fluid bed drier/coater using optimized conditions. The pH 5.5 to 6.2 enteric coated (EC) capsules are coated (barrier) with aqueous or solvent coating solution of HPMC or equivalent "polymers" in a coating pan or fluid bed drier/coater using optimized conditions.

The remaining portion of the above dried vaccine powder intermediate formulation is blended in with vegetable oil (immiscible liquid) in a blender. The liquid is filled into small (~22 microliter capacity) soft or hard gelatin/HPMC capsules using soft or hard gelatin encapsulating equipment. The two small soft or hard gelatin/HPMC capsule products are filled along with excipients into a larger or hard gelatin/HPMC capsule using a soft or hard encapsulating equipment. The larger capsules are coated with aqueous or solvent coating solution of "polymers" (pH 7.2 to 7.6 sensitive coating) in a coating pan or fluid bed drier/coater using optimized conditions. Finally, the pH 7.2 to 7.6 EC capsules are seal coated with aqueous or solvent coating solution of HPMC or equivalent "polymers" in a coating pan or fluid bed drier/coater using optimized conditions.

Final product packaging (at local CMO, dry low humidity and low oxygen (N2 purging) conditions throughout the process):

The above coated capsules are packaged into bottles with induction sealing or blistered at low humidity (at or below 40% RH) and controlled room temperature conditions (at 20 to 25 degrees c). They may also be blistered in blister-packaging machine Quality Control Release Testing (Active Pharmaceutical Ingredient (API) and Final Drug Product)
Vaccine—

| Tests | Methods and assessment |
|---|---|
| Description | Capsules in blisters or bottles, etc. |
| Appearance | Visual inspection for color, shape, etc. |
| Identification | Antigen by DNA. |
| Assay | Antigen specific assay methodology |
| Purity | SDS Gel electrophoresis |
| Particulate matter | USP31 <788> |
| Residual moisture | Water content, USP31 <921> |
| Content uniformity | Antigen specific assay methodology |
| Package integrity | Leaker test by vacuum |
| Stability | Assay, purity, microbial contamination, pH and residual moisture |
| In-vitro release testing (via dissolution testing equipment): USP paddle or basket | Medium: pH 1 buffer (simulated gastric), pH 6 buffer, pH 7.2 to 7.6 buffer (simulated intestinal fluid), followed by pH 5.5-6.2 buffer (simulated colonic fluid).<br>Sample times:<br>PH 1 buffer - 1 hour<br>PH 6 buffer - 1 hour<br>PH 7.2 to 7.6 - 1, 2, 3 and 4 hours<br>PH 5.5 to 6.2 - 1, 2, 4 and 8 hours<br>Vaccine assay:<br>Antigen specific assay methodology and/or other special technology |
| Stability testing (0, 6, 12, 18 and 24 months): | Vaccine:<br>Identification, potency, viable cell determination, microbial contamination, pH and residual moisture, etc. |

Example 7

Oral Hepatocellular Cancer Vaccine

Hepatocellular Cancer Vaccine with ileum and appendix delivery:
- surgically removed tumor antigens from the Originating patient and processed for return use in the originating patient
- Mixtures of surgically removed and processed antigens from several patients given to new tumor bearing but vaccine-naive patients
- Captured circulating antigens and/or metastatic cells from the blood of one or more patients, processed for oral vaccination of the index patient or mixed for use in new tumor bearing but vaccine-naive patients
- Adjuvants can be added to the formulation such as Heat Shock Proteins Any or all of the above inner pill strategies combined with use of outer pill adjuvant formulations which enhance immune system functions in the GI-Pancreatic-Hepatic axis.
- Outer Pill can be vaccine material combined with adjuvants; the inner Pill can be vaccine material combined with adjuvants but would not contain any of the ileal brake hormone releasing substances, since they are not necessary for vaccine material amplification by the appendix.

Example 8

Oral Colon Cancer Vaccine

Colon Cancer Vaccine with ileum and appendix delivery:
- surgically removed tumor antigens from the Originating patient and processed for return use in the originating patient
- Mixtures of surgically removed and processed antigens from several patients given to new tumor bearing but vaccine-naive patients
- Captured circulating antigens and/or metastatic cells from the blood of one or more patients, processed for oral vaccination of the index patient or mixed for use in new tumor bearing but vaccine-naive patients
- Adjuvants can be added to the formulation such as Heat Shock Proteins Any or all of the above inner pill strategies combined with use of outer pill ileal release formulations which enhance immune system functions in the GI-Pancreatic-Hepatic axis.
- Outer Pill can be ileal release vaccine constructs with or without adjuvants, inner pill is a vaccine targeted to appendix.

Example 9

Oral Pancreatic Cancer Vaccine

Pancreatic Cancer Vaccine with ileum and appendix delivery:
- surgically removed tumor antigens from the Originating patient and processed for return use in the originating patient
- Mixtures of surgically removed and processed antigens from several patients given to new tumor bearing but vaccine-naive patients
- Captured circulating antigens and/or metastatic cells from the blood of one or more patients, processed for oral vaccination of the index patient or mixed for use in new tumor bearing but vaccine-naive patients
- Adjuvants can be added to the formulation such as Heat Shock Proteins Any or all of the above inner pill strategies combined with use of outer pill ileal release formulations which enhance immune system functions in the GI-Pancreatic-Hepatic axis.

Outer Pill can be ileal release with adjuvants, inner Pill can be a vaccine targeting the appendix.

REFERENCES

1. Akers S N, Odunsi K, Karpf A R. Regulation of cancer germline antigen gene expression: implications for cancer immunotherapy. Future Oncol. 2010; 6(5):717-32.
2. Chen Y T, Hsu M, Lee P, Shin S J, Mhawech-Fauceglia P, Odunsi K, et al. Cancer/testis antigen CT45: analysis of mRNA and protein expression in human cancer. Int J. Cancer. 2009; 124(12):2893-8.
3. Li Q, Eppolito C, Odunsi K, Shrikant P A. Antigen-induced Erkl/2 activation regulates Ets-1-mediated sensitization of CD8+ T cells for IL-12 responses. J Leukoc Biol. 2010; 87(2):257-63.
4. Mhawech-Fauceglia P, Smiraglia D J, Bshara W, Andrews C, Schwaller J, South S, et al. Prostate-specific membrane antigen expression is a potential prognostic marker in endometrial adenocarcinoma. Cancer Epidemiol Biomarkers Prev. 2008; 17(3):571-7.
5. Qian F, Odunsi K, Blatt L M, Scanlan M J, Mannan M, Shah N, et al. Tumor associated antigen recognition by autologous serum in patients with breast cancer. Int J Mol Med. 2005; 15(1):137-44.
6. Tammela J, Jungbluth A A, Qian F, Santiago D, Scanlan M J, Keitz B, et al. SCP-1 cancer/testis antigen is a prognostic indicator and a candidate target for immunotherapy in epithelial ovarian cancer. Cancer Immun. 2004; 4:10.
7. Tsuji T, Matsuzaki J, Kelly M P, Ramakrishna V, Vitale L, He L Z, et al. Antibody-targeted NY-ESO-1 to mannose receptor or DEC-205 in vitro elicits dual human CD8+ and CD4+ T cell responses with broad antigen specificity. J. Immunol. 2011; 186(2):1218-27.
8. Tsuji T, Matsuzaki J, Ritter E, Miliotto A, Ritter G, Odunsi K, et al. Split T cell tolerance against a self/tumor antigen: spontaneous CD4+ but not CD8+ T cell responses against p53 in cancer patients and healthy donors. PLoS One. 2011; 6(8):e23651.
9. Woloszynska-Read A, James S R, Song C, Jin B, Odunsi K, Karpf A R. BORIS/CTCFL expression is insufficient for cancer-germline antigen gene expression and DNA hypomethylation in ovarian cell lines. Cancer Immun. 2010; 10:6.
10. Woloszynska-Read A, Zhang W, Yu J, Link P A, Mhawech-Fauceglia P, Collamat G, et al. Coordinated cancer germline antigen promoter and global DNA hypomethylation in ovarian cancer: association with the BORIS/CTCF expression ratio and advanced stage. Clin Cancer Res. 2011; 17(8):2170-80.
11. Tomaras G D, Binley J M, Gray E S, Crooks E T, Osawa K, Moore P L, et al. Polyclonal B cell responses to conserved neutralization epitopes in a subset of HIV-1-infected individuals. J. Virol. 2011; 85(21):11502-19.
12. Crooks E T, Tong T, Osawa K, Binley J M. Enzyme digests eliminate nonfunctional Env from HIV-1 particle surfaces, leaving native Env trimers intact and viral infectivity unaffected. J. Virol. 2011; 85(12):5825-39.
13. Moir S, Malaspina A, Fauci A S. Prospects for an HIV vaccine: leading B cells down the right path. Nat Struct Mol Biol. 2011; 18(12):1317-21.
14. Moir S, Chun T W, Fauci A S. Pathogenic mechanisms of HIV disease Annu Rev Pathol. 2011; 6:223-48.
15. Moir S, Fauci A S. B cells in HIV infection and disease. Nat Rev Immunol. 2009; 9(4):235-45.
16. Moir S, Ho J, Malaspina A, Wang W, DiPoto A C, O'Shea M A, et al. Evidence for HIV-associated B cell exhaustion in a dysfunctional memory B cell compartment in HIV-infected viremic individuals. J Exp Med. 2008; 205(8):1797-805.
17. Moir S, Malaspina A, Ho J, Wang W, Dipoto A C, O'Shea M A, et al. Normalization of B cell counts and subpopulations after antiretroviral therapy in chronic HIV disease. J Infect Dis. 2008; 197(4):572-9.
18. Moir S, Ogwaro K M, Malaspina A, Vasquez J, Donoghue E T, Hallahan C W, et al. Perturbations in B cell responsiveness to CD4+ T cell help in HIV-infected individuals. Proc Natl Acad Sci USA. 2003; 100(10): 6057-62.
19. Malaspina A, Moir S, Nickle D C, Donoghue E T, Ogwaro K M, Ehler L A, et al. Human immunodeficiency virus type 1 bound to B cells: relationship to virus replicating in CD4+ T cells and circulating in plasma. J. Virol. 2002; 76(17):8855-63.
20. Raghuraman S, Park H, Osburn W O, Winkelstein E, Edlin B R, Rehermann B. Spontaneous clearance of chronic hepatitis C virus infection is associated with appearance of neutralizing antibodies and reversal of T-cell exhaustion. J Infect Dis. 2012; 205(5):763-71.
21. Halliday J, Klenerman P, Barnes E. Vaccination for hepatitis C virus: closing in on an evasive target. Expert Rev Vaccines. 2011; 10(5):659-72.
22. Conry S J, Meng Q, Hardy G, Yonkers N L, Sugalski J M, Hirsch A, et al. Genetically Associated CD16+56—Natural Killer Cell Interferon (IFN)-alphaR Expression Regulates Signaling and Is Implicated in IFN-alpha-Induced Hepatitis C Virus Decline. J Infect Dis. 2012; 205 (7): 1131-41.
23. Grafmueller S, Billerbeck E, Blum H E, Neumann-Haefelin C, Thimme R. Differential Antigen Specificity of Hepatitis C Virus-Specific Interleukin 17- and Interferon gamma-Producing CD8+ T Cells During Chronic Infection. J Infect Dis. 2012; 205(7):1142-6.
24. Rahman F, Heller T, Sobao Y, Mizukoshi E, Nascimbeni M, Alter H, et al. Effects of antiviral therapy on the cellular immune response in acute hepatitis C. Hepatology. 2004; 40(1):87-97.
25. Strickland G T, El-Kamary S S, Klenerman P, Nicosia A. Hepatitis C vaccine: supply and demand. Lancet Infect Dis. 2008; 8(6):379-86.
26. Rajkannan R, Dhanaraju M D, Gopinath D, Selvaraj D, Jayakumar R. Development of hepatitis B oral vaccine using B-cell epitope loaded PLG microparticles. Vaccine. 2006; 24(24):5149-57.
27. Kantele J M, Arvilommi H, Kontiainen S, Salmi M, Jalkanen S, Savilahti E, et al. Mucosally activated circulating human B cells in diarrhea express homing receptors directing them back to the gut. Gastroenterology. 1996; 110(4):1061-7.
28. Hanninen A, Jalkanen S, Salmi M, Toikkanen S, Nikolakaros G, Simell O. Macrophages, T cell receptor usage, and endothelial cell activation in the pancreas at the onset of insulin-dependent diabetes mellitus. J Clin Invest. 1992; 90(5):1901-10.
29. Duijvestijn A, Hamann A. Mechanisms and regulation of lymphocyte migration. Immunol Today. 1989; 10(1):23-8.
30. Hamann A, Thiele H G. Molecules and regulation in lymphocyte migration. Immunol Rev. 1989; 108:19-44.
31. Farstad I N, Halstensen T S, Fausa O, Brandtzaeg P. Heterogeneity of M-cell-associated B and T cells in human Peyer's patches. Immunology. 1994; 83(3):457-64.

32. Halstensen T S, Scott H, Fausa O, Brandtzaeg P. Gluten stimulation of coeliac mucosa in vitro induces activation (CD25) of lamina propria CD4+ T cells and macrophages but no crypt-cell hyperplasia. Scand J. Immunol. 1993; 38(6):581-90.
33. Farstad I N, Halstensen T S, Fausa O, Brandtzaeg P. Do human Peyer's patches contribute to the intestinal intraepithelial gamma/delta T-cell population? Scand J. Immunol. 1993; 38(5):451-8.
34. Nilssen D E, Aukrust P, Froland S S, Muller F, Fausa O, Halstensen T S, et al. Duodenal intraepithelial gamma/delta T cells and soluble CD8, neopterin, and beta 2-microglobulin in serum of IgA-deficient subjects with or without IgG subclass deficiency. Clin Exp Immunol. 1993; 94(1):91-8.
35. Hanson L A, Brandtzaeg P. The discovery of secretory IgA and the mucosal immune system. Immunol Today. 1993; 14(8):416-7.
36. Nilssen D E, Friman V, Theman K, Bjorkander J, Kilander A, Holmgren J, et al. B-cell activation in duodenal mucosa after oral cholera vaccination in IgA deficient subjects with or without IgG subclass deficiency. Scand J. Immunol. 1993; 38(2):201-8.
37. Scott H, Halstensen T, Brandtzaeg P. The immune system of the gastrointestinal tract. Pediatr Allergy Immunol. 1993; 4(3 Suppl):7-15.
38. Rognum T O, Thrane S, Stoltenberg L, Vege A, Brandtzaeg P. Development of intestinal mucosal immunity in fetal life and the first postnatal months. Pediatr Res. 1992; 32(2): 145-9.
39. Muller F, Holberg-Petersen M, Rollag H, Degre M, Brandtzaeg P, Froland S S. Nonspecific oral immunity in individuals with HIV infection. J Acquir Immune Defic Syndr. 1992; 5(1):46-51.
40. Everson M P, Lemak D G, McDuffie D S, Koopman W J, McGhee J R, Beagley K W. Dendritic cells from Peyer's patch and spleen induce different T helper cell responses. J Interferon Cytokine Res. 1998; 18(2):103-15.
41. Everson M P, McDuffie D S, Lemak D G, Koopman W J, McGhee J R, Beagley K W. Dendritic cells from different tissues induce production of different T cell cytokine profiles. J Leukoc Biol. 1996; 59(4):494-8.
42. Everson M P, Koopman W J, McGhee J R, Beagley K W. Dendritic cells regulate development of alloantigenic and mitogenic TH1 versus TH2 responses. Adv Exp Med Biol. 1995; 378:347-9.
43. Beagley K W, Eldridge J H, Kiyono H, Everson M P, Koopman W J, Honjo T, et al. Recombinant murine IL-5 induces high rate IgA synthesis in cycling IgA-positive Peyer's patch B cells. J. Immunol. 1988; 141(6):2035-42.
44. Spalding D M, Williamson S I, McGhee J R, Koopman W J. Peyer's patch dendritic cells: isolation and functional comparison with murine spleen dendritic cells. Immunobiology. 1984; 168(3-5):380-90.
45. Spalding D M, Williamson S I, Koopman W J, McGhee J R. Preferential induction of polyclonal IgA secretion by murine Peyer's patch dendritic cell-T cell mixtures. J Exp Med. 1984; 160(3):941-6.
46. Spalding D M, Koopman W J, Eldridge J H, McGhee J R, Steinman R M. Accessory cells in murine Peyer's patch. I. Identification and enrichment of a functional dendritic cell. J Exp Med. 1983; 157(5):1646-59.
47. Kiyono H, McGhee J R, Mosteller L M, Eldridge J H, Koopman W J, Kearney J F, et al. Murine Peyer's patch T cell clones. Characterization of antigen-specific helper T cells for immunoglobulin A responses. J Exp Med. 1982; 156(4):1115-30.
48. Torii M, McGhee J R, Koopman W J, Hamada S, Michalek S M. Lymphoid cell responses to bacterial cell wall components: polyclonal and immune responses of murine B cells to *Streptococcus* mutans carbohydrate antigens. J. Immunol. 1981; 127(5):2106-12.
49. Cassilly D, Kantor S, Knight L C, Maurer A H, Fisher R S, Semler J, et al. Gastric emptying of a non-digestible solid: assessment with simultaneous SmartPill pH and pressure capsule, antroduodenal manometry, gastric emptying scintigraphy. Neurogastroenterol Motil. 2008; 20(4):311-9.
50. Rao S S, Kuo B, McCallum R W, Chey W D, DiBaise J K, Hasler W L, et al. Investigation of colonic and whole-gut transit with wireless motility capsule and radiopaque markers in constipation. Clin Gastroenterol Hepatol. 2009; 7(5):537-44.
51. Eldridge J H, Gilley R M, Staas J K, Moldoveanu Z, Meulbroek J A, Tice T R. Biodegradable microspheres: vaccine delivery system for oral immunization. Curr Top Microbiol Immunol. 1989; 146:59-66.
52. Theilacker C, Kropec A, Hammer F, Sava I, Wobser D, Sakinc T, et al. Protection Against *Staphylococcus aureus* by Antibody to the Polyglycerolphosphate Backbone of Heterologous Lipoteichoic Acid. J Infect Dis. 2012; 205 (7):1076-85.
53. Sovran L. World Vaccine Congress Lyon—Terrapinn's 11th Annual Congress. IDrugs. 2009; 12(12):738-41.
54. *Staphylococcus aureus* vaccine conjugate—Nabi: Nabi-StaphVAX, StaphVAX. Drugs R D. 2003; 4(6):383-5.
55. Jones T. StaphVAX (Nabi). Curr Opin Investig Drugs. 2002; 3(1):48-50.
56. Fattom A, Fuller S, Propst M, Winston S, Muenz L, He D, et al. Safety and immunogenicity of a booster dose of *Staphylococcus aureus* types 5 and 8 capsular polysaccharide conjugate vaccine (StaphVAX) in hemodialysis patients. Vaccine. 2004; 23(5):656-63.
57. Fattom A I, Horwith G, Fuller S, Propst M, Naso R. Development of StaphVAX, a polysaccharide conjugate vaccine against *S. aureus* infection: from the lab bench to phase III clinical trials. Vaccine. 2004; 22(7):880-7.
58. Weisman L E. Antibody for the prevention of neonatal noscocomial staphylococcal infection: a review of the literature. Arch Pediatr. 2007; 14 Suppl 1:S31-4.
59. Rescia V C, Takata C S, de Araujo P S, Bueno da Costa M H. Dressing liposomal particles with chitosan and poly(vinylic alcohol) for oral vaccine delivery. J Liposome Res. 2011; 21(1):38-45.
60. Faure G C, Hauer S, Mole C, Bene M C. Peripheral blood specific antibody-forming cells after oral stimulation with a ribosomal vaccine. Dev Biol Stand. 1992; 77:175-81.
61. Li F Q, Fei Y B, Su H, Hu J H. [Oral vaccination and vaccine-entrapped microparticle delivery system]. Yao Xue Xue Bao. 2007; 42(3):245-51.
62. Pniewski T, Kapusta J, Bociag P, Wojciechowicz J, Kostrzak A, Gdula M, et al. Low-dose oral immunization with lyophilized tissue of herbicide-resistant lettuce expressing hepatitis B surface antigen for prototype plant-derived vaccine tablet formulation. J Appl Genet. 2011; 52(2):125-36.
63. Pniewski T, Kapusta J, Bociag P, Kostrzak A, Fedorowicz-Stronska O, Czyz M, et al. Plant expression, lyophilisation and storage of HBV medium and large surface antigens for a prototype oral vaccine formulation. Plant Cell Rep. 2012; 31(3):585-95.

64. Larhed A, Stertman L, Edvardsson E, Sjoholm I. Starch microparticles as oral vaccine adjuvant: antigen-dependent uptake in mouse intestinal mucosa. J Drug Target. 2004; 12(5):289-96.
65. Prabakaran M, Madhan S, Prabhu N, Geng G Y, New R, Kwang J. Reverse micelle-encapsulated recombinant baculovirus as an oral vaccine against H5N1 infection in mice. Antiviral Res. 2010; 86(2):180-7.
66. Carter K C, Ferro V A, Alexander J, Mullen A B. Translation of an experimental oral vaccine formulation into a commercial product. Methods. 2006; 38(2):65-8.
67. Louie J K, Acosta M, Samuel M C, Schechter R, Vugia D J, Harriman K, et al. A novel risk factor for a novel virus: obesity and 2009 pandemic influenza A (H1N1). Clin Infect Dis. 2011; 52(3):301-12.
68. Kim Y H, Kim J K, Kim D J, Nam J H, Shim S M, Choi Y K, et al. Diet-induced obesity dramatically reduces the efficacy of a 2009 pandemic H1N1 vaccine in a mouse model. J Infect Dis. 2012; 205(2):244-51.
69. Kim Y C, Quan F S, Yoo D G, Compans R W, Kang S M, Prausnitz M R. Enhanced memory responses to seasonal H1N1 influenza vaccination of the skin with the use of vaccine-coated microneedles. J Infect Dis. 2010; 201(2):190-8.
70. Shamsuzzaman S, Ahmed T, Mannoor K, Begum Y A, Bardhan P K, Sack R B, et al. Robust gut associated vaccine-specific antibody-secreting cell responses are detected at the mucosal surface of Bangladeshi subjects after immunization with an oral killed bivalent *V. cholerae* O1/O139 whole cell cholera vaccine: comparison with other mucosal and systemic responses. Vaccine. 2009; 27(9):1386-92.
71. Ano G, Esquisabel A, Pastor M, Talavera A, Cedre B, Fernandez S, et al. A new oral vaccine candidate based on the microencapsulation by spray-drying of inactivated *Vibrio cholerae*. Vaccine. 2011; 29(34):5758-64.
72. Clark S, Cross M L, Smith A, Court P, Vipond J, Nadian A, et al. Assessment of different formulations of oral *Mycobacterium bovis* Bacille Calmette-Guerin (BCG) vaccine in rodent models for immunogenicity and protection against aerosol challenge with *M. bovis*. Vaccine. 2008; 26(46):5791-7.
73. Delgado A, Lavelle E C, Hartshorne M, Davis S S. PLG microparticles stabilised using enteric coating polymers as oral vaccine delivery systems. Vaccine. 1999; 17(22):2927-38.
74. Kozbor D. Cancer vaccine with mimotopes of tumor-associated carbohydrate antigens. Immunol Res. 2010; 46(1-3):23-31.
75. Segal B H, Wang X Y, Dennis C G, Youn R, Repasky E A, Manjili M H, et al. Heat shock proteins as vaccine adjuvants in infections and cancer. Drug Discov Today. 2006; 11(11-12):534-40.
76. Wang X Y, Kazim L, Repasky E A, Subjeck J R. Characterization of heat shock protein 110 and glucose-regulated protein 170 as cancer vaccines and the effect of fever-range hyperthermia on vaccine activity. J. Immunol. 2001; 166(1):490-7.
77. Odunsi K, Jungbluth A A, Stockert E, Qian F, Gnjatic S, Tammela J, et al. NY-ESO-1 and LAGE-1 cancer-testis antigens are potential targets for immunotherapy in epithelial ovarian cancer. Cancer Res. 2003; 63(18):6076-83.

What is claimed is:

1. An oral formulation which delivers a first antigen in the vicinity of the distal ileum and a second antigen in the vicinity of the right colon and/or appendix, the formulation comprising a first capsule and a second capsule, wherein:

(a) the first capsule comprises
(i) the second capsule and
(ii) a first plurality of cores comprising the first antigen, wherein a first enteric coating encapsulates the first capsule, and is substantially soluble at a pH between about 7.0 and about 7.6; and
(b) the second capsule comprises a second plurality of cores comprising the second antigen, wherein a second enteric coating encapsulates the second capsule, and is substantially soluble at a pH of less than 6.5;
wherein the first capsule delivers the second capsule and the first plurality of cores to the distal ileum, and the second capsule delivers the second plurality of cores to the right colon and/or appendix.

2. The oral formulation of claim 1, wherein the first and/or second antigen is an attenuated virus or an antigen derived therefrom.

3. The oral formulation of claim 1, wherein the first and/or second antigen is a virus, or an antigen derived therefrom.

4. The oral formulation of claim 3, wherein the virus is selected from the group consisting of Adenoviridae, Faviviridae, Herpesviridae, Herpadnaviridae, Orthoinyxoviridae, Papovaviridae, Paramyxoviridae, Picornaviridae, proxvirdae, Reoviridae, Retroviridae, Rhabdoviridae, Togaviridae, and any combinations thereof.

5. The oral formulation of claim 3, wherein the virus is selected from the group consisting of adenovirus, herpes simplex viruss, varicella zoster virus, cytomegalovims, Epstein Barr virus, hepatitis A virus, hepatitis B virus, hepatitis C virus, influenza virus, human papilloma viruses, parainfluenza virus, measles virus, respiratory syncytial virus, poliovirus, Coxsackie virus, rhinovirus, vacinia virus, variola virus, rotavirus, human T lymphotropic virus-1, human immunodeficiency virus (HIV), rabies virus, rubella virus, arbovirus, enteroviruses, Norwalk virus, and any combinations thereof.

6. The oral formulation of claim 1, wherein the first and/or second antigen is an intracellular pathogen or parasite, or an antigen derived therefrom.

7. The oral formulation of claim 6, wherein the intracellular pathogen or parasite is selected from the group consisting of *Ajipia* spp, *Brucella* spp, *Burkholderia* pseudomallei, *Chlamydia* spp, *Coxiella burnetii, Francisella tularensis, Legionella* pneumophila, *Listeria monocytogenes, Mycobacterium avium, Mycobacterium leprae, Mycobacterium* tuberculosis, *Neisseria gonorrhoeae, Rickettsiae, Salmonella* typhi, *Shigella* dysenteriae, *Yersinia pestis, Plasmodium* spp, *Theileria parva, Toxoplasma gondii, Cryptosporidium parvum, Leishmania* spp, *Trypanosome* cruzi, *Cryptococcus neoformans, Giardia* spp, *Cryptosporidia* spp, and any combinations thereof.

8. The oral formulation of claim 1, wherein the first and/or second antigen is a vector transmitted antigen, or an antigen derived therefrom.

9. The oral formulation of claim 8, wherein the vector transmitted antigen is selected from the group consisting of *Plasmodium* spp, *Borrelia* spp, and any combinations thereof.

10. The oral formulation of claim 1, wherein the first and/or second antigen is a bacteria, or an antigen derived therefrom.

11. The oral formulation of claim 10, wherein the bacteria is selected from the group consisting of *Vibrio cholera, Salmonella* spp, *Shigella* spp, *Campylocater* spp, *Leptospira* spp, *Helicobacter* pylori Enterotoxigenic *E. coli, Listeria* spp, *Staphylococcus aureus, Streptococcus pneumoniae,* and any combinations thereof.

12. The oral formulation of claim 11, wherein the Enterotoxigenic *E. coli* is *E. Coli* 0157.

13. The oral formulation of claim 1, wherein the first and/or second antigen is a cancer-related antigen, or an antigen derived therefrom.

14. The oral formulation of claim 13, wherein the cancer-related antigen is selected from the group consisting of NY-ESO-1, GD2 ganglioside, 47-LDA mimotope of GD2, heat shock proteins, cancer-testis (CT) antigens, epithelial ovarian cancer (EOC) antigen, MUC1, and ovarian, pancreatic, hepatocellular, colon, breast, lung, and brain cancer antigens, and any combinations thereof.

15. The oral formulation of claim 1, wherein the first plurality of the cores in the first capsule and/or the second plurality of cores in the second capsule are formulated as microgranules, granules, powder, troches, lozenges, suspensions, microsuspensions, dispersible powder, emulsions, or microemulsions.

16. The oral formulation of claim 1, wherein the first enteric coating and/or the second enteric coating comprises copolymers of acrylic and methacrylic acid esters.

17. The oral formulation of claim 1, wherein the first and/or second capsule further comprise an adjuvant.

18. The oral formulation of claim 1, wherein the first and/or second capsule further comprise a pharmaceutically acceptable excipient.

* * * * *